US006949086B2

(12) United States Patent
Ferguson et al.

(10) Patent No.: US 6,949,086 B2
(45) Date of Patent: Sep. 27, 2005

(54) SELDINGER SAFETY SHIELD FOR MEDICAL NEEDLES

(75) Inventors: F. Mark Ferguson, Salt Lake City, UT (US); Richard L. Fiser, Kirkwood, MO (US); James R. Curtis, Deland, FL (US); Charles V. Owen, Highland, UT (US); David L. Thorne, Kaysville, UT (US); Mark A. Nelson, Sandy, UT (US); Roy L. Barrus, West Bountiful, UT (US); Gale H. Thorne, Jr., Bountiful, UT (US); Eugene E. Weilbacher, Chesterfield, MO (US); Michael Thorne, Bountiful, UT (US); Steven Brown, Roy, UT (US); Donald Solomon, Ogden, UT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 10/459,164

(22) Filed: Jun. 11, 2003

(65) Prior Publication Data

US 2003/0229317 A1 Dec. 11, 2003

Related U.S. Application Data

(60) Division of application No. 09/892,593, filed on Jun. 27, 2001, which is a continuation-in-part of application No. 09/433,449, filed on Nov. 4, 1999, now Pat. No. 6,280,420.
(60) Provisional application No. 60/296,968, filed on Jun. 8, 2001, provisional application No. 60/275,810, filed on Mar. 14, 2001, now abandoned, provisional application No. 60/275,886, filed on Mar. 14, 2001, and provisional application No. 60/254,506, filed on Dec. 8, 2000.

(51) Int. Cl.$^7$ .............................. A61M 5/32; A61M 5/00
(52) U.S. Cl. ....................... 604/198; 604/263; 600/576
(58) Field of Search ..................... 604/110, 164.08, 604/192, 198, 263; 600/576; 128/919

(56) References Cited

U.S. PATENT DOCUMENTS

| 1,779,451 A | 10/1930 | Sponsel |
| 2,559,474 A | 7/1951 | Son ............................ 128/215 |
| 2,700,385 A | 1/1955 | Ortiz ........................... 128/215 |
| 2,836,942 A | 6/1958 | Miskel .......................... 53/25 |
| 2,854,976 A | 10/1958 | Heydrich .................... 128/221 |
| 2,953,243 A | 9/1960 | Roehr ......................... 206/43 |
| 3,021,942 A | 2/1962 | Hamilton ..................... 206/43 |
| 3,073,307 A | 1/1963 | Stevens ...................... 128/221 |
| 3,074,542 A | 1/1963 | Myerson et al. .............. 206/43 |
| 3,255,873 A | 6/1966 | Speelman .................... 206/56 |
| 3,294,231 A | 12/1966 | Vanderbeck ................. 206/63 |
| 3,323,523 A | 6/1967 | Scislowicz et al. ......... 128/214 |
| 3,329,146 A | 7/1967 | Waldman, Jr. .............. 128/221 |

(Continued)

FOREIGN PATENT DOCUMENTS

| EP | 0 144 483 | 6/1985 | ............ A61M/5/00 |
| EP | 0 344 606 A2 | 12/1989 | |

(Continued)

*Primary Examiner*—Nicholas D. Lucchesi
*Assistant Examiner*—Catherine S. Williams
(74) *Attorney, Agent, or Firm*—Mark S. Leonardo; Peter B. Sorell; Brown Rudnick Berlack Israels LLP

(57) ABSTRACT

Medical needle shield apparatus for covering a needle after use. In embodiments of this invention a shield with two or more segments hingedly connected to each other is movable from a retracted position where the needle is exposed, to an extended position where the shield extends beyond the end of the needle. The needle is affixed in a hub of a medical needle device, and the shield is articulated to the hub. At least one of the two or more segments has an open orifice through which the needle passes to form an axis of intersection about the needle. The shield includes a channel for covering the needle when the shield is linearly extended. One or more locks associated with one or more of the segments secures one or more of the segments relative to the shield in the extended position.

20 Claims, 59 Drawing Sheets

U.S. PATENT DOCUMENTS

| | | | |
|---|---|---|---|
| 3,333,682 A | 8/1967 | Burke | 206/43 |
| 3,367,488 A | 2/1968 | Hamilton | 206/63 |
| 3,485,239 A | 12/1969 | Vanderbeck | 128/218 |
| 3,537,452 A | 11/1970 | Wilks | 128/214 |
| 3,587,575 A | 6/1971 | Lichtenstein | 128/215 |
| 3,610,240 A | 10/1971 | Harautuneian | 128/214 |
| 3,658,061 A | 4/1972 | Hall | 128/214 |
| 3,828,775 A | 8/1974 | Armel | 128/218 |
| 3,840,008 A | 10/1974 | Noiles | 128/221 |
| 3,890,971 A | 6/1975 | Leeson et al. | 128/218 |
| 3,904,033 A | 9/1975 | Haerr | 206/349 |
| 3,934,722 A | 1/1976 | Goldberg | 206/365 |
| 3,968,876 A | 7/1976 | Brookfield | 206/365 |
| 4,040,419 A | 8/1977 | Goldman | 128/215 |
| 4,106,621 A | 8/1978 | Sorenson | 206/365 |
| 4,113,090 A | 9/1978 | Carstens | 206/365 |
| 4,139,009 A | 2/1979 | Alvarez | 128/218 |
| 4,175,008 A | 11/1979 | White | 435/295 |
| 4,270,536 A | 6/1981 | Lemelson | 128/218 |
| 4,300,678 A | 11/1981 | Gyure et al. | 206/364 |
| 4,375,849 A | 3/1983 | Hanifl | 206/366 |
| 4,430,082 A | 2/1984 | Schwabacher | 604/263 |
| 4,592,744 A | 6/1986 | Jagger et al. | 604/192 |
| 4,634,428 A | 1/1987 | Cuu | 604/110 |
| 4,643,722 A | 2/1987 | Smith, Jr. | 604/192 |
| 4,659,330 A | 4/1987 | Nelson et al. | 604/192 |
| 4,664,259 A | 5/1987 | Landis | 206/365 |
| 4,664,654 A | 5/1987 | Strauss | 604/198 |
| 4,681,567 A | 7/1987 | Masters et al. | 604/198 |
| 4,695,274 A | 9/1987 | Fox | 604/192 |
| 4,702,738 A | 10/1987 | Spencer | 604/198 |
| 4,723,943 A | 2/1988 | Spencer | 604/198 |
| 4,728,320 A | 3/1988 | Chen | 604/110 |
| 4,728,321 A | 3/1988 | Chen | 604/110 |
| 4,731,059 A | 3/1988 | Wanderer et al. | 604/192 |
| 4,735,311 A | 4/1988 | Lowe et al. | 206/365 |
| 4,735,618 A | 4/1988 | Hagen | 604/192 |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,836 A | 5/1988 | Luther | 604/198 |
| 4,747,837 A | 5/1988 | Hauck | 604/198 |
| 4,772,272 A | 9/1988 | McFarland | 604/198 |
| 4,778,453 A | 10/1988 | Lopez | 604/110 |
| 4,781,697 A | 11/1988 | Slaughter | 604/192 |
| 4,782,841 A | 11/1988 | Lopez | 128/164 |
| 4,790,828 A | 12/1988 | Dombrowski et al. | 604/198 |
| 4,795,432 A | 1/1989 | Karczmer | 604/110 |
| 4,795,443 A | 1/1989 | Permenter et al. | 604/198 |
| 4,801,295 A | 1/1989 | Spencer | 604/198 |
| 4,804,372 A | 2/1989 | Laico et al. | 604/198 |
| 4,813,426 A | 3/1989 | Haber et al. | 128/763 |
| 4,816,022 A | 3/1989 | Poncy | 604/198 |
| 4,816,024 A | 3/1989 | Sitar et al. | 604/192 |
| 4,819,659 A | 4/1989 | Sitar | 128/764 |
| 4,820,277 A | 4/1989 | Norelli | 604/192 |
| 4,826,490 A | 5/1989 | Byrne et al. | 604/198 |
| 4,826,491 A | 5/1989 | Schramm | 604/198 |
| 4,838,871 A | 6/1989 | Luther | 604/192 |
| 4,840,619 A | 6/1989 | Hughes | 604/187 |
| 4,842,587 A | 6/1989 | Poncy | 604/198 |
| 4,846,796 A | 7/1989 | Carrell et al. | 604/110 |
| 4,846,811 A | 7/1989 | Vanderhoof | 604/263 |
| 4,850,968 A | 7/1989 | Romano | 604/110 |
| 4,850,976 A | 7/1989 | Heinrich et al. | 604/192 |
| 4,850,977 A | 7/1989 | Bayless | 604/198 |
| 4,850,978 A | 7/1989 | Dudar et al. | 604/201 |
| 4,850,994 A | 7/1989 | Zerbst et al. | 604/198 |
| 4,850,996 A | 7/1989 | Cree | 604/198 |
| 4,858,607 A | 8/1989 | Jordan et al. | 128/314 |
| 4,863,434 A | 9/1989 | Bayless | 604/198 |
| 4,863,435 A | 9/1989 | Sturman et al. | 604/198 |
| 4,863,436 A | 9/1989 | Glick | 604/198 |
| 4,867,172 A | 9/1989 | Haber et al. | 128/763 |
| 4,867,746 A | 9/1989 | Dufresne | 604/192 |
| 4,872,552 A | 10/1989 | Unger | 206/365 |
| 4,874,382 A | 10/1989 | Lindemann et al. | 604/195 |
| 4,874,383 A | 10/1989 | McNaughton | 604/198 |
| 4,874,384 A | 10/1989 | Nunez | 604/198 |
| 4,883,469 A | 11/1989 | Glazier | 604/192 |
| 4,886,503 A | 12/1989 | Miller | 604/192 |
| 4,887,998 A | 12/1989 | Martin et al. | 604/110 |
| 4,888,001 A | 12/1989 | Schoenberg | 604/162 |
| 4,892,107 A | 1/1990 | Haber | 128/763 |
| 4,892,521 A | 1/1990 | Laico et al. | 604/192 |
| 4,898,589 A | 2/1990 | Dolgin et al. | 604/198 |
| 4,900,309 A | 2/1990 | Netherton et al. | 604/192 |
| 4,904,244 A | 2/1990 | Harsh et al. | 604/187 |
| 4,911,694 A | 3/1990 | Dolan | 604/198 |
| 4,911,706 A | 3/1990 | Levitt | 604/198 |
| 4,927,018 A | 5/1990 | Yang et al. | 206/365 |
| 4,929,241 A | 5/1990 | Kulli | 604/263 |
| 4,935,012 A | 6/1990 | Magre et al. | 604/192 |
| 4,935,013 A | 6/1990 | Haber et al. | 604/192 |
| 4,936,830 A | 6/1990 | Verlier | 604/110 |
| 4,944,397 A | 7/1990 | Miller | 206/365 |
| 4,944,731 A | 7/1990 | Cole | 604/192 |
| 4,950,249 A | 8/1990 | Jagger et al. | 604/192 |
| 4,950,250 A | 8/1990 | Haber et al. | 604/192 |
| 4,978,344 A | 12/1990 | Dombrowski et al. | 604/198 |
| 4,982,842 A | 1/1991 | Hollister | 206/365 |
| 4,985,021 A | 1/1991 | Straw et al. | 604/198 |
| 4,994,041 A | 2/1991 | Dombrowski et al. | 604/164 |
| 5,000,744 A | 3/1991 | Hoffman et al. | 604/232 |
| 5,015,240 A | 5/1991 | Soproni et al. | 604/192 |
| 5,057,089 A | 10/1991 | Greco | 604/198 |
| 5,059,180 A | 10/1991 | McLees | 604/110 |
| 5,092,851 A | 3/1992 | Ragner | 604/192 |
| 5,108,379 A | 4/1992 | Dolgin et al. | 604/198 |
| RE34,045 E | 8/1992 | McFarland | 604/198 |
| 5,135,509 A | 8/1992 | Olliffe | 604/192 |
| 5,139,489 A | 8/1992 | Hollister | 604/192 |
| 5,147,303 A | 9/1992 | Martin | 604/110 |
| 5,154,285 A | 10/1992 | Hollister | 206/365 |
| 5,176,655 A | 1/1993 | McCormick et al. | 604/198 |
| 5,176,656 A | 1/1993 | Bayless | 604/198 |
| 5,193,552 A | 3/1993 | Columbus et al. | 128/760 |
| 5,195,983 A | 3/1993 | Boese | 604/192 |
| 5,209,739 A | 5/1993 | Talalay | 604/195 |
| 5,232,454 A | 8/1993 | Hollister | 604/192 |
| 5,232,455 A | 8/1993 | Hollister | 604/192 |
| 5,242,417 A | 9/1993 | Paudler | 604/192 |
| 5,242,418 A | 9/1993 | Weinstein | 604/192 |
| 5,246,427 A | 9/1993 | Sturman et al. | 604/192 |
| 5,246,428 A | 9/1993 | Falknor | 604/198 |
| 5,250,031 A | 10/1993 | Kaplan et al. | 604/110 |
| 5,254,099 A | 10/1993 | Kuracina et al. | 604/198 |
| 5,256,152 A | 10/1993 | Marks | 604/198 |
| 5,256,153 A | 10/1993 | Hake | 604/198 |
| 5,277,311 A | 1/1994 | Hollister | 206/365 |
| 5,290,255 A | 3/1994 | Vallelunga et al. | 604/197 |
| 5,304,137 A | 4/1994 | Fluke | 604/110 |
| 5,312,369 A | 5/1994 | Arcusin et al. | 604/192 |
| 5,334,158 A | 8/1994 | McLees | 604/110 |
| 5,348,544 A | * 9/1994 | Sweeney et al. | 604/192 |
| 5,356,392 A | 10/1994 | Firth et al. | 604/198 |
| 5,403,283 A | 4/1995 | Luther | 604/164 |
| 5,403,286 A | 4/1995 | Lockwood, Jr. | 604/110 |
| 5,407,436 A | 4/1995 | Toft et al. | 604/195 |
| 5,411,492 A | 5/1995 | Sturman et al. | 604/263 |
| 5,423,765 A | 6/1995 | Hollister | 604/192 |

| | | | |
|---|---|---|---|
| 5,423,766 A | 6/1995 | Di Cesare | 604/192 |
| 5,425,720 A | 6/1995 | Rogalsky et al. | 604/198 |
| 5,447,501 A | 9/1995 | Karlsson et al. | 604/198 |
| 5,466,223 A | 11/1995 | Bressler et al. | 604/110 |
| 5,480,385 A | 1/1996 | Thorne et al. | 604/110 |
| 5,487,733 A | 1/1996 | Caizza et al. | 604/110 |
| 5,487,734 A | 1/1996 | Thorne et al. | 604/195 |
| 5,490,841 A | 2/1996 | Landis | 604/110 |
| 5,498,243 A | 3/1996 | Vallelunga et al. | 604/197 |
| 5,531,694 A | 7/1996 | Clemens et al. | 604/110 |
| 5,533,980 A | 7/1996 | Sweeney et al. | 604/192 |
| 5,538,508 A | 7/1996 | Steyn | 604/192 |
| 5,542,927 A | 8/1996 | Thorne et al. | 604/110 |
| 5,549,568 A | 8/1996 | Shields | 604/192 |
| 5,549,570 A | 8/1996 | Rogalsky | 604/198 |
| 5,549,708 A | 8/1996 | Thorne et al. | 604/110 |
| 5,562,629 A | 10/1996 | Haughton et al. | 604/158 |
| 5,562,631 A | 10/1996 | Bogert | 604/164 |
| 5,573,510 A | 11/1996 | Isaacson | 604/158 |
| 5,584,816 A | 12/1996 | Gyure et al. | 604/192 |
| 5,584,818 A | 12/1996 | Morrison | 604/197 |
| 5,599,318 A | 2/1997 | Sweeney et al. | 604/263 |
| 5,611,782 A * | 3/1997 | Haedt | 604/198 |
| 5,643,220 A | 7/1997 | Cosme | 604/192 |
| 5,672,161 A | 9/1997 | Allen et al. | 604/263 |
| 5,695,474 A | 12/1997 | Daugherty | 604/198 |
| 5,695,477 A | 12/1997 | Sfikas | 604/241 |
| 5,700,249 A | 12/1997 | Jenkins | 604/263 |
| 5,735,827 A | 4/1998 | Adwers et al. | 604/263 |
| 5,738,665 A | 4/1998 | Caizza et al. | 604/263 |
| 5,746,718 A | 5/1998 | Steyn | 604/192 |
| 5,746,726 A | 5/1998 | Sweeney et al. | 604/263 |
| 5,755,699 A | 5/1998 | Blecher et al. | 604/198 |
| 5,814,018 A | 9/1998 | Elson et al. | 604/110 |
| 5,817,064 A * | 10/1998 | DeMarco et al. | 604/198 |
| 5,823,997 A | 10/1998 | Thorne | 604/110 |
| 5,843,041 A | 12/1998 | Hake et al. | 604/198 |
| 5,879,337 A * | 3/1999 | Kuracina et al. | 604/192 |
| 5,910,130 A | 6/1999 | Caizza et al. | 604/110 |
| 5,919,168 A | 7/1999 | Wheeler | 604/198 |
| 5,925,020 A | 7/1999 | Nestell | 604/198 |
| 5,951,522 A | 9/1999 | Rosato et al. | 604/177 |
| 5,957,892 A * | 9/1999 | Thorne | 604/162 |
| 5,980,488 A | 11/1999 | Thorne | 604/110 |
| 6,015,397 A | 1/2000 | Elson et al. | 604/192 |
| 6,036,675 A | 3/2000 | Thorne et al. | 604/232 |
| 6,149,629 A | 11/2000 | Wilson et al. | 604/198 |
| 6,171,284 B1 | 1/2001 | Kao et al. | 604/192 |
| RE37,110 E | 3/2001 | Hollister | 206/365 |
| 6,224,576 B1 | 5/2001 | Thorne et al. | 604/198 |
| RE37,252 E | 7/2001 | Hollister | 206/364 |
| 6,254,575 B1 | 7/2001 | Thorne, Jr. et al. | 604/198 |
| 6,280,420 B1 | 8/2001 | Ferguson et al. | 604/198 |
| 6,334,857 B1 | 1/2002 | Hollister et al. | 604/263 |
| 6,582,397 B2 * | 6/2003 | Alesi et al. | 604/110 |
| 2001/0039401 A1 | 11/2001 | Ferguson et al. | |
| 2002/0004650 A1 | 1/2002 | Kuracina et al. | |
| 2002/0072716 A1 | 6/2002 | Barrus et al. | |
| 2003/0004465 A1 | 1/2003 | Ferguson et al. | |

FOREIGN PATENT DOCUMENTS

| | | | |
|---|---|---|---|
| EP | 0 457 477 B1 | 11/1991 | |
| EP | 0 485 345 B1 | 5/1992 | |
| EP | 0 533 308 A1 | 3/1993 | |
| EP | 0 585 391 B1 | 3/1994 | |
| EP | 0 597 857 B1 | 5/1994 | |
| EP | 0 603 365 B1 | 6/1994 | |
| EP | 0 626 924 B1 | 12/1994 | |
| EP | 0 654 281 B1 | 5/1995 | |
| EP | 0 705 613 B1 | 4/1996 | |
| EP | 0 713 710 A1 | 5/1996 | A61M/5/32 |
| EP | 0 807 443 A2 | 11/1997 | A61M/5/32 |
| EP | 0 815 888 A2 | 1/1998 | |
| EP | 0 815 890 A2 | 1/1998 | |
| EP | 0 819 441 A1 | 1/1998 | |
| EP | 0 832 659 A2 | 4/1998 | |
| EP | 0 832 660 A2 | 4/1998 | |
| EP | 1 092 443 A2 | 4/2001 | A61M/5/32 |
| EP | 1 116 493 A1 | 7/2001 | A61M/25/06 |
| GB | 1233302 | 5/1971 | |
| GB | 2 283 429 A | 5/1995 | |
| GB | 2 369 779 | 12/2002 | A61M/5/32 |
| JP | 10-76007 | 3/1998 | |
| JP | 10-127765 | 5/1998 | |
| WO | WO 87/07162 | 12/1987 | |
| WO | WO 89/07955 | 9/1989 | |
| WO | WO 93/17732 | 9/1993 | A61M/3/00 |
| WO | WO 94/19036 | 9/1994 | |
| WO | WO 97/31666 | 4/1997 | A61M/5/00 |
| WO | WO 98/07463 | 2/1998 | |
| WO | WO 98/10816 | 3/1998 | |
| WO | WO 98/11928 | 3/1998 | |
| WO | WO 98/13081 | 4/1998 | |
| WO | WO 00/16832 | 3/2000 | |
| WO | WO 00/38765 | 6/2000 | A61M/5/178 |
| WO | WO 01/32241 A1 | 5/2001 | |
| WO | WO 01/32244 A1 | 5/2001 | |

* cited by examiner

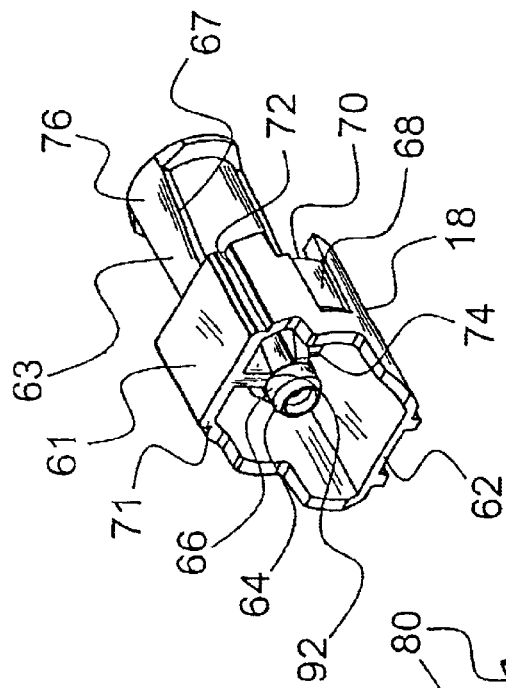
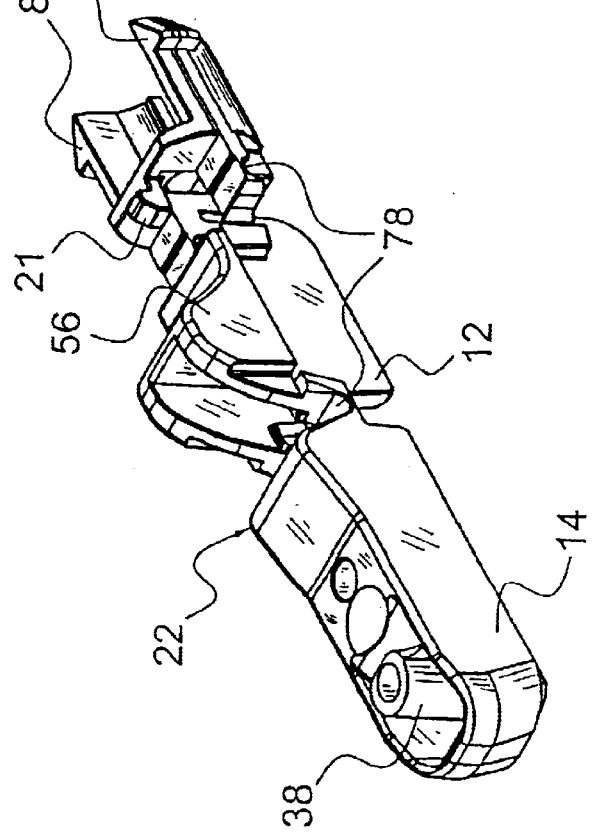

SELDINGER SAFETY SHIELD FOR MEDICAL NEEDLES

CROSS-REFERENCE TO RELATED APPLICATIONS

This patent application is a divisional of U.S. Utility patent application Ser. No. 09/892,593, filed in the U.S. patent and Trademarks Office on Jun. 27, 2001 by Ferguson et al., which is a continuation-in-part of U.S. patent application Ser. No. 09/433,449, filed Nov. 4, 1999 now U.S. Pat. No. 6,280,420, U.S. patent application Ser. No. 09/434,036, filed Nov. 4, 1999 and, U.S. patent application Ser. No. 09/619,190, filed Jul. 19, 2000 and which claims priority to U.S. Provisional patent application Ser. No. 60/254,506, filed on Dec. 8, 2000, U.S. Provisional patent application Ser. No. 60/275,810, filed on Mar. 14, 2001 which is now abandoned, U.S. Provisional patent application Ser. No. 60/275,886, filed Mar. 14, 2001, and U.S. Provisional patent application Ser. No. 60/296,968, filed Jun. 8, 2001, the entire contents of each of these applications being hereby incorporated herein by reference.

BACKGROUND

1. Technical Field

This invention relates generally to safety shields for medical needles, and more particularly, to safety shields that are extensible to shield a needle point of a medical needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the wound than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

There remains a need to provide a more satisfactory solution to a needle safety device.

SUMMARY OF THE INVENTION

The present invention was developed to fill a need for a device which effectively and inexpensively protects a medical needle after use. The present invention seeks to resolve a number of the problems which have been experienced in the background art. More specifically, the apparatus and method of this invention constitute an important advance in the art of safety needle devices.

In one particular embodiment, a medical needle shield apparatus is provided, in accordance with the principles of the present disclosure. The medical needle shield apparatus includes a needle hub having a collar and a shield having a proximal end receivable by the collar. The shield being extensible from a retracted position to an extended position. The collar can be monolithically formed with the needle hub. The needle hub can have a luer fitting configured to attach to a syringe.

In an alternate embodiment, the medical needle shield apparatus includes a needle hub having a collar defining an interior cavity. The needle hub supports a needle having a distal end. A needle shield component includes a proximal and distal end. The proximal end of the shield being receivable within the interior cavity of the collar in an interlocking engagement. The shield being extensible from a retracted position to an extended position wherein the distal end of the shield encloses at least a portion of the distal end of the needle. The shield can include two or more hingedly connected segments, for instance, the shield may include four hingedly connected segments. An interior cavity of the shield may define notches that receive tabs formed with the proximal end of the shield. The tabs may be biased for receipt within the notches.

The shield may be locked in the extended position. The shield may also be irreversibly locked in the extended position. The shield may be locked in the extended position via engagement with the needle or through locking engagement of two or more adjacent hingedly connected shield segments. The shield can include a lock that engages the needle to lock the shield in the extended position. The lock may include a portion configured to flexibly engage the needle and bias to lockably retain the needle. Alternatively, the shield includes locking means to lock the shield in the extended position.

In another embodiment, the distal end of the shield includes a linear bearing configured to enclose at least a portion of the distal end of the needle. The linear bearing may be hingedly connected to and disposed within the distal end of the shield. The linear bearing can be configured to slide along the needle during extension of the shield. The linear bearing can have many configurations such as duckbill or full cylinder. The linear bearing may have a flap configured to align the linear bearing with the needle.

In another embodiment, the shield includes a proximal segment engaging a retention catch or stop formed with the proximal end of the shield to releasably dispose the shield in the retracted position. The needle hub may include a stop or catch which engages the shield in the extended position. The medical needle shield apparatus may include a sheath engageable with the needle hub. The sheath can have guide rails configured to facilitate engagement of the sheath and the needle hub.

In another alternate embodiment, the shield has an articulating actuator configured to urge the shield towards the extended position. The medical needle shield apparatus may further include a tape down member attached to the shield and configured to facilitate extension of the shield. The needle hub can include guide surfaces to facilitate engagement of the shield and the needle hub. The needle hub may include at least one catch or protrusion and the shield may include at least one corresponding protrusion or catch which engage to lock the shield in the extended position.

The shield segments may be connected via living hinges. The segments can include relief portions formed adjacent the living hinges. The relief portions can be configured to flex inwardly toward the needle. The shield may have a proximal segment including at least one rib. The at least one rib may have a transverse orientation.

The medical needle shield apparatus may be configured for use with a port access needle. A pair of wings may be attached to the proximal end of the shield. The shield can include a needle latch that engages the needle in the extended position.

In yet another alternate embodiment, the lock mechanism includes at least one catch for engagement with a corresponding protrusion disposed on the shield in the extended position. The catch may include a capture hole, recess or indentation. The catch may also include a flanged surface. Alternatively, the lock mechanism can include at least one catch for engagement with a corresponding protrusion disposed on the hub in the extended position. The lock may include at least one protrusion or catch for engagement with a corresponding catch or protrusion disposed on the shield in the extended position.

In another embodiment, the medical needle shield apparatus includes a latch which secures a distal segment of the shield in the extended position. The distal segment has an underside including a surface extending over at least a portion of the distal segment for retaining the distal end of the needle. The latch may include at least one lock associated with the distal segment for securing the distal segment to the shield in the extended position. The medical needle shield apparatus may include a retainer for holding the segments in a retracted position. The retainer can include a retainer arm disposed on the needle hub and extending to a corresponding catch disposed on the shield in the retracted position.

In another embodiment, at least one segment includes at least one needle guide for facilitating extension of the segments when extending the shield over the needle. The shield may further include a raised surface for aid in urging the shield to the extended position.

In another embodiment, the medical needle shield apparatus includes a needle hub including a collar and a shield having a distal end and a proximal end receivable by the collar. The shield being extensible from a retracted position to an extended position, wherein the shield includes at least one catch and at least one corresponding protrusion which engage to lock the shield in the extended position. The protrusion can include a latching arm extending from a segment and the catch including a flanged surface disposed adjacent a hinged connection.

In yet another embodiment, the medical needle shield apparatus includes an extensible shield having at least two hingedly connected segments, wherein the segments include reliefs formed adjacent the hinges and configured to flex inwardly.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, wherein:

FIG. 6 is a perspective view of a hub of the safety shield apparatus illustrated in FIG. 1;

FIG. 7 is a perspective view of a shield separate from the hub of the safety shield apparatus illustrated in FIG. 1;

DETAILED DESCRIPTION OF THE EXEMPLARY EMBODIMENTS

Figure 53:
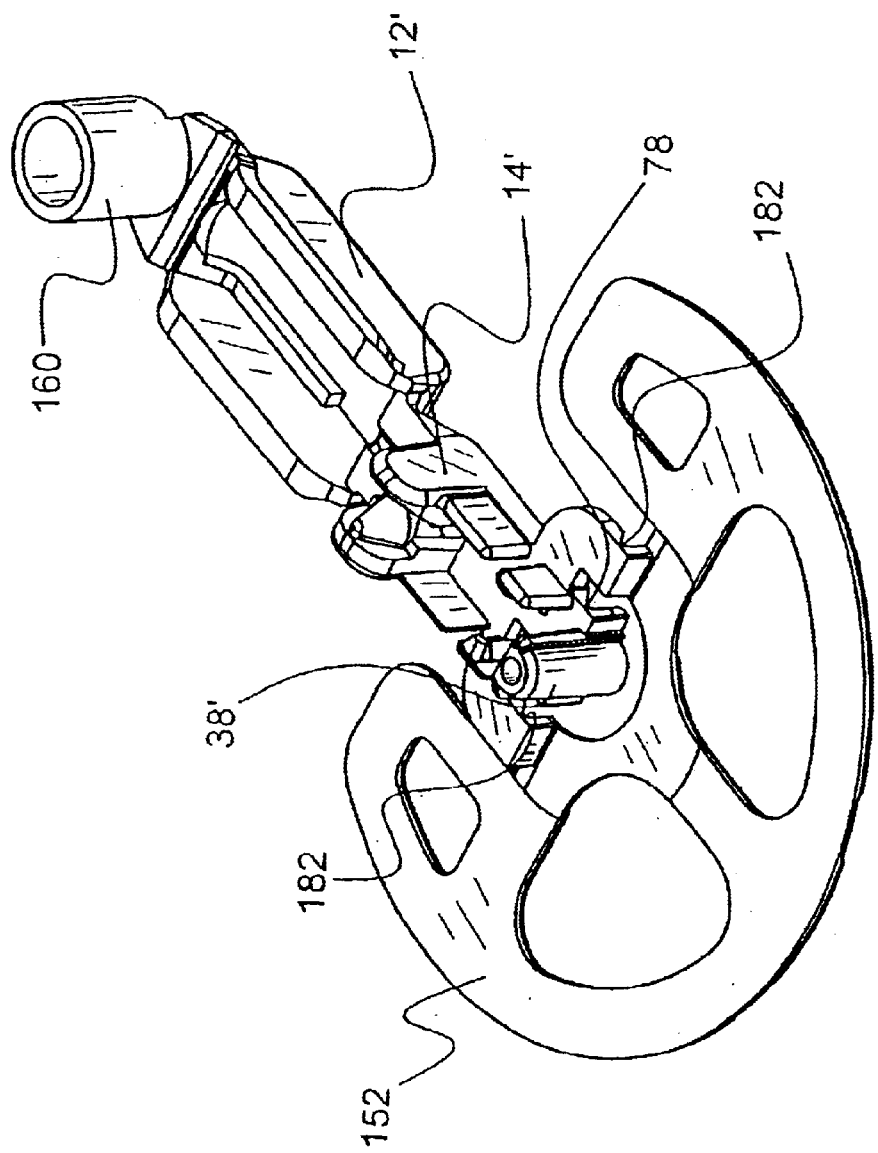
FIG. 53 is a perspective view of the safety shield apparatus illustrated in FIG. 42 showing an alternate embodiment of a disc.

In this description, the term proximal is generally used to indicate relative nearness of a referenced item to a user of a device or a viewer of a perspective drawing of a FIGURE. The term distal is similarly used to indicate relative remoteness. Reference is now made to the embodiments illustrated in FIGS. 1–53 wherein like numerals are used to designate like parts throughout. In cases where parts have similar, but not identical, form and function, numerals with primes may be used for ease in interpretative cross referencing.

Figure 1:
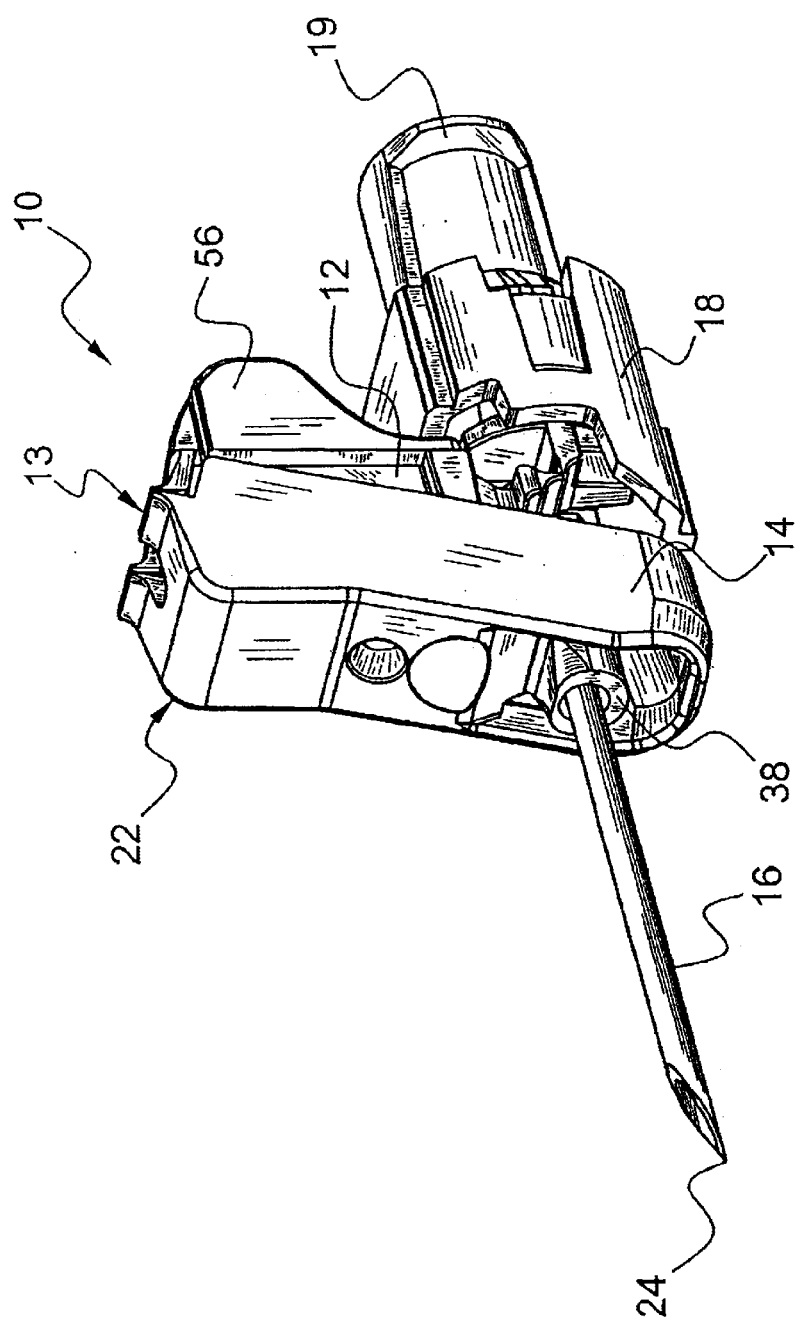
FIG. 1 is a perspective view of a medical needle safety shield apparatus in a retracted position, in accordance with the principles of the present invention.
Figure 2:
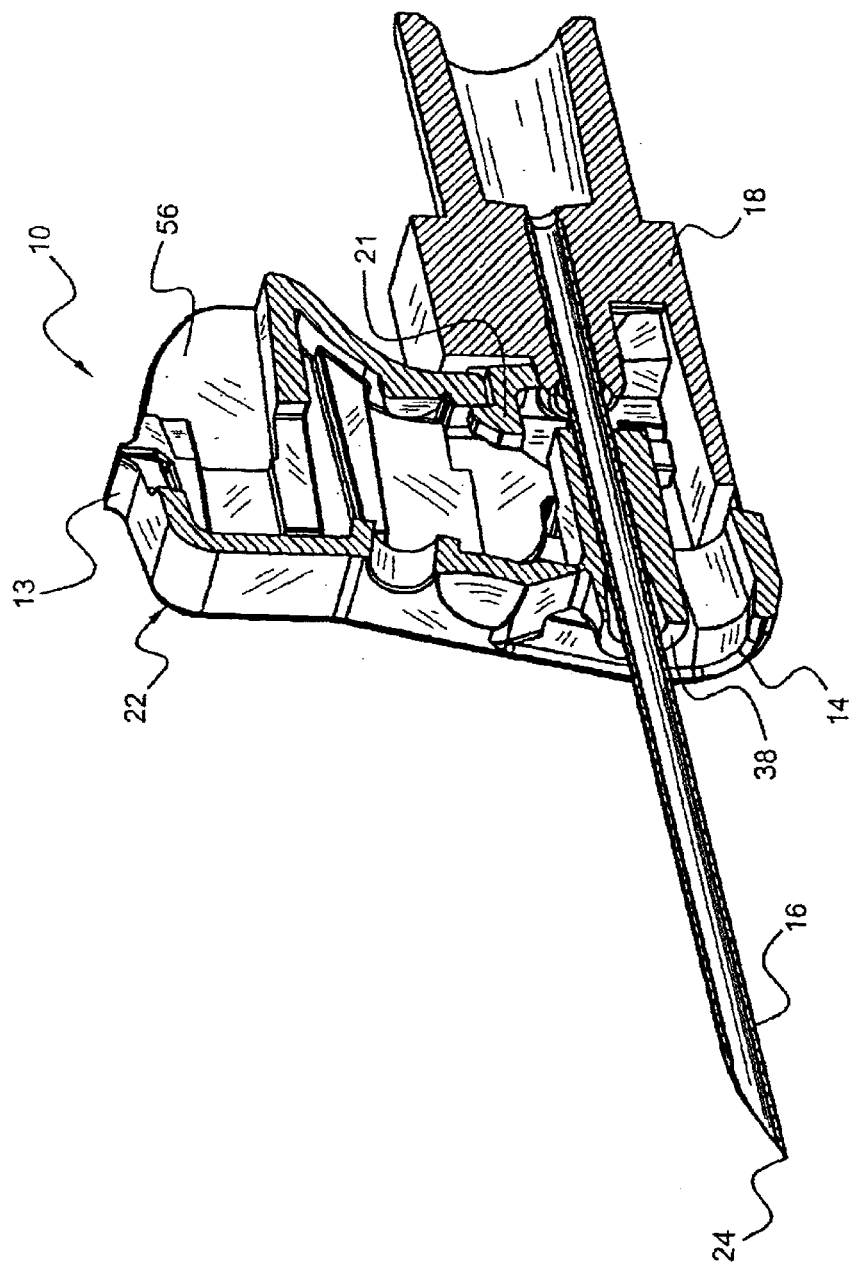
FIG. 2 is a part cross-sectional view of the safety shield apparatus shown in FIG. 1.
Figure 3:
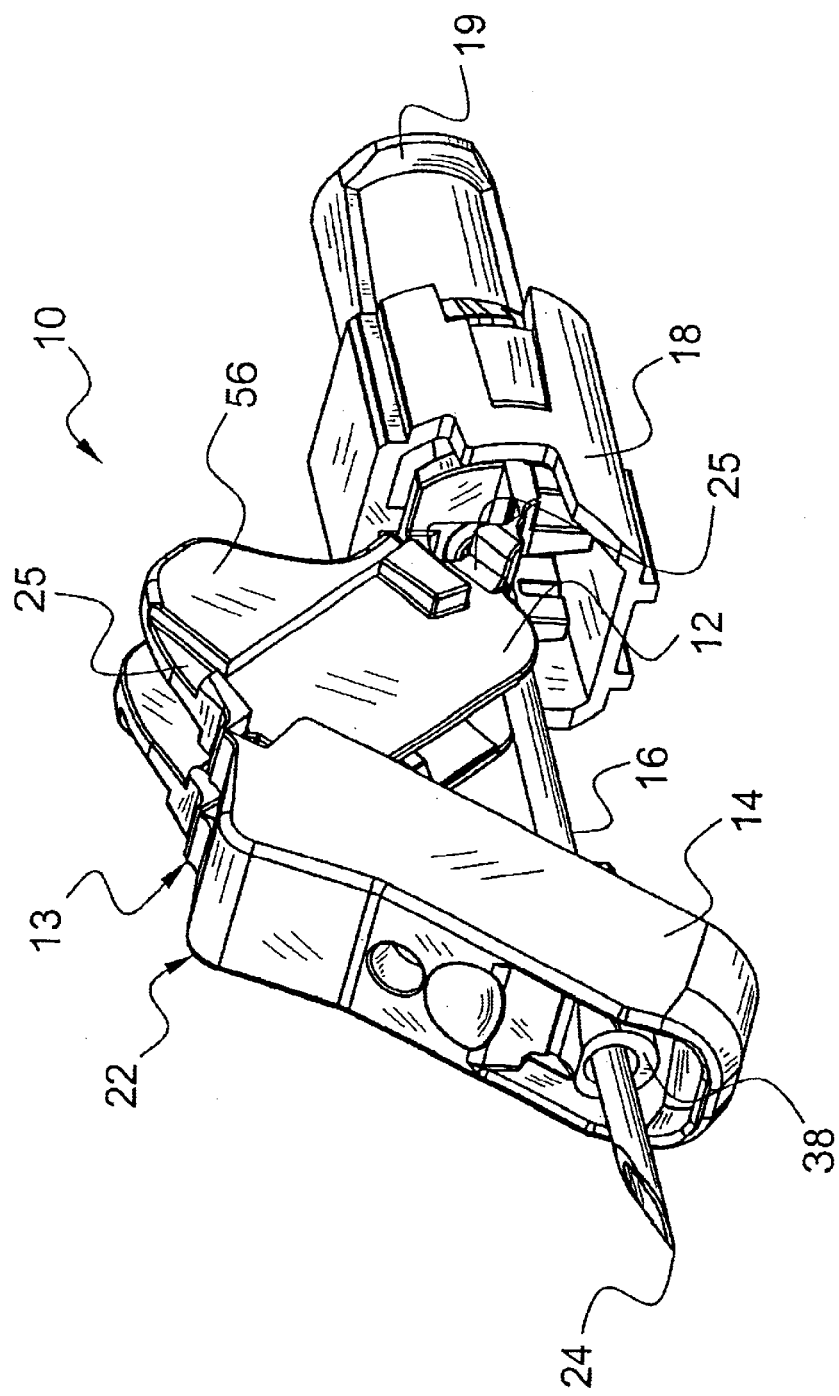
FIG. 3 is a perspective view of the safety shield apparatus illustrated in FIG. 1 at mid-extension.

Referring to FIGS. 1–3, an embodiment of a safety shield apparatus 10 is shown comprising a safety shield 22 of hingedly connected segments 12 and 14 for protecting a needle 16 after use in a medical procedure. The needle 16 has a proximal end and a distal end 24 with the proximal end of the needle 16 being bonded with a hub 18. It is envisioned that needle 16 may be affixed to hub 18 in various manners. Safety shield apparatus 10 has a luer fitting 19 for attachment to various needle devices such as a syringe. It is contemplated that safety shield apparatus 10 may be utilized with other medical needle applications including, but not limited to, phlebotomy devices, catheters, catheter introducers, guide wire introducers, spinal and epidural, biopsy, apheresis, dialysis, blood donor, Veress needles, Huber needles, etc., and therefore, may incorporate a hub configuration other than a luer fitting.

Figure 20:
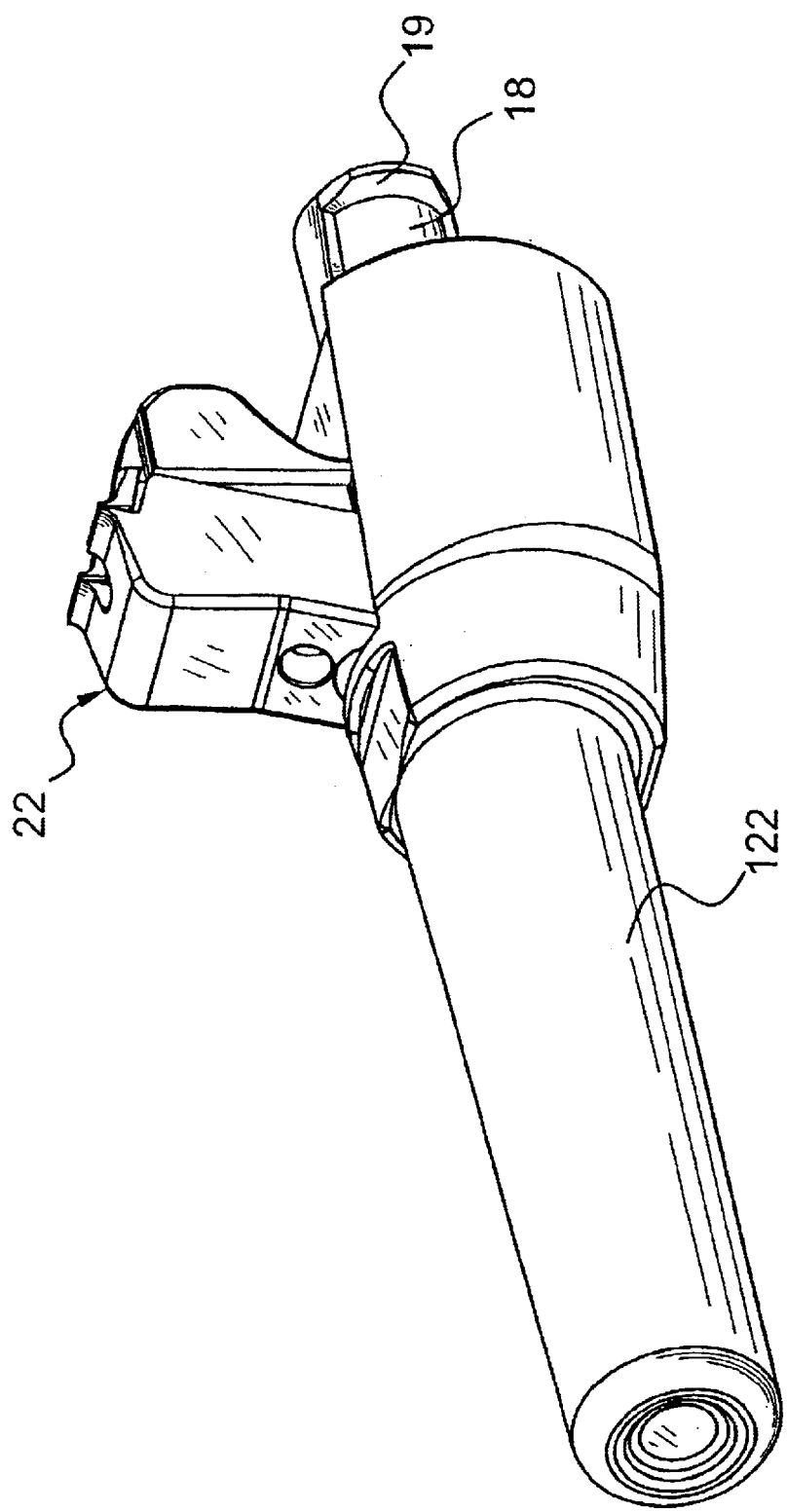
FIG. 20 is a perspective view of the safety shield apparatus illustrated in FIG. 1 with a sheath.
Figure 21:
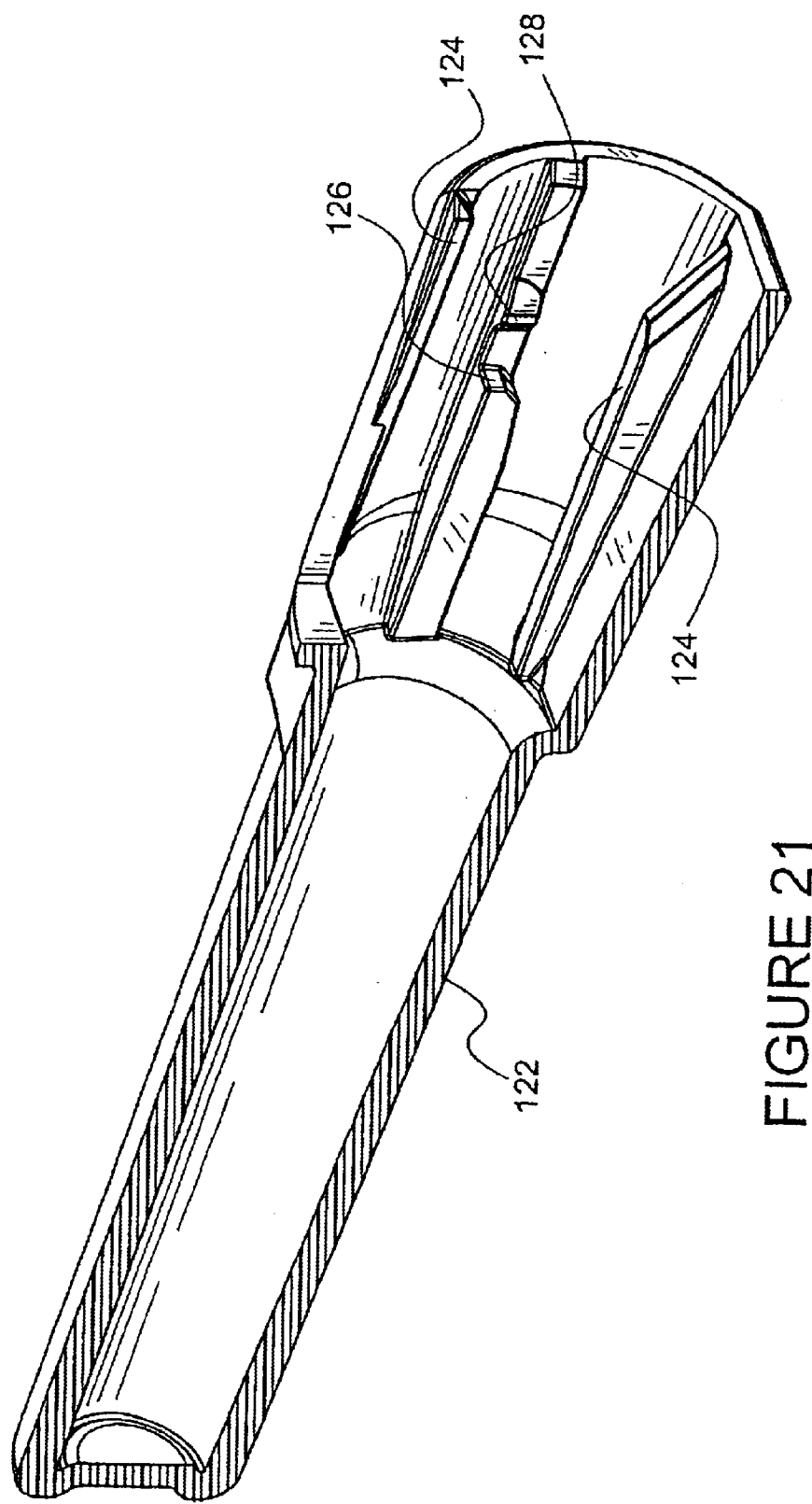
FIG. 21 is a rear perspective view, in part cross-section, of the sheath shown in FIG. 20.

The molded components of safety shield apparatus 10 including the hub 18, shield 22 and a sheath 122, described below with regard to FIGS. 20 and 21, are designed to be molded without the need for side-pull cores.

The distal end 24 of the needle 16 includes a bevel which may be aligned in a plane of symmetry with the shield 22 for indicating orientation of the bevel. The needle bevel may be oriented with respect to the retracted shield 22 to provide a consistent needle bevel configuration for a user. The shield 22 and hub 18 are connected through a bayonet-type snap fitment. A proximal end of shield 22 is received by a collar 61 of hub 18 wherein tabs, such as, for example, snaps 80 retain shield 22 to the hub 18 by interlocking with notches 70, as shown in FIGS. 6 and 7. Snaps 80 have a prong-like configurations. Snaps 80 may have other configurations, such as, for example, detents, clips, etc. It is contemplated that snaps 80 flexibly extend from shield 22 to engage an inner surface of collar 61 and resiliently project through notches 70 to interlock therewith. Collar 61 has a substantially cylindrical configuration. It is envisioned that collar 61 may have a variety of geometric configurations, such as, for example, rectangular, polygonal, etc. It is further envisioned that collar 61 may have various dimensions of length, diameter, width, etc.

Significant cost savings may result if a manufacturing mold is constructed from two simple plates which separate along a common axis and remain parallel to each other. In general, this requires that all part surfaces be formed by planes which form angles from ninety to one hundred eighty degrees with the mold parting surface; and if the part tapers, it should taper in such a manner as to get smaller in dimension proceeding along an axis into the mold cavity. This taper is referred to as "mold draft" and prevents the part geometry from being trapped in the mold geometry. This is commonly referred to as a "straight pull" mold.

Figure 9:
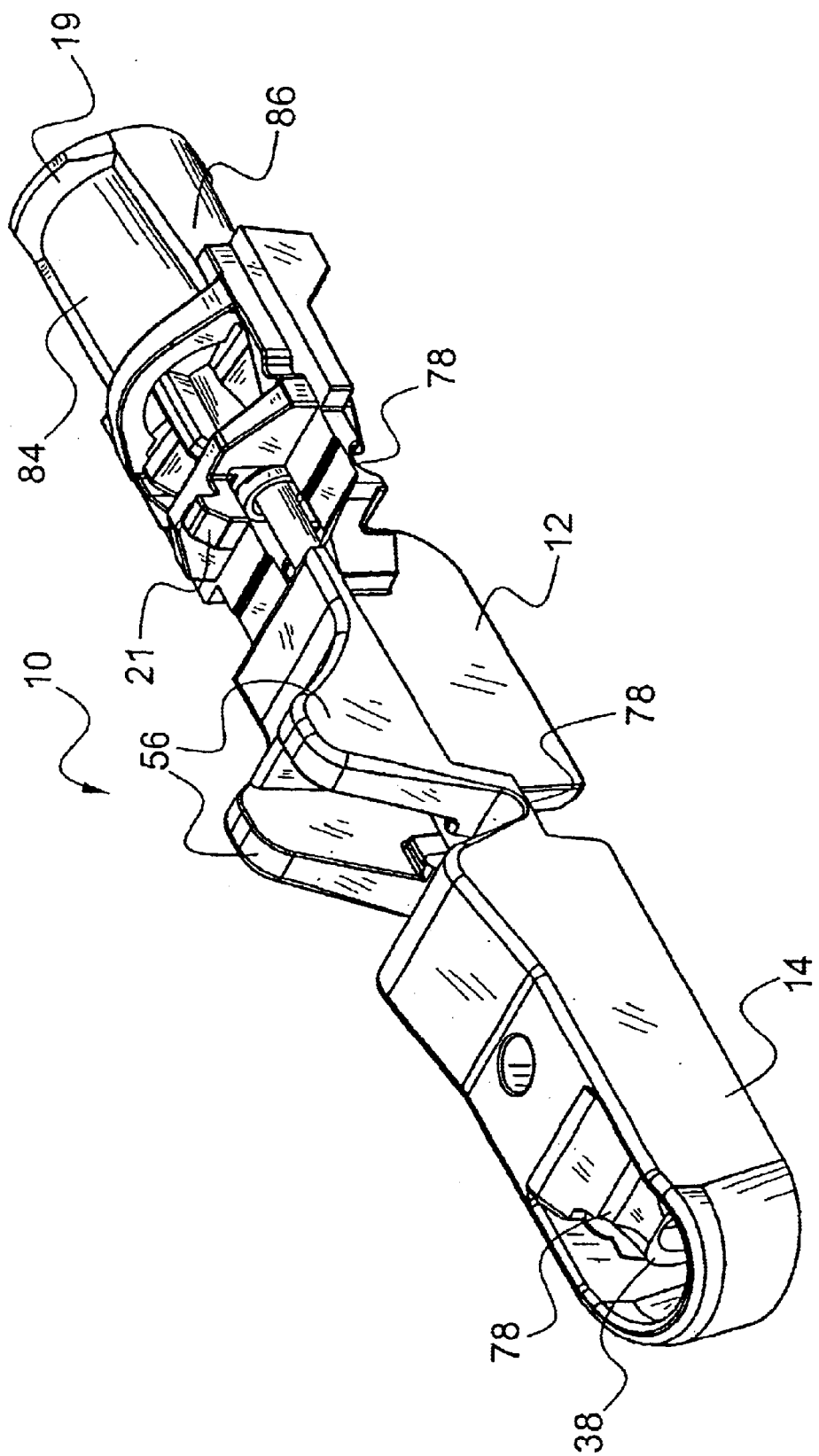
FIG. 9 is a perspective view of an alternate embodiment of the safety shield apparatus.
Figure 10:
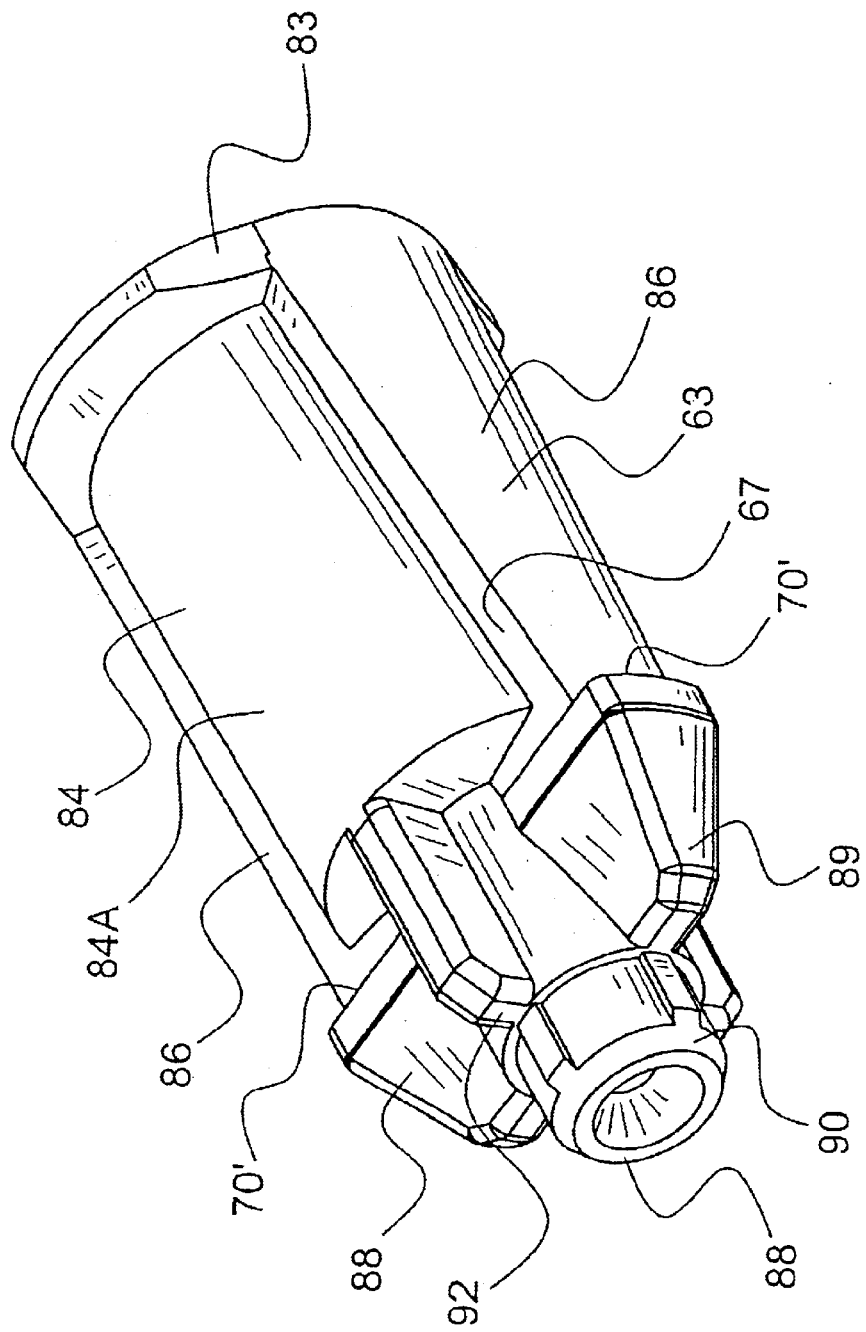
FIG. 10 is a perspective view of a hub of the safety shield apparatus illustrated in FIG. 9.

Notches 70 interlock with snaps 80 to form a snap fit component. Notches 70 are more difficult to mold in a straight pull fashion, since they may become trapped in the mold. Wedge features 76 and 86 provide for straight pull molding of this feature, while not adversely affecting the function of the luer fitting 19 or 83 (FIG. 10). Wedge features 76 and 86 (FIG. 9) provide this function through surfaces 63, which are parallel to the axis of the mold separation, and surfaces 67 which taper to form a seal or shutoff with the mating half of the mold surfaces 67 may also be parallel. Tapering or drafting of surfaces 63 in an expanding fashion should be avoided, which would cause interference with the lock ring of a standard syringe. Wedge features 76 and 86 allow the mold to form the latch feature, e.g., notches 70 and 70' (FIGS. 6, 7 and 10).

Figure 11:
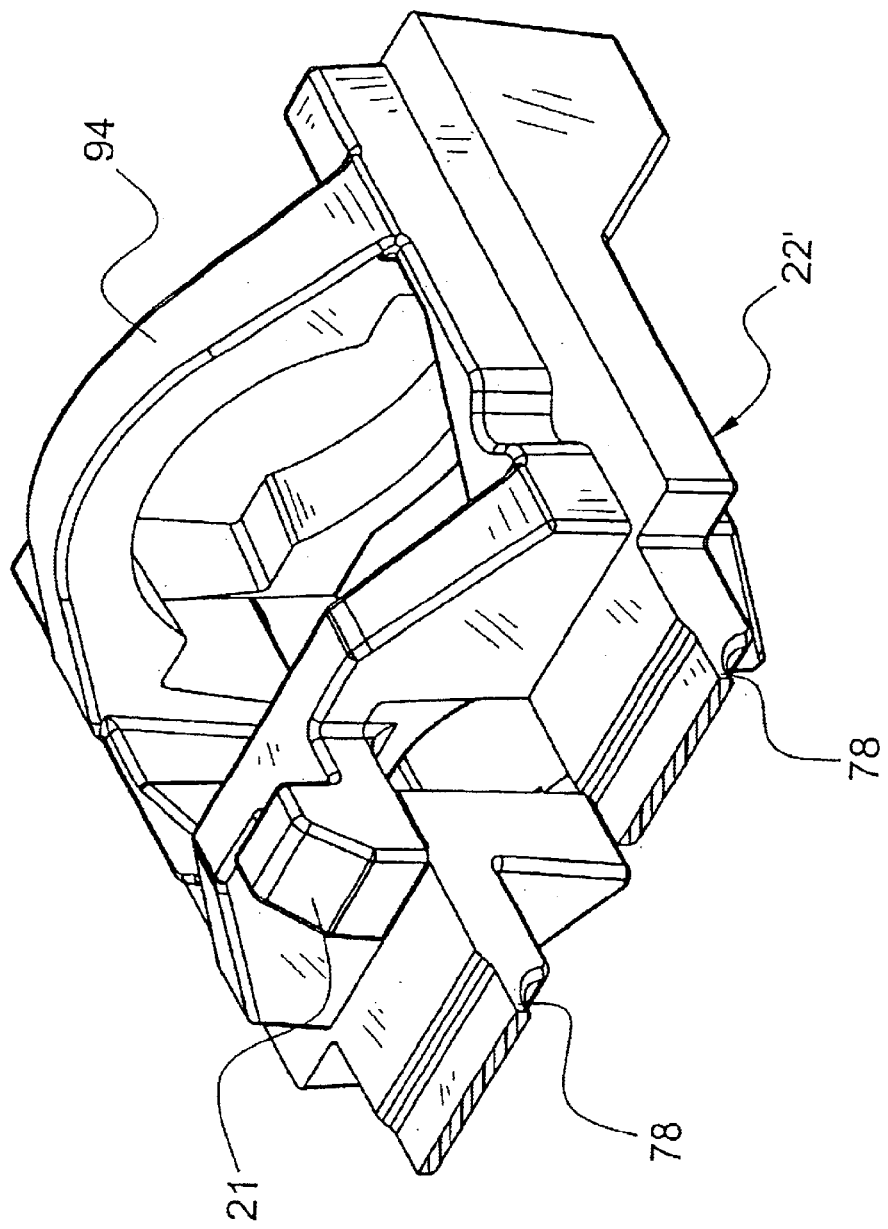
FIG. 11 is a perspective cutaway section of the safety shield illustrated in FIG. 9 showing an arched shield hub adapter.

Referring to FIGS. 10 and 11, an alternate embodiment is shown whereby wedge features 86 allow the manufacturing mold to form a latch feature including locking wings 88 with notch 70' and an arched shield adapter 94 configured for interlocking engagement. Locking wings 88 are disposed at a distal end of hub 84. Hub 84 includes an axial surface 84A having an arcuate configuration. Arched shield adapter 94 is configured for receipt of axial surface 84A. Abutment surface 92 abuts against the arched shield adapter 94 for proper aligning of the hub 84 to the shield 22'. It is contemplated that axial surface 84A and adapter 94 may have various corresponding configurations, such as, rectangular, etc.

A retention catch 21, formed on the proximal end of shield 22, releasably latches with proximal segment 12 to hold the shield 22 in a fully retracted position for use. Proximal segment 12 has a surface which slides over retention catch 21 and is retained thereby in a latching or catch configuration. It is contemplated that retention catch 21 may engage various portions of proximal segment 12. It is further contemplated that shield 22 may be retained by multiple detents or retention catches of the proximal end of shield 22. Other latching configurations are also envisioned such as, for example, pins, clips, etc. Shield 22 may also be held in the retracted position via engagement with hub 18.

The shield 22 is manually extended and locked in a single-handed manner following use by either: 1) pushing the shield 22 with a finger, for example at raised surface 56 (FIG. 9); or 2) surface activation by, for example, pushing the shield 22 against a surface such as a tabletop. Referring to FIGS. 1–3, surface activation is enabled due to the configuration of shield 22 such that proximal segment 12 and distal segment 14 form a general fulcrum point 13 engageable to extend shield 22 to the extended position. Fulcrum 13 includes a hinge portion projecting from shield 22 that engages the table, etc. It is contemplated that fulcrum 13 may include hinge portions, such as, living hinges, pinned hinges, etc. This surface activation configuration advantageously facilitates one-handed operation and does not require the above-discussed finger actuation.

Figure 4:
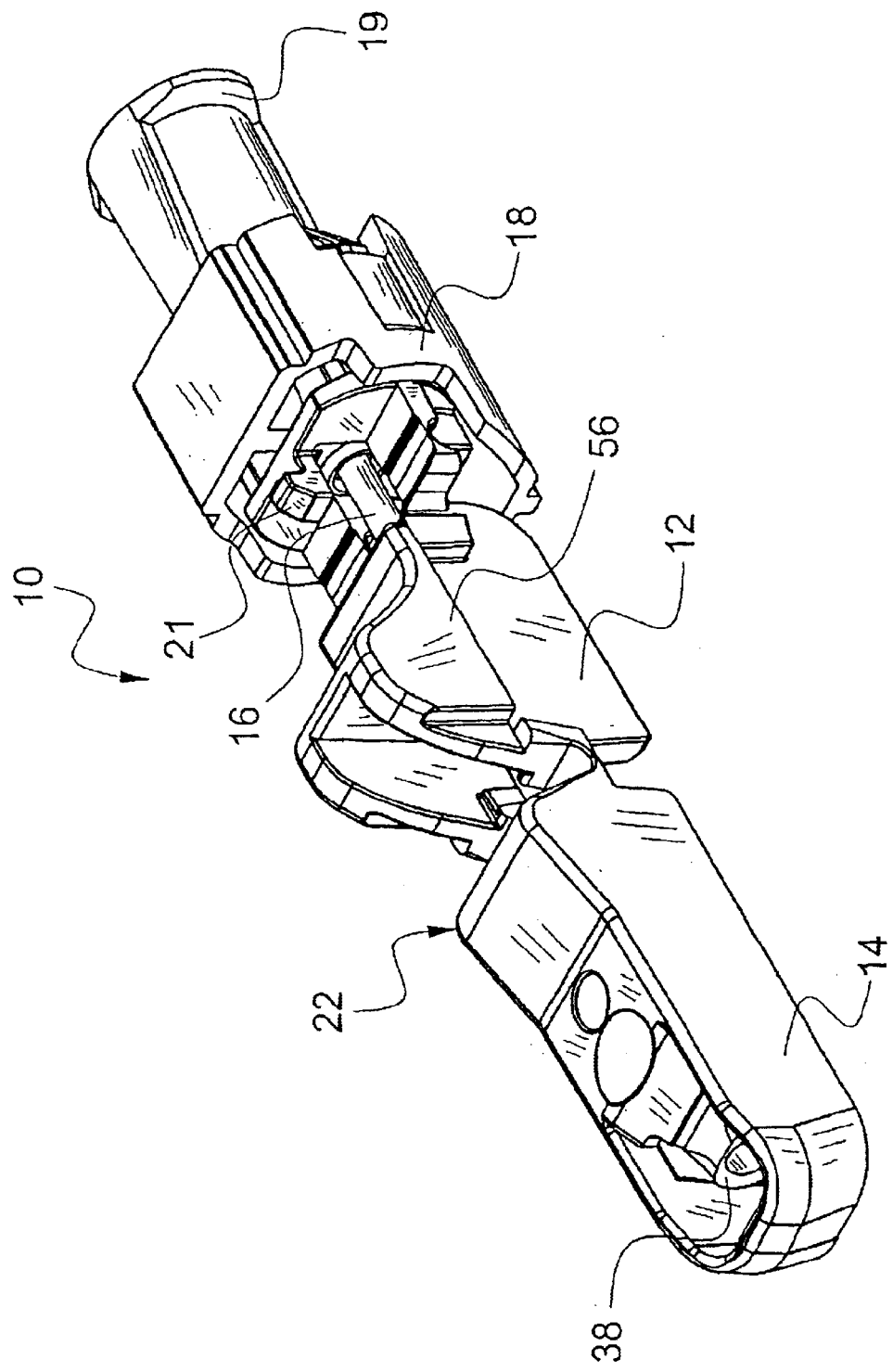
FIG. 4 is a perspective view of the safety shield apparatus illustrated in FIG. 1 fully extended.
Figure 5:
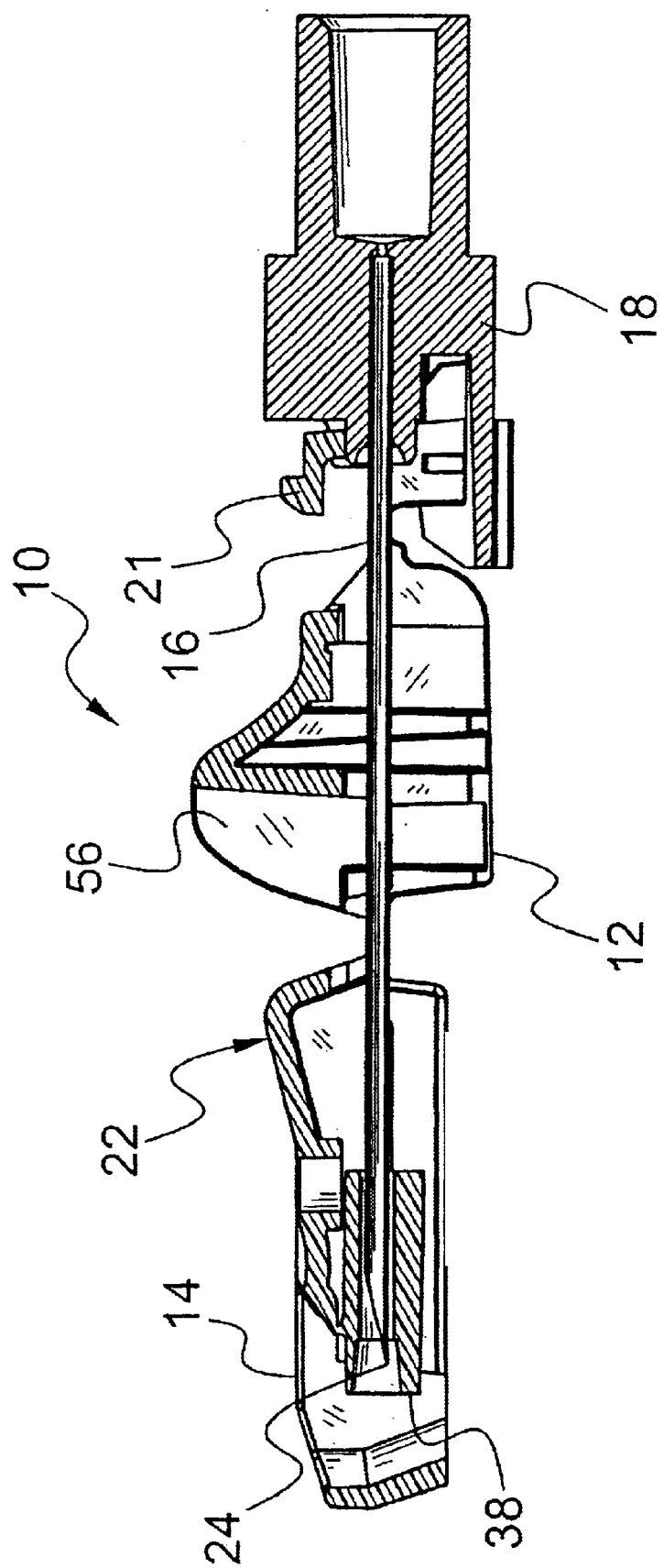
FIG. 5 is a cross-sectional view of the safety shield apparatus shown in FIG. 4.
Figure 8:
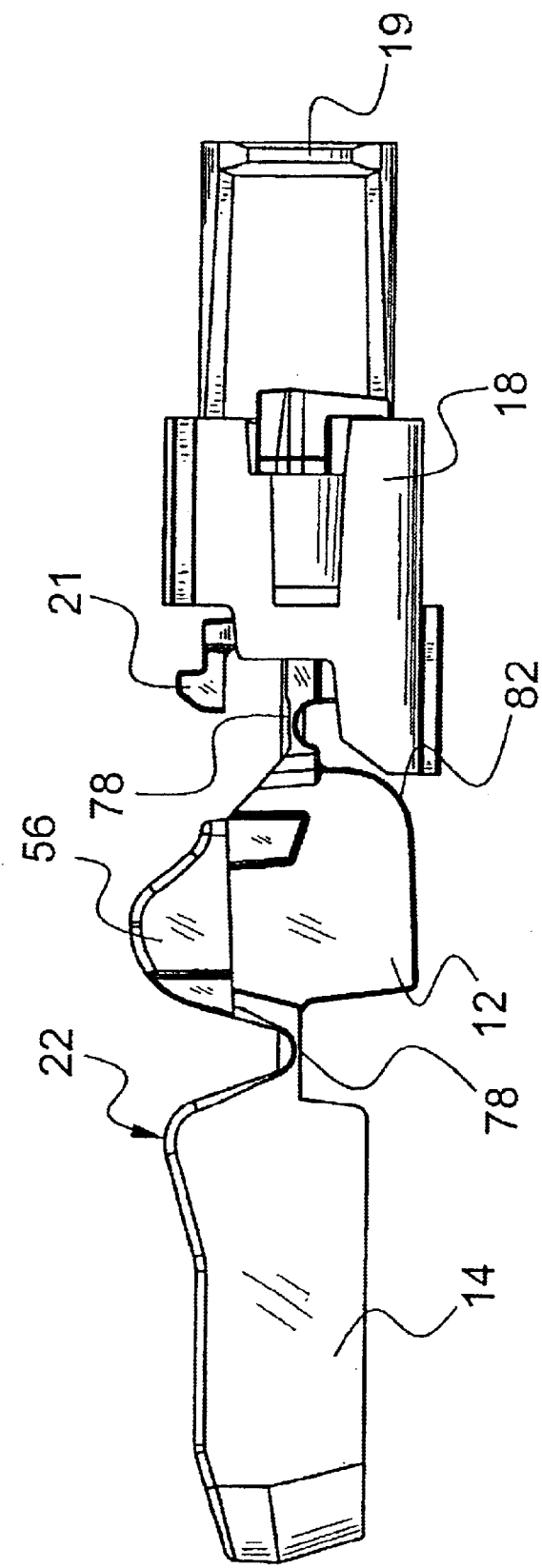
FIG. 8 is a side view of the safety shield apparatus illustrated in FIG. 1.

Referring to FIGS. 1, 3 and 4, shield 22 is extendable from a retracted position (FIG. 1) to an extended position (FIG. 4). The shield 22 irreversibly locks around the needle 16 upon full extension to protect the user from inadvertent exposure to the needle point 24.

Referring to FIGS. 6–10, a surface, such as, for example, an over-travel stop 62 on the hub 18 contacts surface 82 on the proximal segment 12. Stop 62 limits rotation of proximal segment 12 relative to hub 18 to advantageously preclude excess bending of the needle 16 during and after full extension of the shield 22 to the needle 16. Stop 62 extends from hub 18 forming a planar edge configured to engage shield 22, thereby limiting rotation of proximal segment 18 and consequently, needle 16. It is contemplated that stop 62 may have various configurations for engaging shield 22, such as, for example, staggered, stepped, interlocking, offset, etc. It is further contemplated that the over-travel stop may be formed with shield 22. It is envisioned that stop 62 limits undesirable rotation of shield 22, such as, for example, over-rotation, rotation that causes plastic deformation of needle 16, etc.

Collar 61 provides for convenient and safe grasping of the hub. This ergonomic feature of the present disclosure advantageously provides a surface that attracts users to grasp collar 61 for syringe removal, etc. It is envisioned that hub 18 may include other ergonomic features such as color coding. Surfaces 64, 66 and 89, 90 provide for guiding the hub 18 into the correct position with the shield 22. The shield 22 abuts against the hub 18 at surface 71 when in the retracted position.

Figure 12:
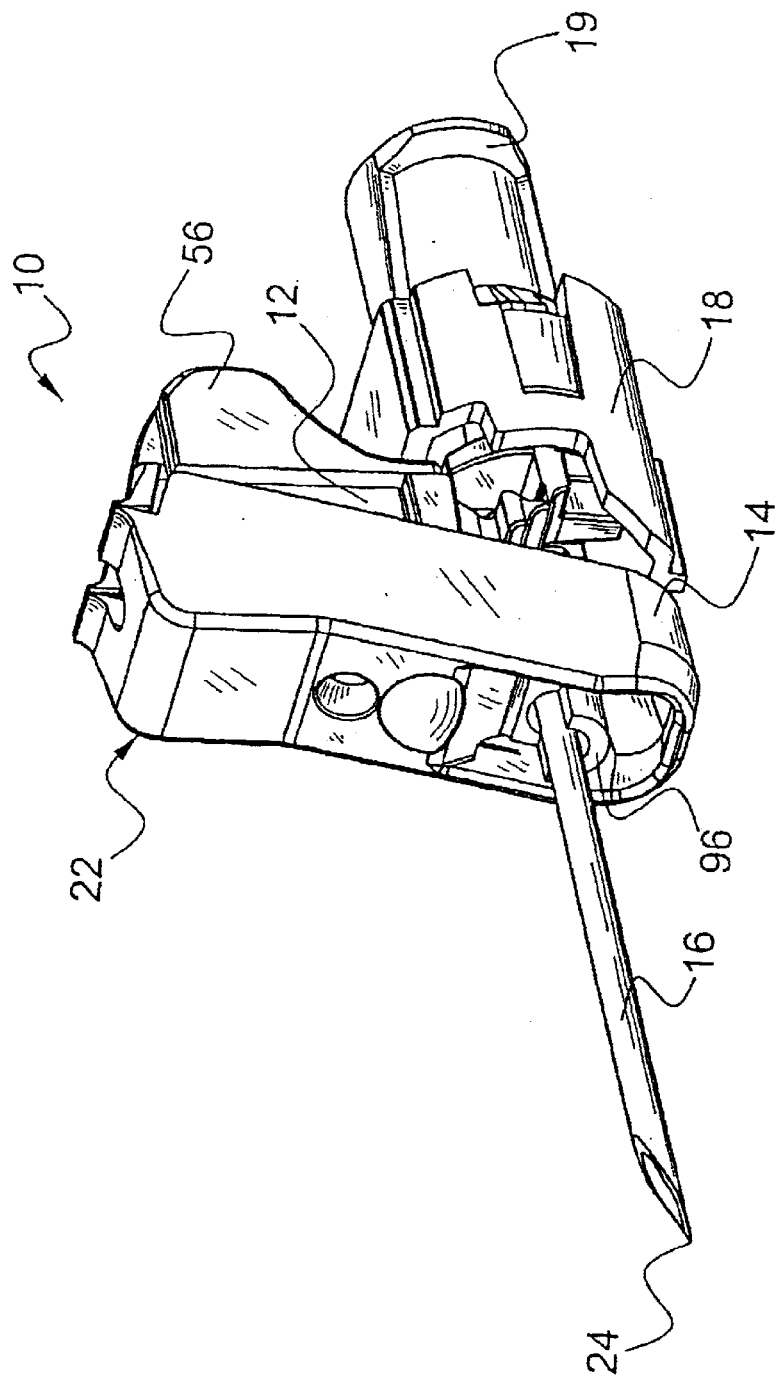
FIG. 12 is a perspective view of the safety shield apparatus illustrated in FIG. 1 showing an alternate embodiment of a linear bearing.
Figure 12A:
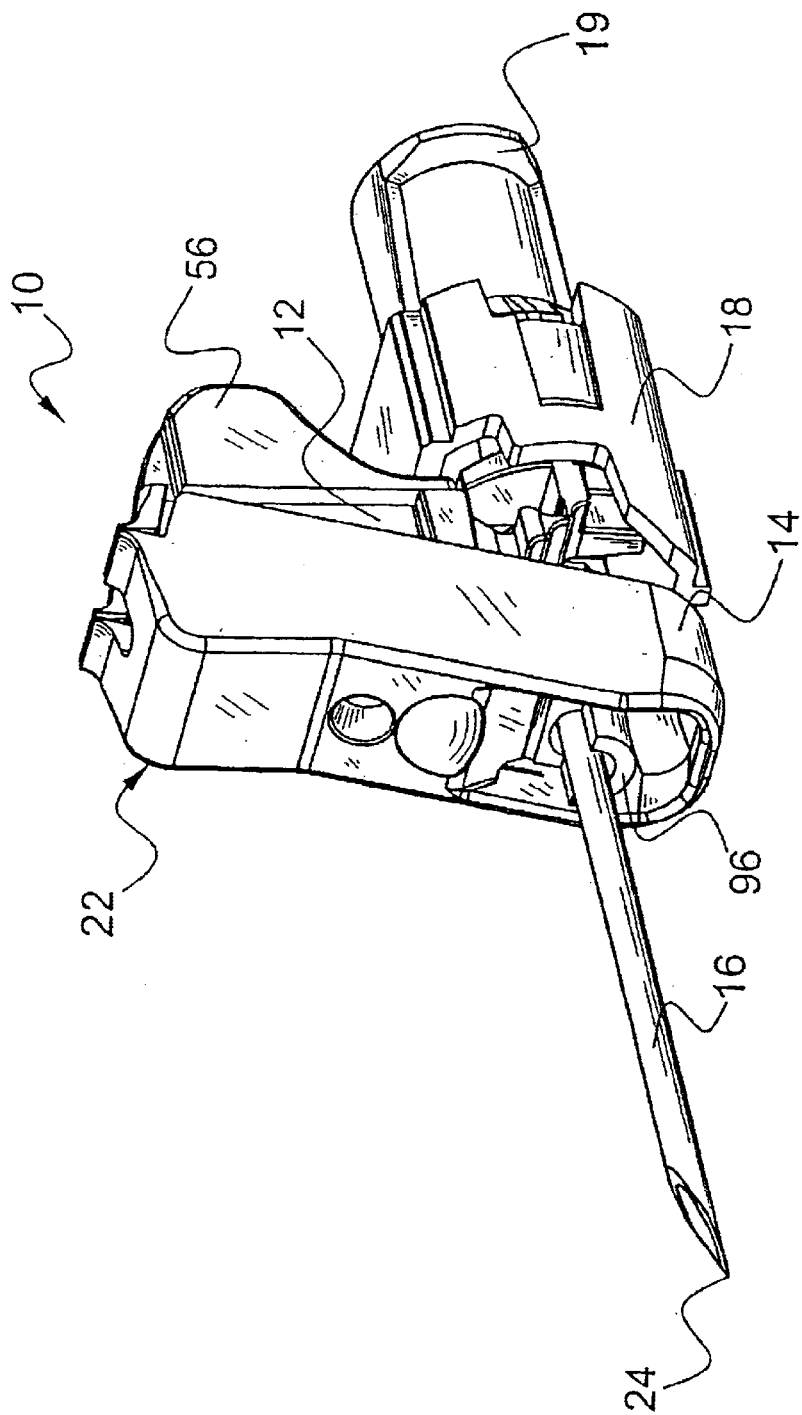
FIG. 12A is a perspective view of the safety shield apparatus illustrated in FIG. 1 showing an alternate embodiment of a linear bearing.
Figure 12B:
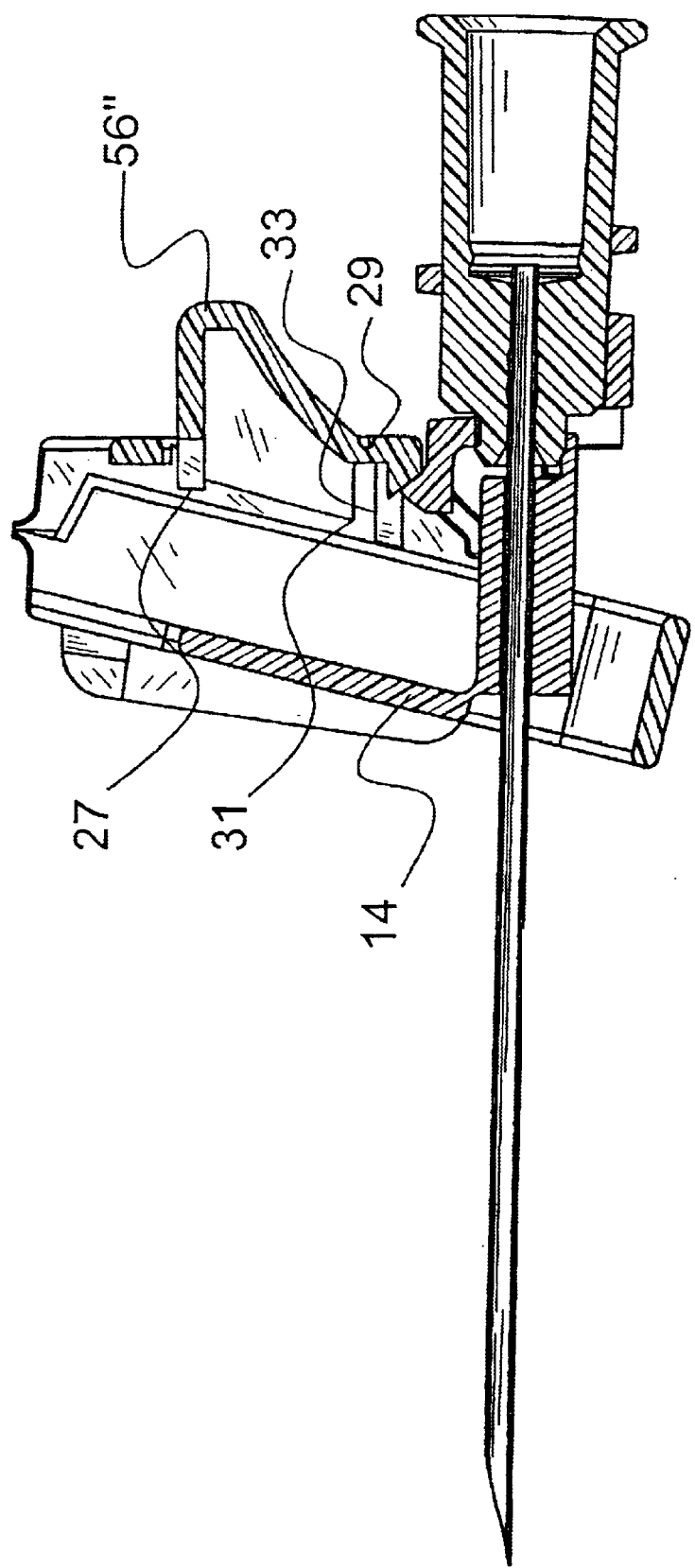
FIG. 12B is a cross-sectional view of the safety shield apparatus illustrated in FIG. 1 having an articulating button.
Figure 12C:
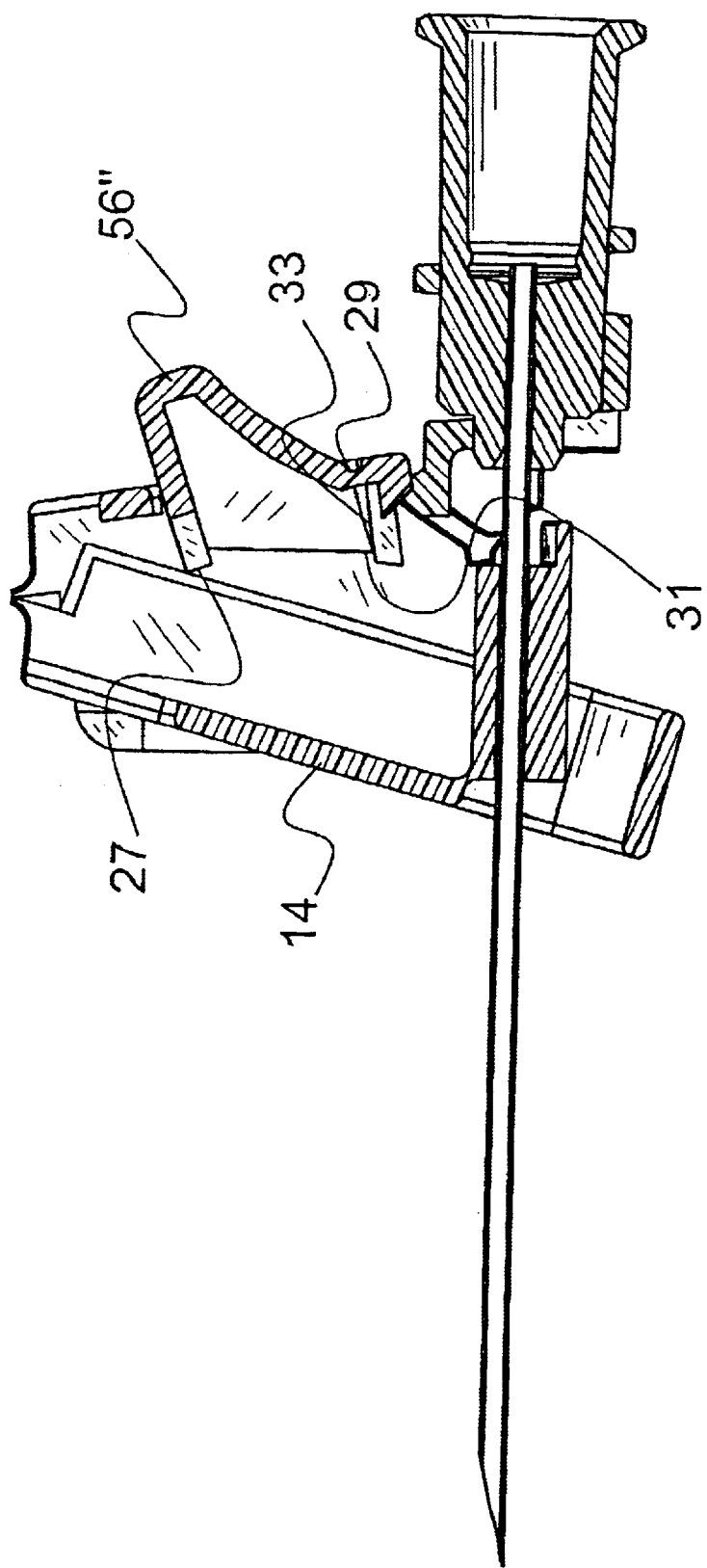
FIG. 12C is a cross-sectional view of the safety shield apparatus illustrated in FIG. 12B.

In an alternate embodiment, the raised surface 56 (FIG. 12A), as an aid in urging the shield 22 to the extended position may be further configured to form an articulating actuator 56" as shown in FIGS. 12B and 12C. The articulating actuator 56" may pivot about a hinge 29 and may further be biased in such a way as to maintain the articulating actuator 56" in a relaxed position (FIG. 12B). During actuation, the actuation force on the articulating actuator 56" acts directly upon a segment other than the proximal segment 12 (the distal segment 14 in FIG. 12C) at contact surface 27, thereby, enhancing advancement of the shield 22. Stop surfaces 31 and 33 may be provided between the articulating actuator 56" and its segment to prevent over-travel of the articulating actuator 56".

Figure 13:
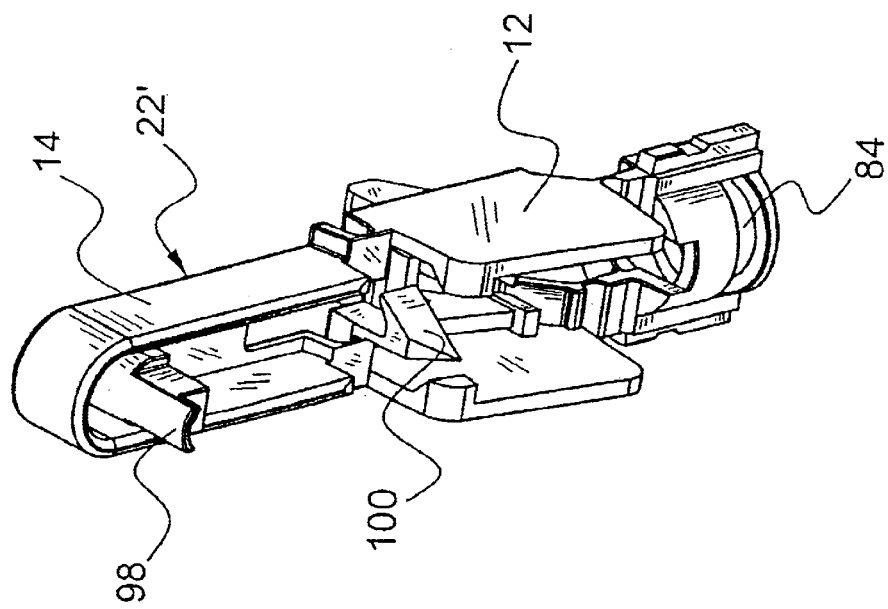
FIG. 13 is a perspective view of an underside of the safety shield apparatus illustrated in FIG. 9 showing a barbed flap lock.

Referring back to FIGS. 1–5, a linear bearing 38 is hingedly disposed within the distal segment 14 and slides linearly along the needle 16 as the distal segment 14 translatably rotates along the needle 16 when the shield 22 is extended from the retracted position to the extended position. The linear bearing 38 shields the distal end 24 of the needle 16 when the shield 22 is in the extended position. Linear bearing 38 fully covers distal end 24 to provide an increased perception of security and minimization of fluid splatter when the shield is extended and locked. Referring to FIG. 12A, an alternate embodiment illustrates a duckbill-type linear bearing 96, which allows the distal end 24 of the needle 16 to be visible through the top of the shield 22. This configuration also beneficially provides point protection perception to a user. Referring to FIG. 13, another alternate embodiment illustrates a flap 98, employable with linear bearing 38 or 96, for aligning the linear bearing 38 or 96, during assembly.

Figure 14:
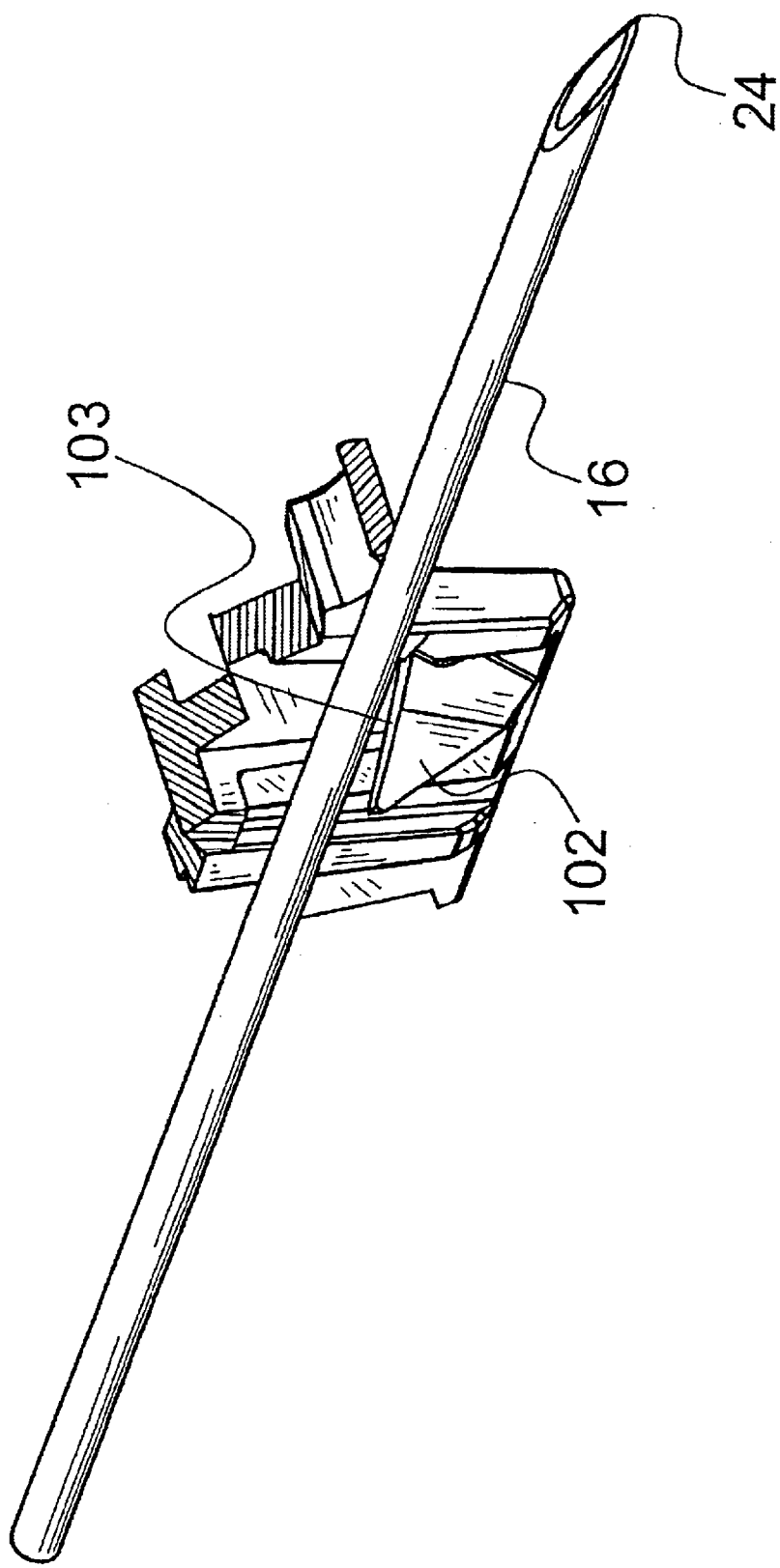
FIG. 14 is a cutaway view of an alternative embodiment of a flap lock securing a medical needle of the safety shield apparatus illustrated in FIG. 13.

Referring to FIG. 13, safety shield apparatus 10 has a barbed flap lock 100, which snaps around the needle 16 when the shield 22 is fully extended to lock shield 22 and retain needle 16 in a protective configuration providing security for a user from accidental needle stick. Referring to FIG. 14, an alternate embodiment shows an angled flap lock 102 that is advantageous for a wide range of needle 16 sizes to capture small gage needles and larger gage needles. The angled flap lock 102 easily flexes to facilitate needle 16 capture. The bottom edge of the angled flap lock 102 is angled to drive the needle 16 in toward the root of the angled flap lock 102 when the needle 16 is pulled back against the angled flap lock 102. This results in a lock with a light locking force and considerable retention force. Further, flap lock 102 has a reduced mass, facilitating placement within smaller spaces. This configuration makes flap lock 102 difficult to defeat, precluding easy reset. The angled flap lock 102 is also advantageous in its ability to limit movement of the needle 16 relative to the shield 22 due to the interaction of the flat lower surface 103 of the angled flap lock 102 with the needle 16 in the latched condition.

Figure 15:
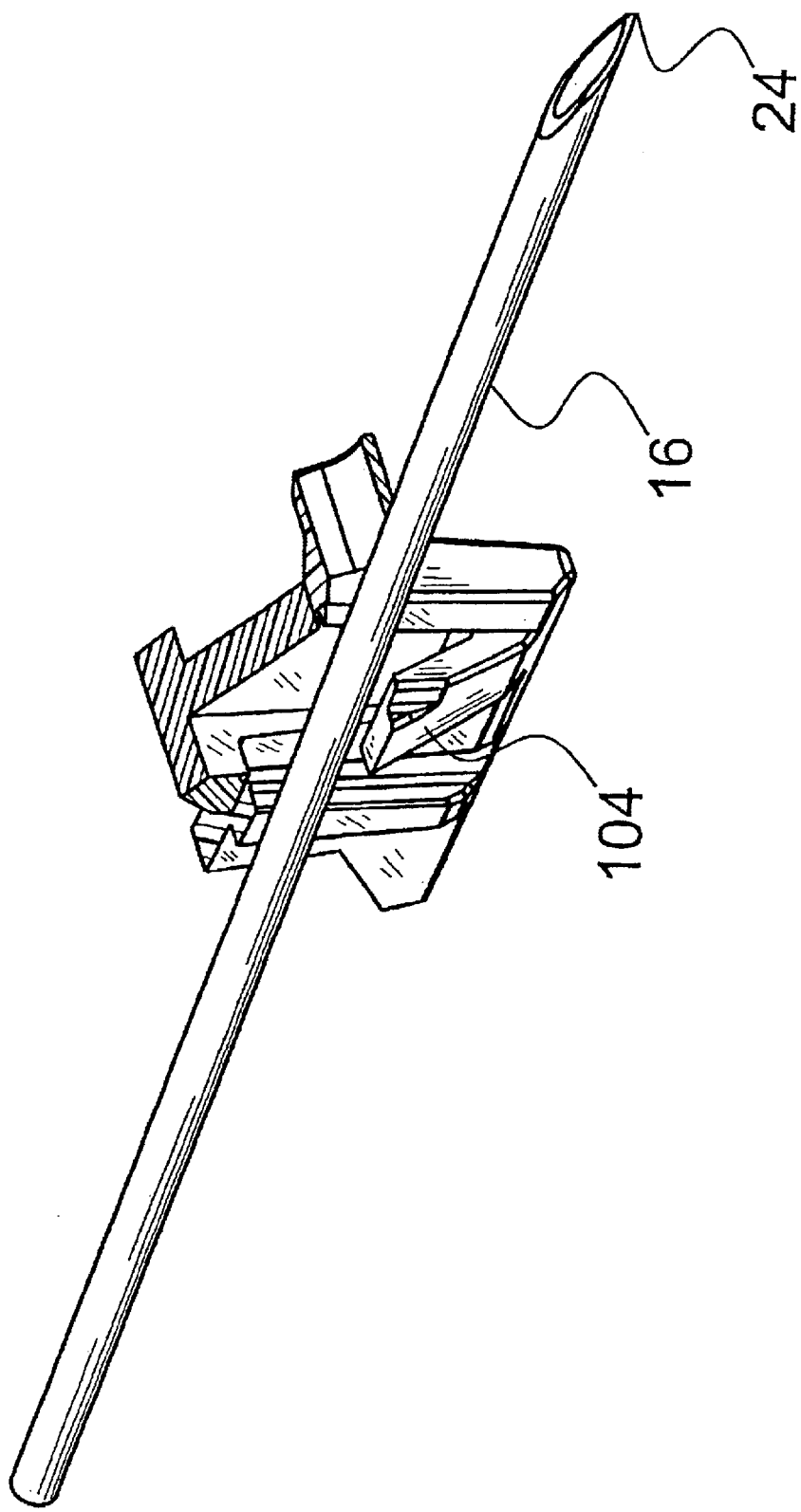
FIG. 15 is a cutaway view of an alternate embodiment of the lock of the safety shield apparatus illustrated in FIG. 13.
Figure 15A:
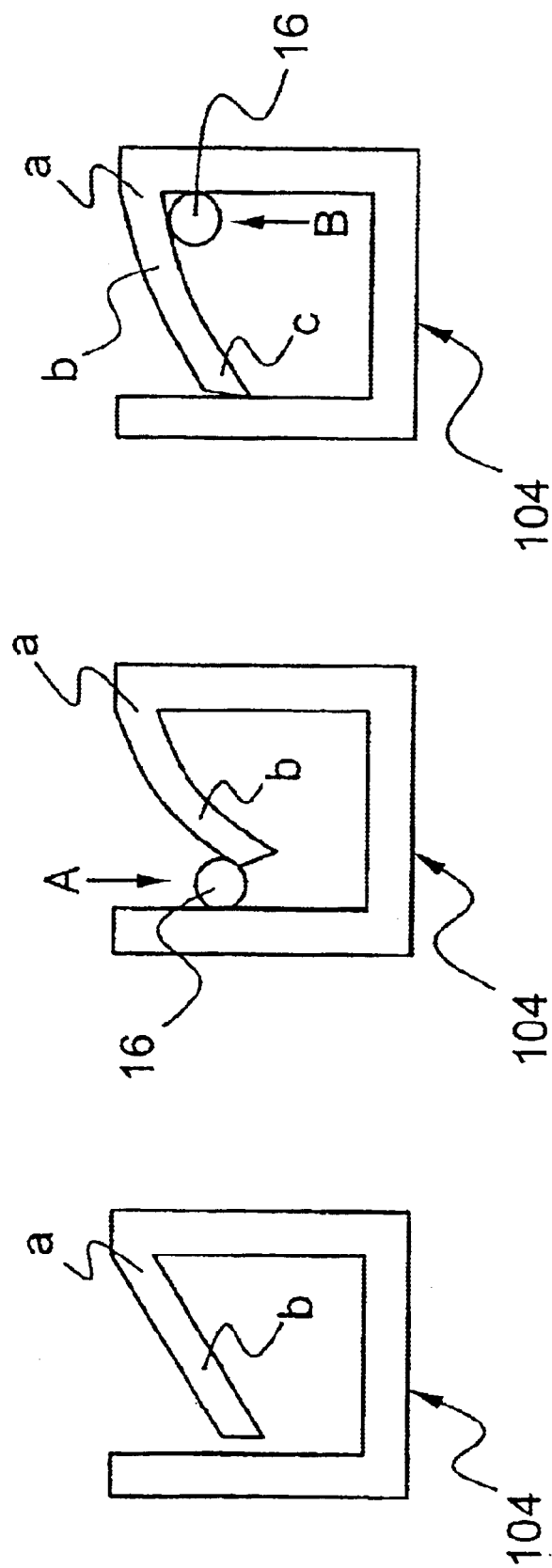
FIG. 15A is a plan view of operation of a rectangular lock.

In an alternate embodiment, the needle lock includes a rectangular flap lock 104 as shown in FIGS. 15 and 15A. The rectangular flap lock 104 is configured to lock with low latching forces for small gage needles, while maintaining robust retention forces for larger gage needles. The rectangular lock comprises an angled rectangular flap lock 104 molded as part of one side of the shield 22. The rectangular flap lock 104 is designed to flex inward toward an attachment point a upon needle 16 engagement with lock arm b, as shown by arrow A. The needle 16 is forced back to the root (attachment point a) of the rectangular flap lock 104 when pulled back against lock arm b of the rectangular flap lock 104, as shown by arrow B. As the pullback force increases, the lock arm b of rectangular flap lock 104 may deflect until a free end c of the rectangular flap lock 104 contacts the wall opposite the root of the rectangular flap lock 104. This effectively supports the latch in two places: the root and the contact point of free end c with the opposite wall. The end result is a lock that has relatively low engagement forces and substantial retention forces. The thickness of lock 104 is reduced adjacent attachment point a relative to lock arm b. This configuration advantageously minimizes bending of needle 16, and facilitates placement within smaller spaces making flap lock 104 difficult to defeat, precluding easy reset.

Figure 16:
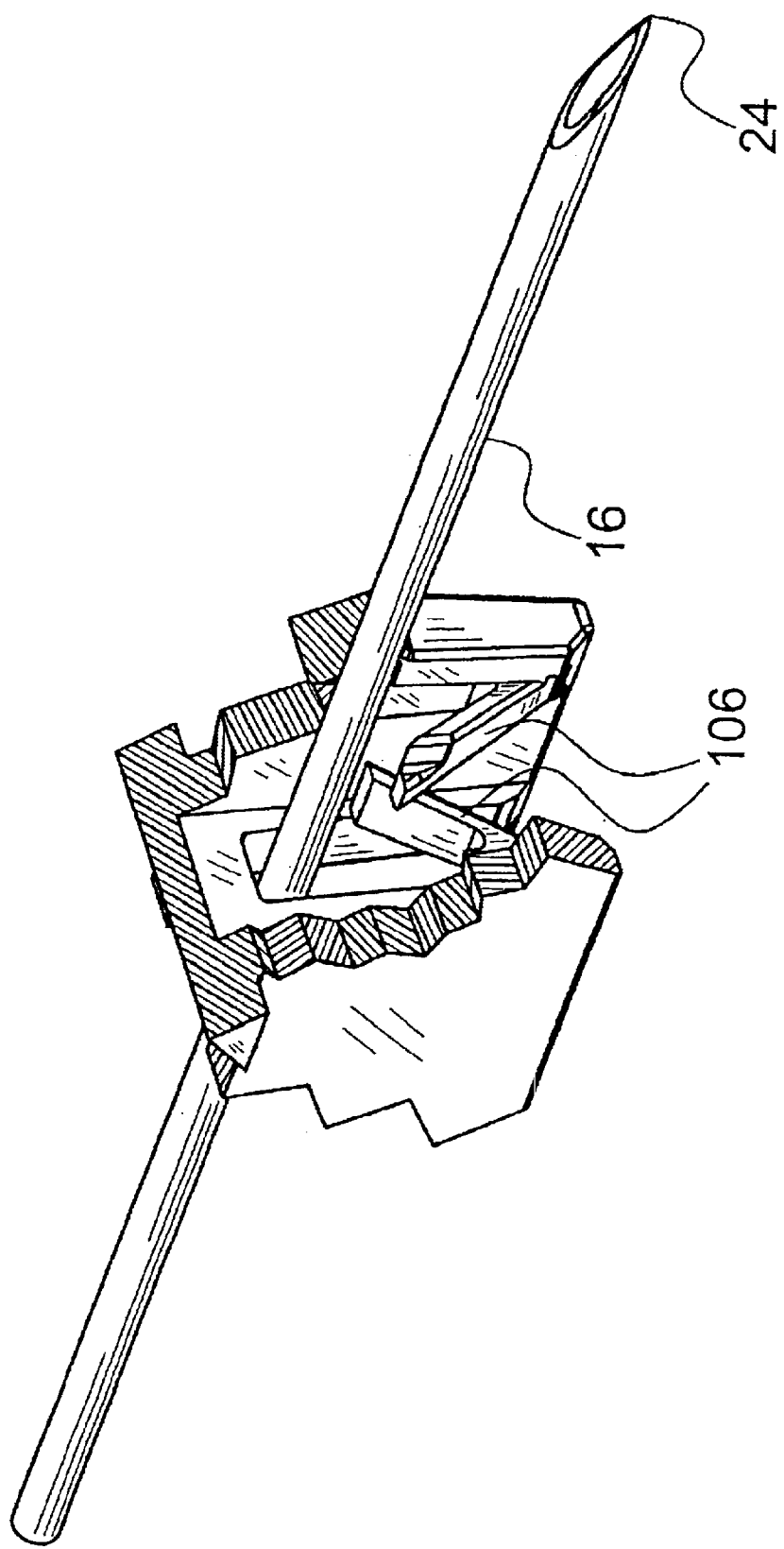
FIG. 16 is a cutaway view of an alternate embodiment of the lock of the safety shield apparatus illustrated in FIG. 13.

In another embodiment, the needle lock is a double flap lock 106 as shown in FIG. 16. This lock configuration consists of two rectangular locks, each attached to opposite walls on the shield 22. This lock substantially increases the difficulty in manually defeating the lock, advantageously precluding reset because both locking flaps of the double flap lock 106 must be defeated simultaneously to reset the lock.

Figure 17:
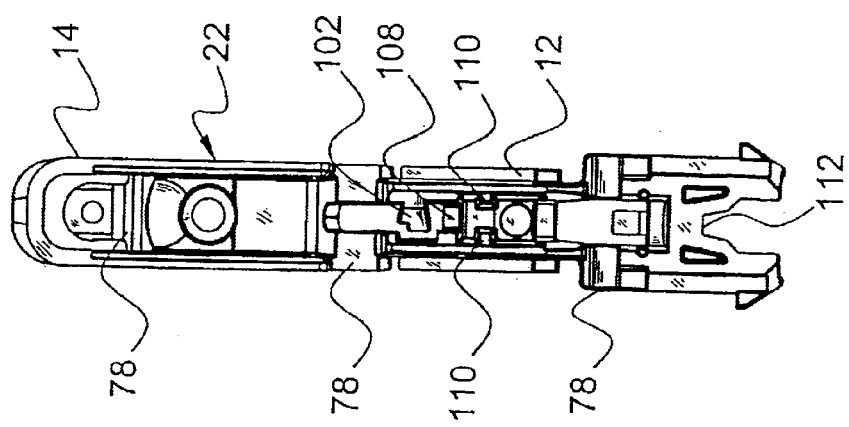
FIG. 17 is a view of the underside of the safety shield apparatus illustrated in FIG. 7.

Additional features may be added to the locks of the present disclosure to increase the difficulty in manually defeating the needle locks and thereby preclude easy reset. For example, referring to FIG. 17, one or more stiffening ribs 110 may be added to either side of the lock to minimize finger contact with the locking flap and to stiffen the shield 22 walls to make wall deflection more difficult. A stiffening arch 108 may be added to minimize shield 22 wall spreading and to make direct finger tip access to the lock more difficult. Moreover, for example, by rotating the angled flap lock 102 so as to place the free end of the angled flap lock 102 away from the living hinge 78 (at the end of the distal end of proximal segment 12), the potential for fingertip access to the angled flap lock 102 is minimized.

The hinges connecting segments 12 and 14 may be flexible living hinges 78, pinned hinges, or equivalents thereof that provide for hinged connections of the segments 12 and 14. However, the number of hingedly connected segments depends upon the needle 16 length and device length required to extend the shield 22 beyond the distal end 24 of the needle 16. For example, alternate embodiments of the present disclosure, illustrated in FIGS. 29–36, similar to that described with regard to FIGS. 1–22, comprise four segments which are for long needle applications including, but not limited to, angiographic needle applications such as guide wire introducers, blood donor, apheresis, dialysis, spinal and epidural and so forth. The present invention may be injection molded using polypropylene, other synthetic resinous materials, or equivalents thereof that provide for fabrication of living hinges 78.

Figures 17A, 17B, 17C:
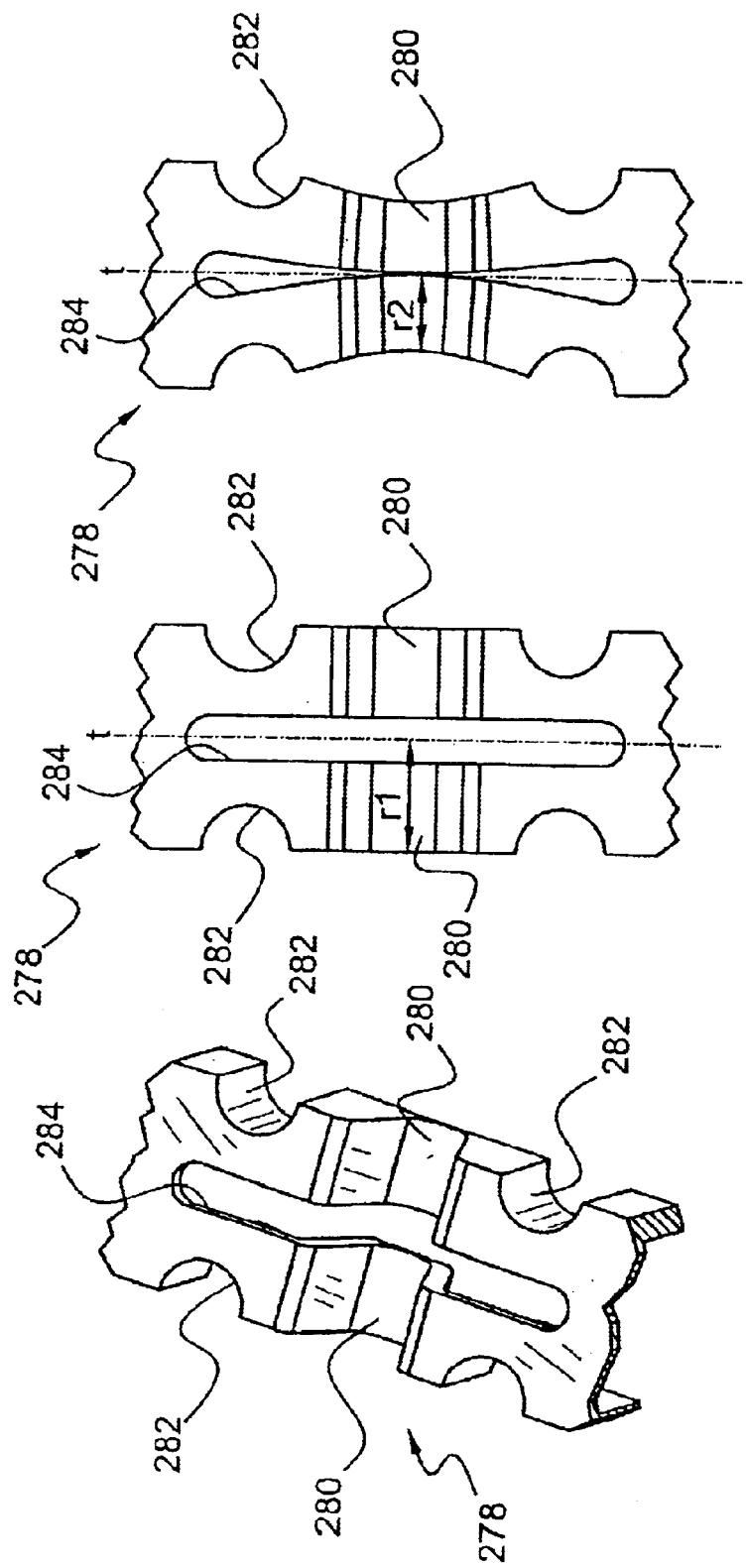
FIG. 17A is a partial cross-sectional view of a hinge component of the safety shield apparatus in accordance with the present disclosure.
FIG. 17B is a cutaway plan view of the hinge component of FIG. 17 without the application of stressing forces.
FIG. 17C is a cutaway plan view of the hinge component of FIG. 17 with the application of stressing forces.

Referring to FIGS. 17A–17C, in an alternate embodiment, living hinges 278 may provide hinged connections for segments 12 and 14 of shield 22 and hub 18. The areas around living hinges 278 are relieved by relieved portions, discussed below, to enable living hinges 278 to flex inward toward needle 16 when shield 22 is rotated in torsion, such as, for example, by twisting. Living hinge 278, which can be disposed between the segments and/or the hub, has a pair of hinge straps 280 that extend between the members being hinged. It is contemplated that one or a plurality of hinge straps 280 may be employed.

The relieved portions include crumple zones, such as, for example, relief portions 282 and 284. Relief portions 282 are formed on opposing sides of living hinge 278 in an outer surface thereof. It in envisioned that one or a plurality of relief portions 282 may be used. Relief portion 284 is formed within living hinge 278 as a cavity extending along the longitudinal length thereof. Relief portion 284 may be variously configured according to geometry, dimension, etc., in accordance with the principles of the present disclosure and suitability for a particular medical needle application. Relief portions 282 and 284 are configured to cause living hinges 278 to flex inward for accommodating greater amounts of stress due at least in part to torsion, prior to failure, such as, for example, plastic deformation, fracture, etc., as will be discussed.

Referring to FIG. 17B, the stress in living hinge 278 including hinge straps 280 at any given point is in direct proportion to a distance, such as, for example, a radius r1 of that point from an axis t of torsion. Consequently, the greatest amount of stress is at the outermost edges of hinge straps 280. Prior to application of torsion, e.g., twisting of living hinge 278, the stress on hinge straps 280 is approximately zero. As living hinge 278 is twisted, a stress is created in hinge straps 280. Referring to FIG. 17C, reliefs 282 and 284 facilitate hinge strap's 280 move closer to axis t such that the distance from axis t, r2, is reduced, thereby reducing the stress at r2, in accordance with that described above. This configuration advantageously increases the amount of rotational deflection necessary to cause hinge failure in torsion due to twisting. Further, an indication of failure is provided to a user. Alternatively, to increase the amount of twisting necessary to cause the living hinges 78 of the actuated device to fail, support structures 25 (FIG. 3) in the form of thin plates in a plane perpendicular to the plane of the hinges 78 may be added. These support structures 25 may take the form of living hinges, but are not limited to such forms.

Figure 18:
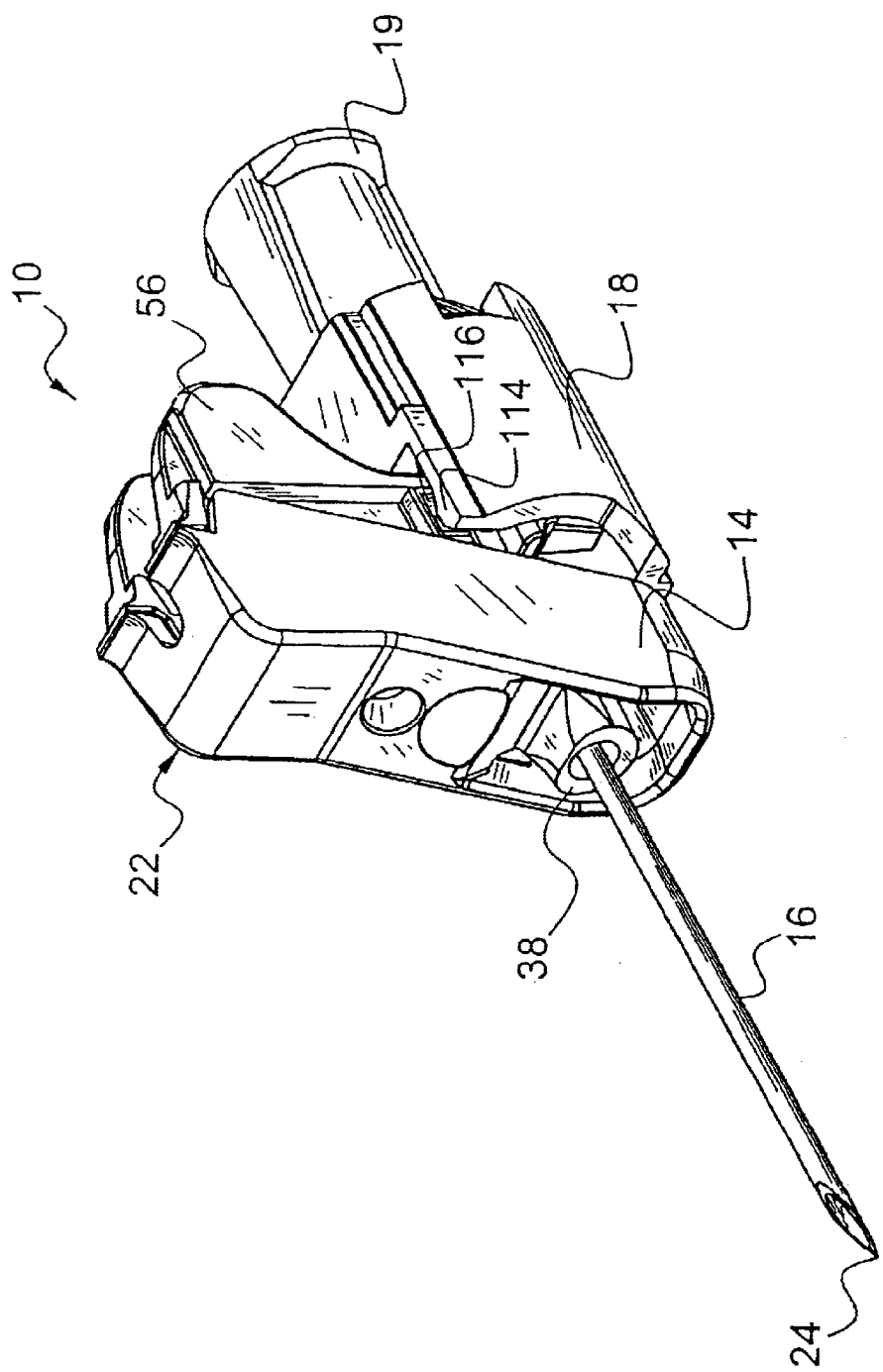
FIG. 18 is a perspective view of an alternate embodiment of the safety shield apparatus.

As shown in FIG. 18, a collar clip detent 114 may be added to the hub 18 that engage a recessed area 116 for retaining the shield 22 in the retracted state. An alternate embodiment may be a detail on the shield 22 that slides under the hub collar (not shown).

Figure 19:
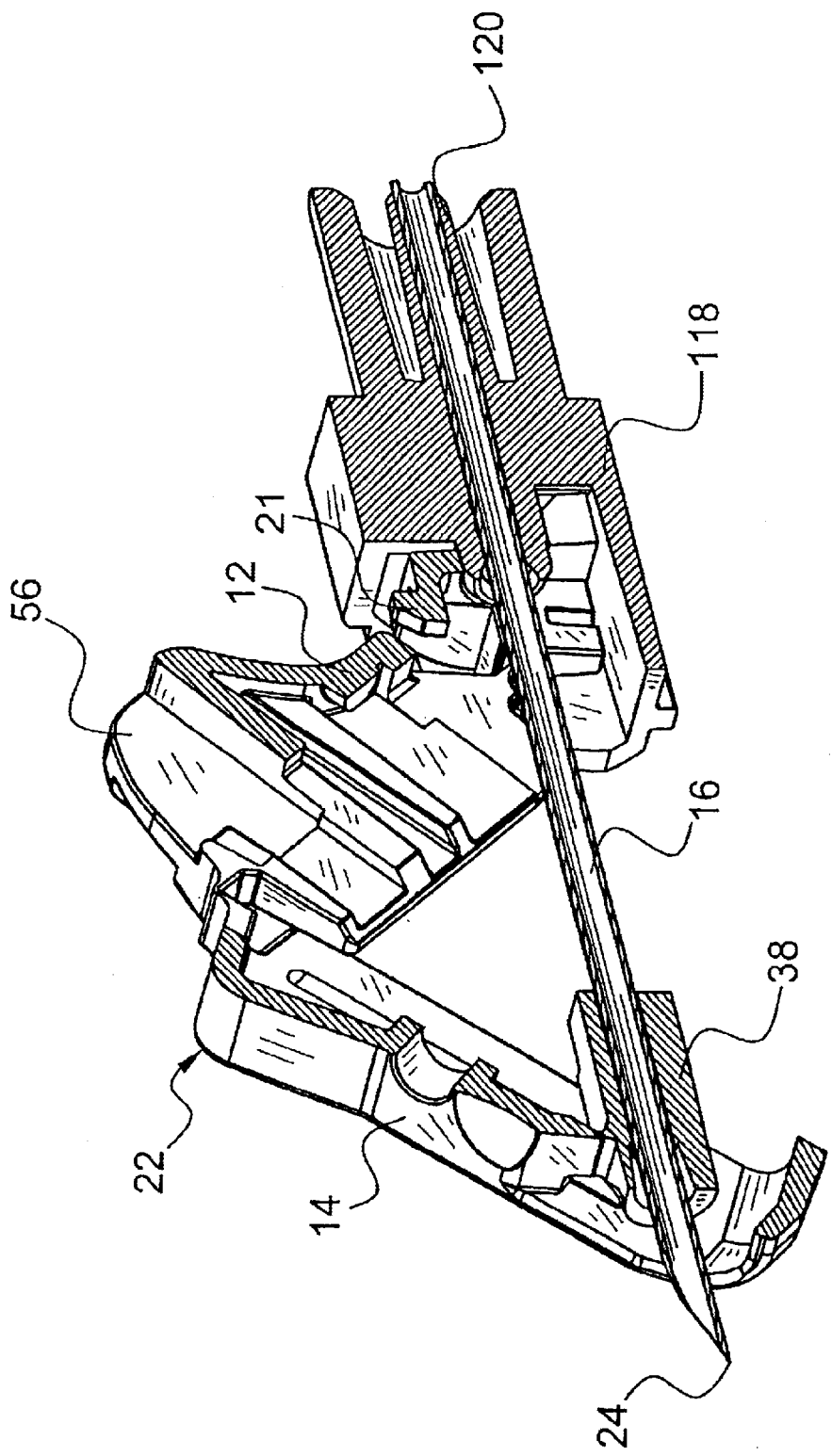
FIG. 19 is a cross-sectional view of an alternate embodiment the safety shield apparatus.

In an alternate embodiment, FIG. 19 illustrates a hub 118 having an extended needle enclosure 120. The hub 118 is advantageous for applications where a syringe is used to withdraw medications from a drug vial in that enclosure 120 reduces the dead volume in the hub 118.

Referring to FIGS. 20 and 21, a sheath 122 is slidably connected to the hub 18 to cover the needle 16 prior to use. Rails 124 guide the hub 18 into place as the safety shield apparatus 10 is slid into the sheath 122. A notched section 72 (FIG. 6) of the hub 18 interfaces with rails 124. It is envisioned that one or multiple rails may be employed. A hub stop 126 and detent bump 128 engage the hub 18 for retaining the sheath 122 in place prior to use. A rib 74 (FIG. 6) disposed on the hub 18 slides into the notch 112 (FIG. 17) in the shield 22 to provide for the proper alignment of the shield 22 as it is slidably connected to the hub 18.

Referring to FIGS. 22–37, hub 18 or 18' is connected and/or formed with a distal end 20A of a medical needle device, such as, for example, a fluid collection holder, syringe, etc., for affixing the needle 16 or 16' and hingedly affixing the shield 22 or 22' thereto.

Figure 22:
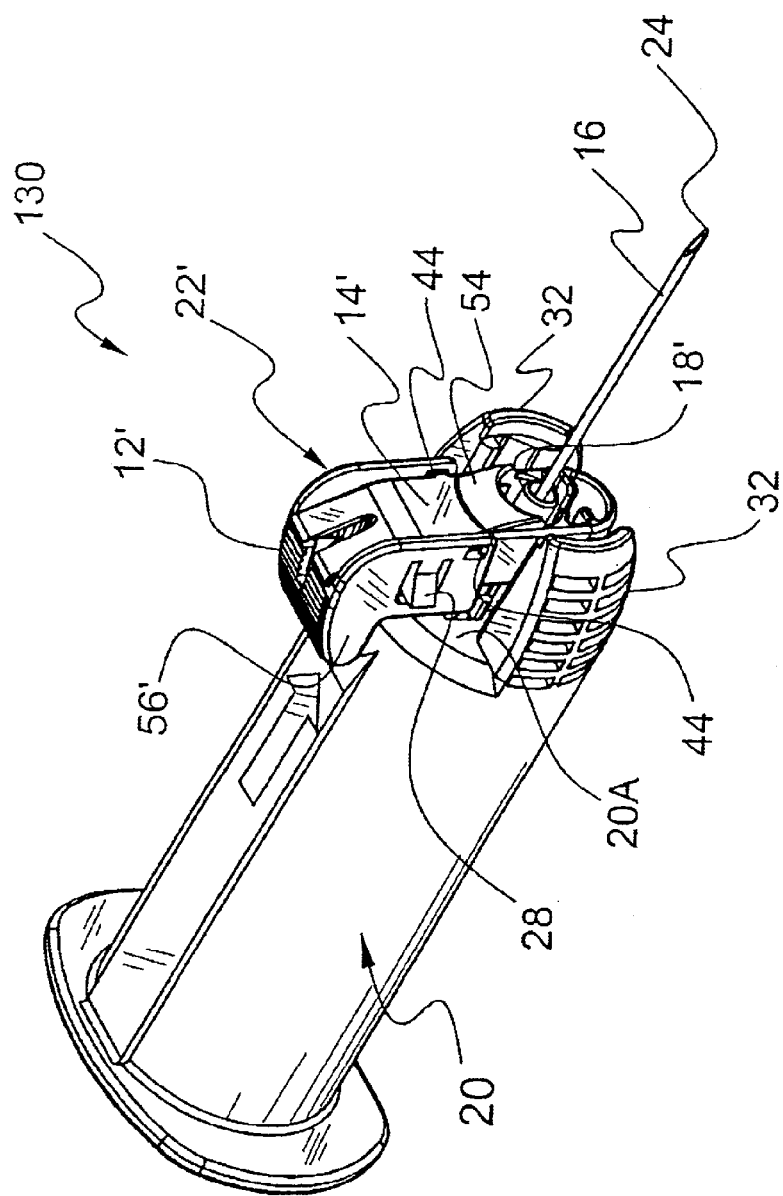
FIG. 22 is a perspective view of an alternate embodiment of the safety shield apparatus.
Figure 23:
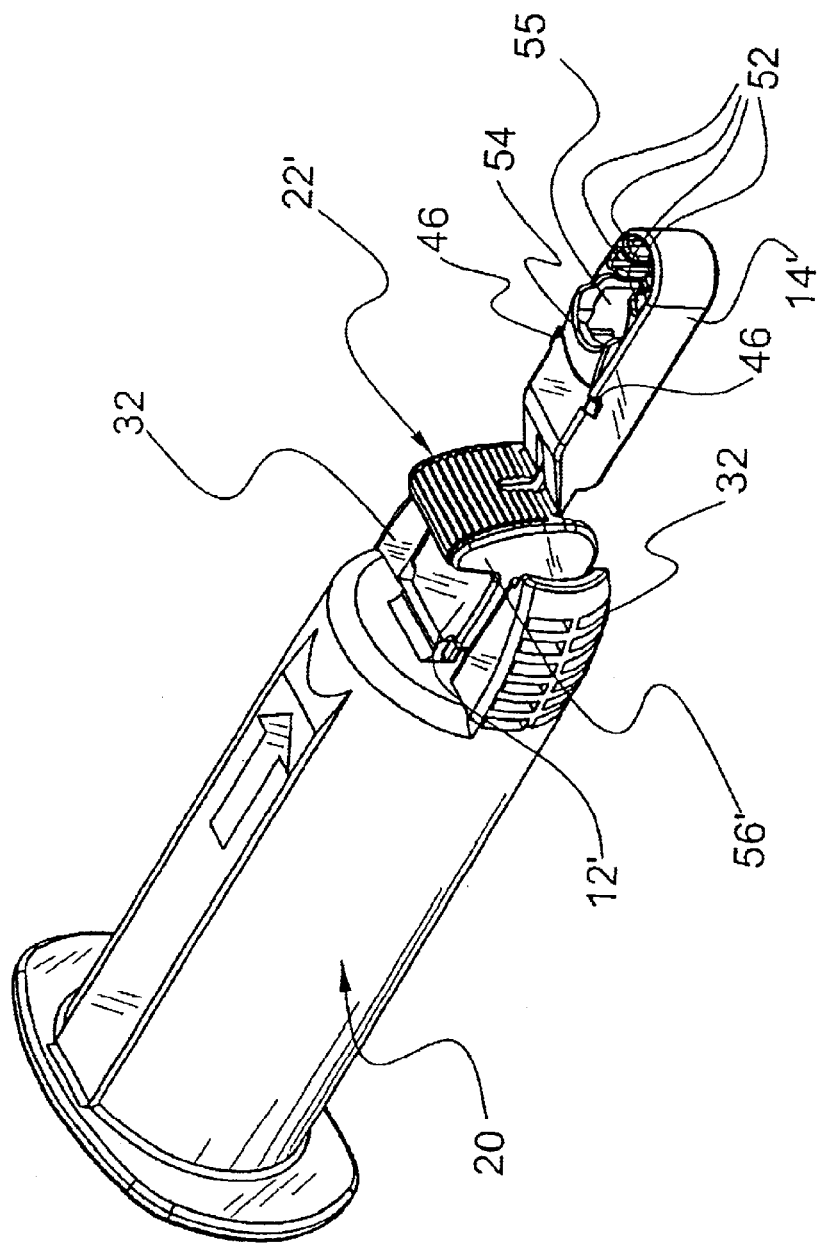
FIG. 23 is a perspective view of the safety shield apparatus illustrated in FIG. 22 with a shield in the extended position.
Figure 24:
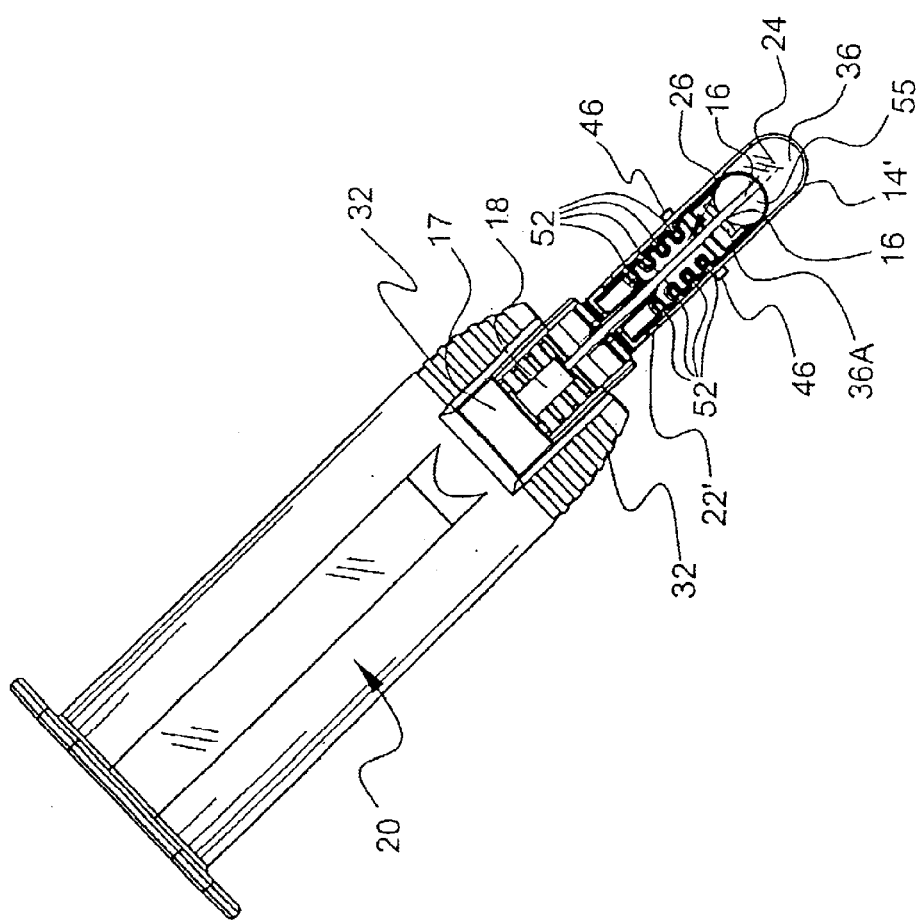
FIG. 24 is a view of an underside of the safety shield apparatus illustrated in FIG. 22.
Figure 25:
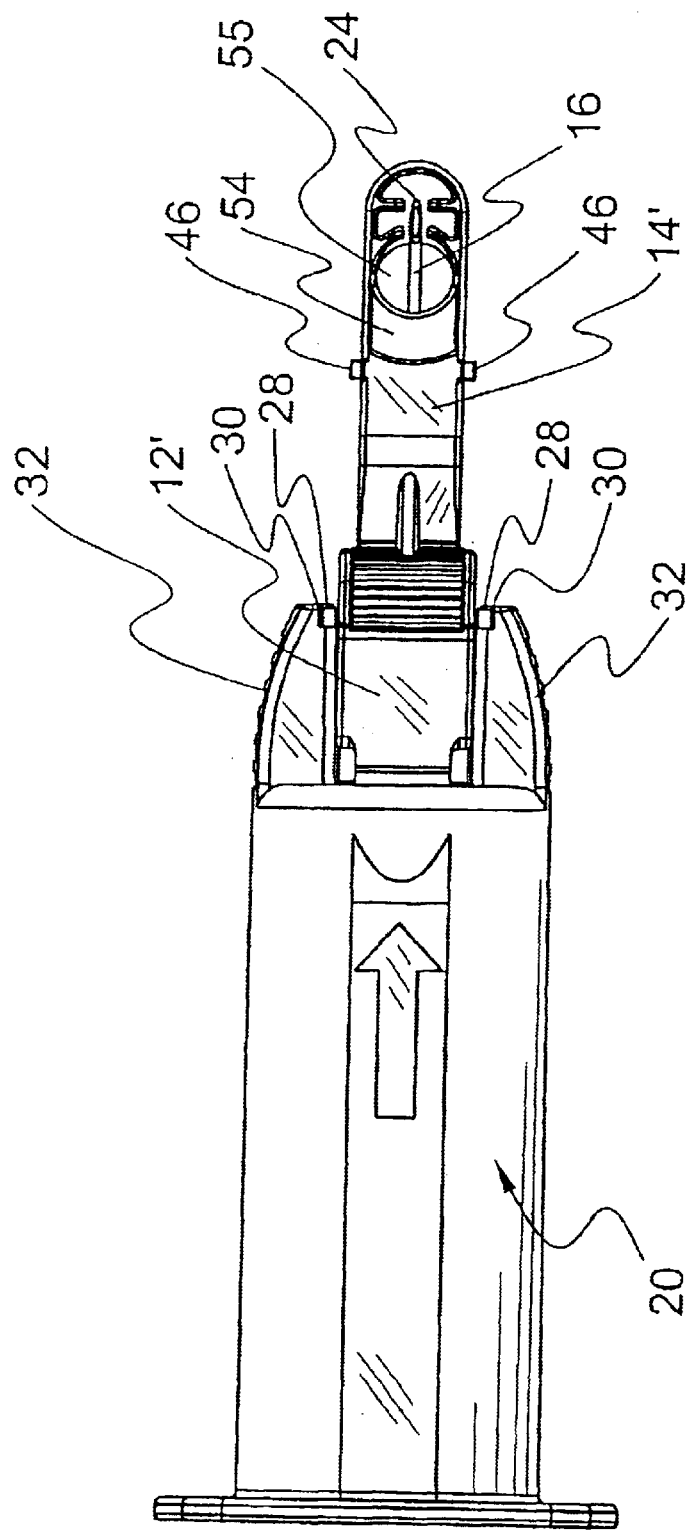
FIG. 25 is a top view of the safety shield apparatus illustrated in FIG. 22.

FIG. 22 illustrates a medical needle device, such as, for example, a blood collection holder 20 and a safety shield apparatus 130 with the shield 22' in a retracted position where the shield 22' is in a proximal position and the distal end 24 of the needle 16 is exposed prior to use. FIGS. 23–25 show the shield 22' in an extended position where the shield 22' extends beyond the distal end 24 of the needle 16 with segment 14' being the distal segment. At least one of the segments comprises an open orifice 55 through which the needle passes to form an axis of intersection about the needle 16. The embodiment illustrated in FIGS. 22–28 illustrates segment 14' having an open orifice 55. The alternate embodiment illustrated in FIGS. 29–36 includes three segments 13, 14" and 15 having an open orifice 55. Alternatively, a four segment device is contemplated with the most distal segment 14" having an open orifice 55.

FIG. 24 shows the underside of a two segment embodiment having a channel 26 for enclosing the needle 16 when the shield 22' is linearly extended. One or more ribs 52 are placed within one or more of the segments for positioning the needle.

One or more locks are associated with one or more of the segments for securing one of the segments relative to the shield in the extended position. The embodiment shown in FIGS. 22–26A illustrates holder 20 having a pair of arm extensions 32. Arm extensions 32 are diametrically disposed about distal end 20A of holder 20. It is contemplated that one or a plurality of arm extensions 32 may be employed. Arm extensions 32 include catches 30 (e.g., FIG. 25) formed on an inner surface thereof. Catches 30 engage a corresponding protrusion 28 formed with segment 12' of shield 22' (e.g., FIG. 22). Arm extensions 32 also include stepped rib portions that facilitate finger gripping to aid a clinician during insertion of the needle 16 into a patient.

Figure 30:
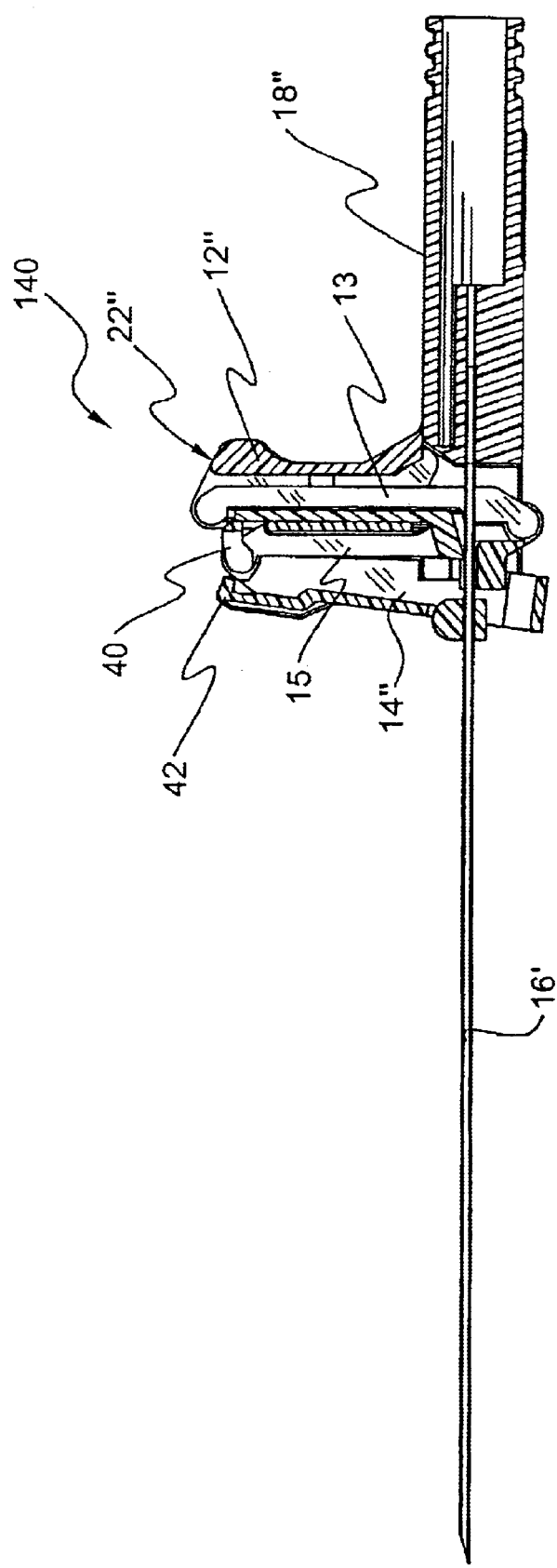
FIG. 30 is a cross-sectional view of the safety shield apparatus illustrated in FIG. 29.
Figure 31:
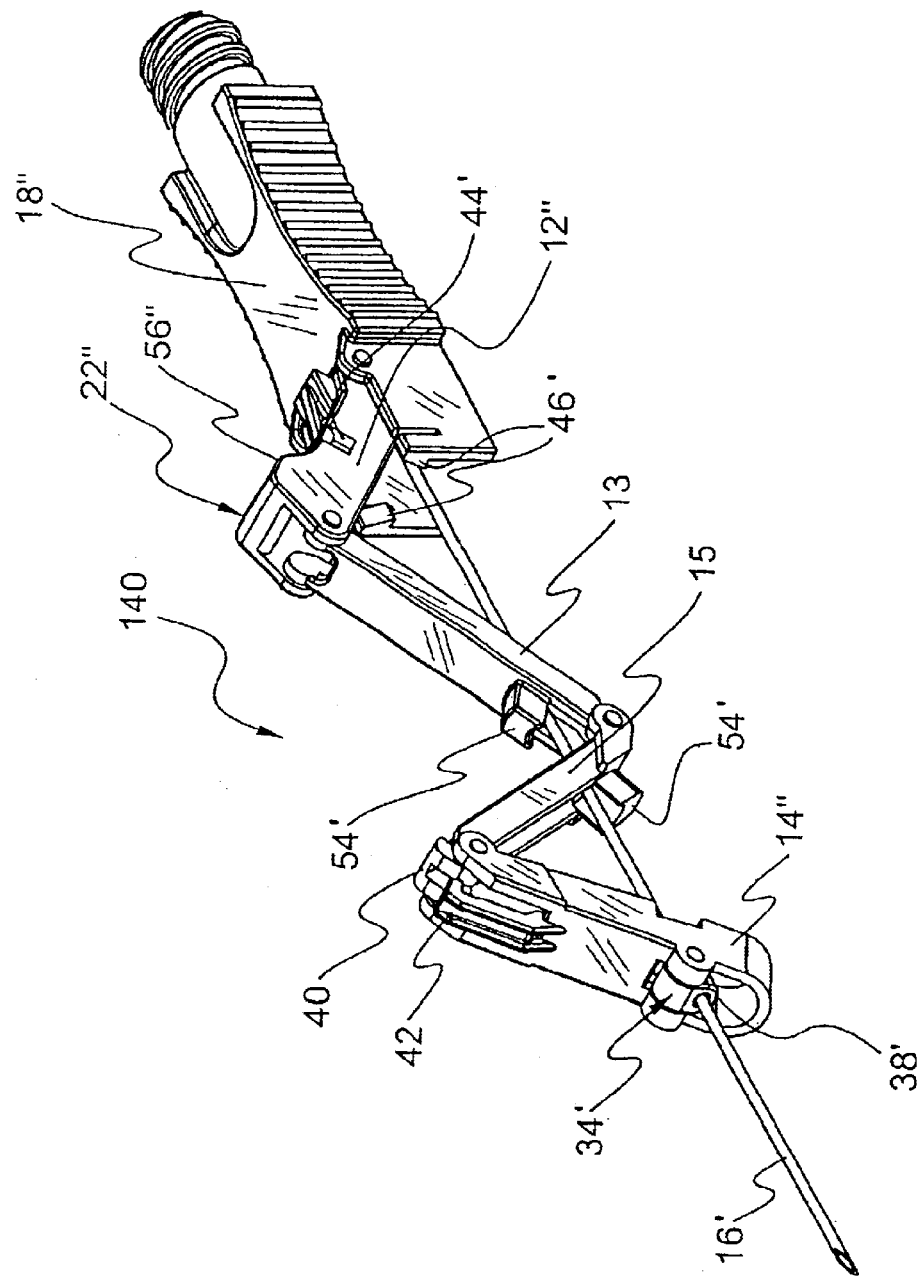
FIG. 31 is a perspective view of the safety shield apparatus illustrated in FIG. 29 with a shield in an intermediate position.
Figure 32:
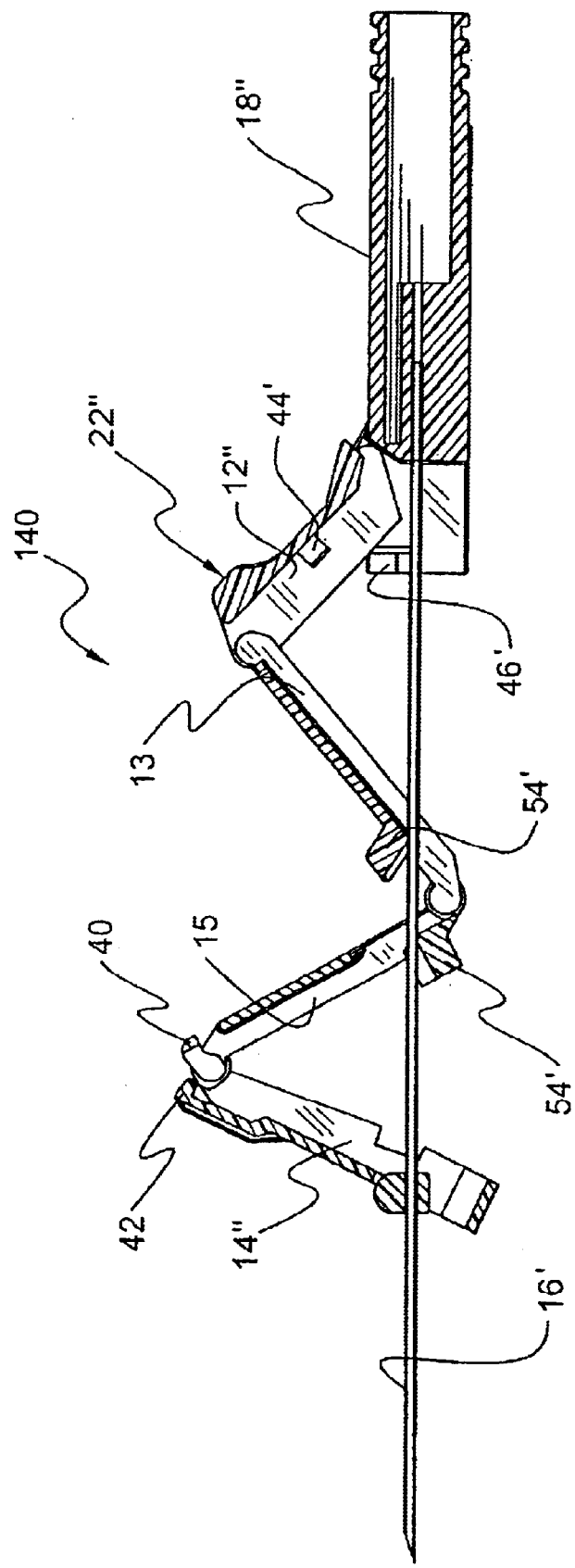
FIG. 32 is a cross-sectional view of the safety shield apparatus illustrated in FIG. 31.

It is contemplated that the locks can include catches disposed on one or more of the segments and corresponding protrusions disposed on the holder or hub. It is further contemplated that the catches and the corresponding protrusions may be disposed on adjacent segments of the shield for locking into position when the shield is in the extended position. For example, a segment may have a sidewall that overlaps an adjacent segment and includes a catch or protrusion that engages a corresponding protrusion or catch for locking the shield when in the extended position. Referring to FIG. 25, the catch 30 includes a capture hole, recess or indentation which engages and locks the protrusion 28 in place. Alternatively, the catch includes a flanged surface 40, as shown in FIGS. 30–32, for engagement with a protrusion or latching arm 42 when the shield 22" is in the locked and extended position. Flanged surfaced 40 may be constructed so as to lift the latching arm 42 during travel of the shield 22". This configuration prevents bending of long and/or fine gage needles.

The present invention also contemplates at least one surface disposed on the distal segment 14, 14' or 14" for securing the distal segment 14, 14' or 14" relative to the shield 22, 22' or 22" when in the extended position. One embodiment of the at least one surface is shown in FIG. 24, which includes the distal segment 14' having an underside comprising a surface 36 extending over all or a portion of the distal segment 14' for retaining the distal end 24 of the needle 16. Surface 36 is configured to retain at least a portion of distal end 24 of needle 16 within the enclosure of distal segment 14'. This design advantageously maintains shield 22' in the extended position and prevents hazardous exposure of needle 16. For example, if distal end 24 is caused to engage surface 36, surface 36 prevents distal end 24 from exiting distal segment 14'. Alternatively, distal segment 14' includes an oppositely spaced surface 36A that cooperates with surface 36 to retain distal end 24 within distal segment 14'. Engagement of the needle 16 with surface 36 and/or surface 36A prevents distal end 24 from exiting distal segment 14' and maintains shield 22' in the extended position.

The locks may also include a latch associated with the distal segment 14', such as one or more catches and a corresponding one or more protrusions disposed on adjacent segments of the shield 22' for locking into position when the shield 22' is in the extended position. For example, the distal segment 14 or adjacent segment 12' may have a sidewall that overlaps the adjacent segment or distal segment and includes a catch or protrusion that engages a corresponding protrusion or catch for locking the shield 22' when in the extended position. The catch may include a capture hole, recess or indentation which engages and locks the protrusion in place, as disclosed above.

Figure 29:
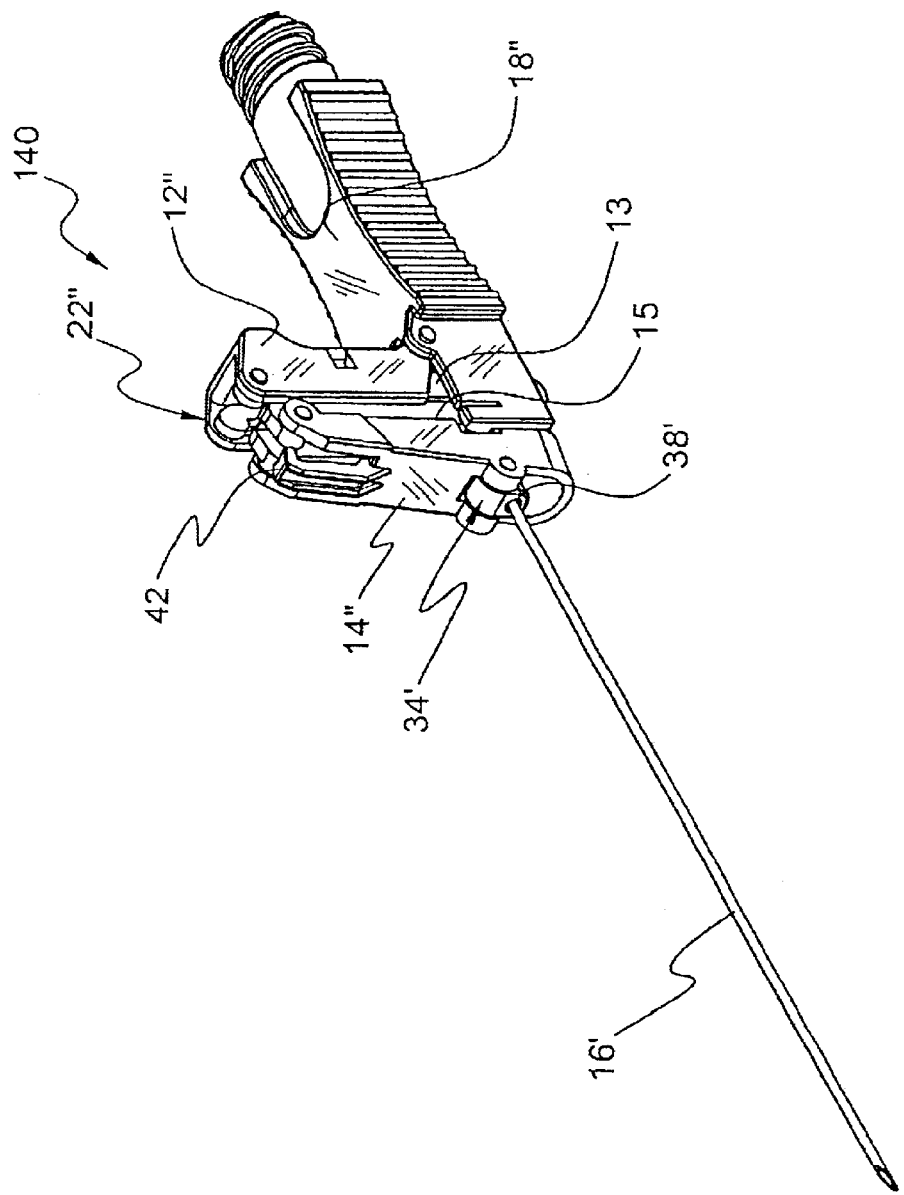
FIG. 29 is a perspective view of an alternate embodiment of the safety shield apparatus.

The latch may also include a linear bearing through which the needle passes. For example, FIG. 29 shows the latch 34' comprising a linear bearing 38' which is hingedly connected to the distal segment 14". The latch 34' may also include a hooked arm inside of the distal segment 14" which latches to the needle 16' when the shield 22" is in the extended position. A similar hooked arm may be utilized within any of the segments for latching to the needle.

As illustrated in FIG. 24, a kick-off plate 17 aids in actuating the shield 22' and prevents proximal segment 12' and distal segment 14' from over rotating and binding on the needle 16 before actuation.

Figure 27:
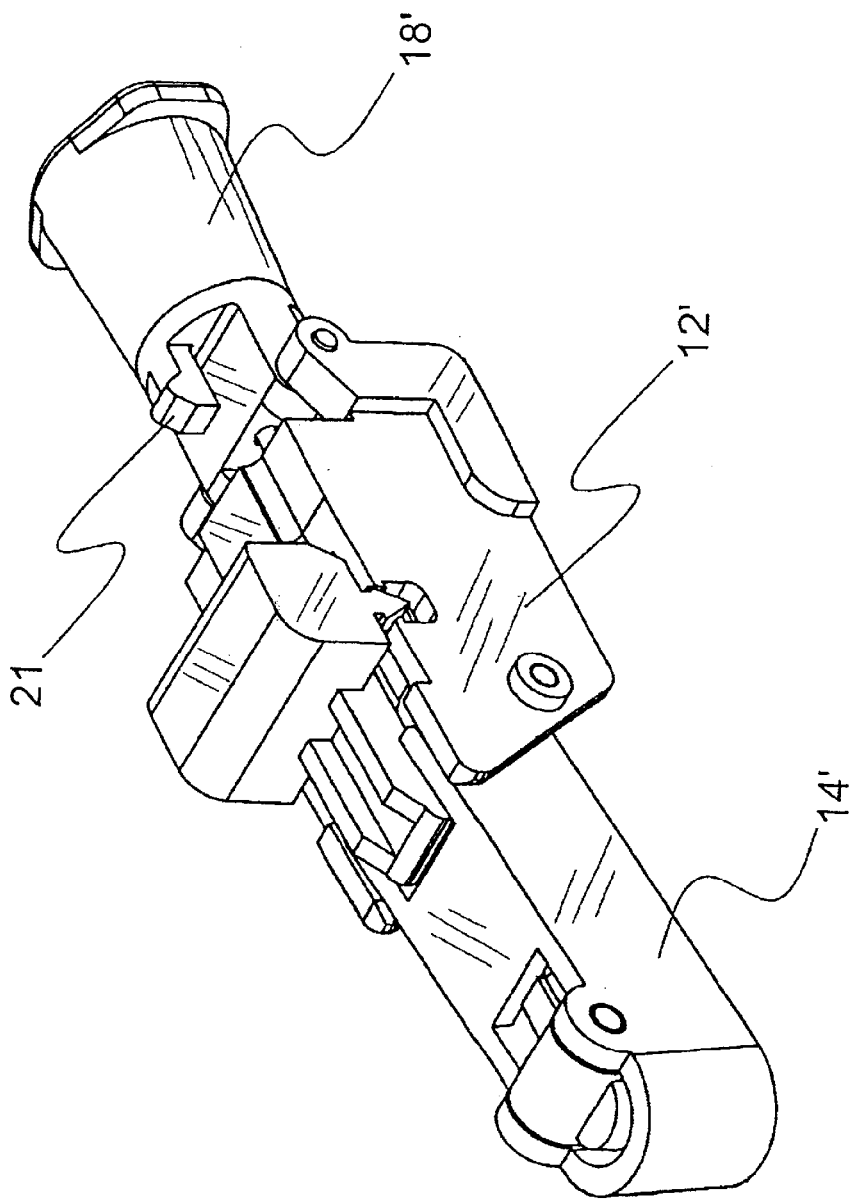
FIG. 27 is a perspective view of an alternate embodiment of the safety shield apparatus.
Figure 28:
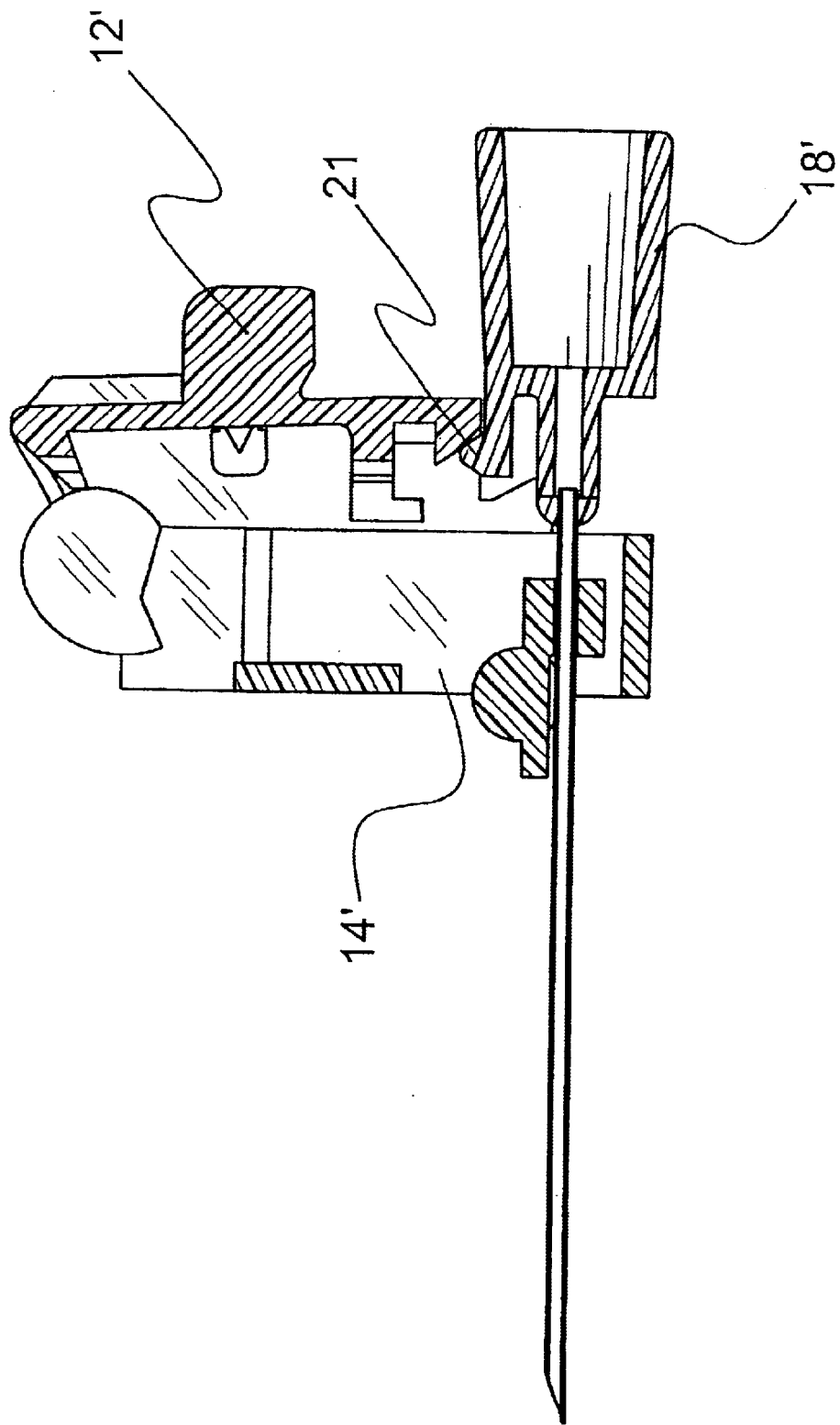
FIG. 28 is a cross-sectional view of the safety shield apparatus illustrated in FIG. 27.
Figure 36:
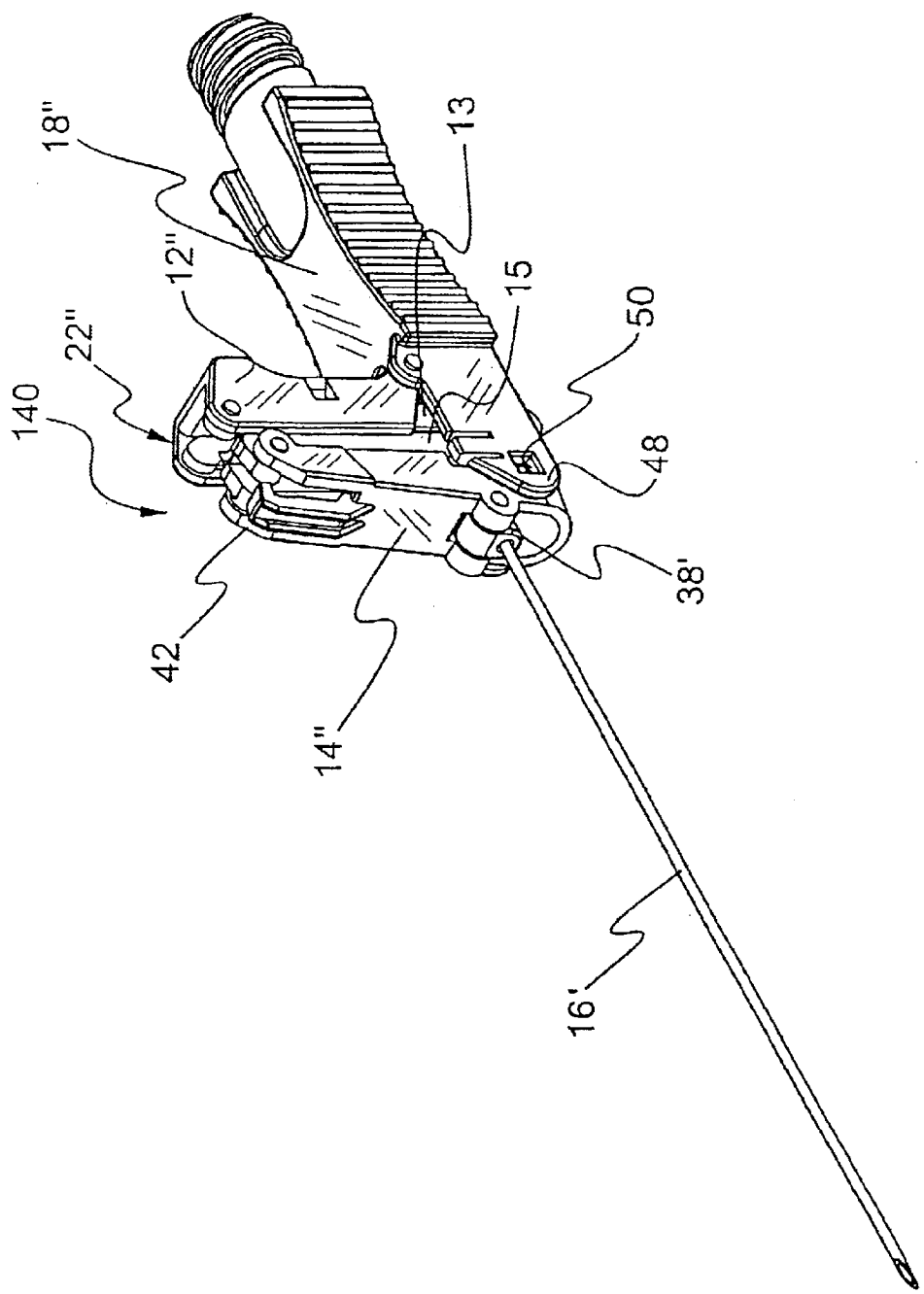
FIG. 36 is a perspective view of an alternate embodiment of the safety shield apparatus.
Figure 37:
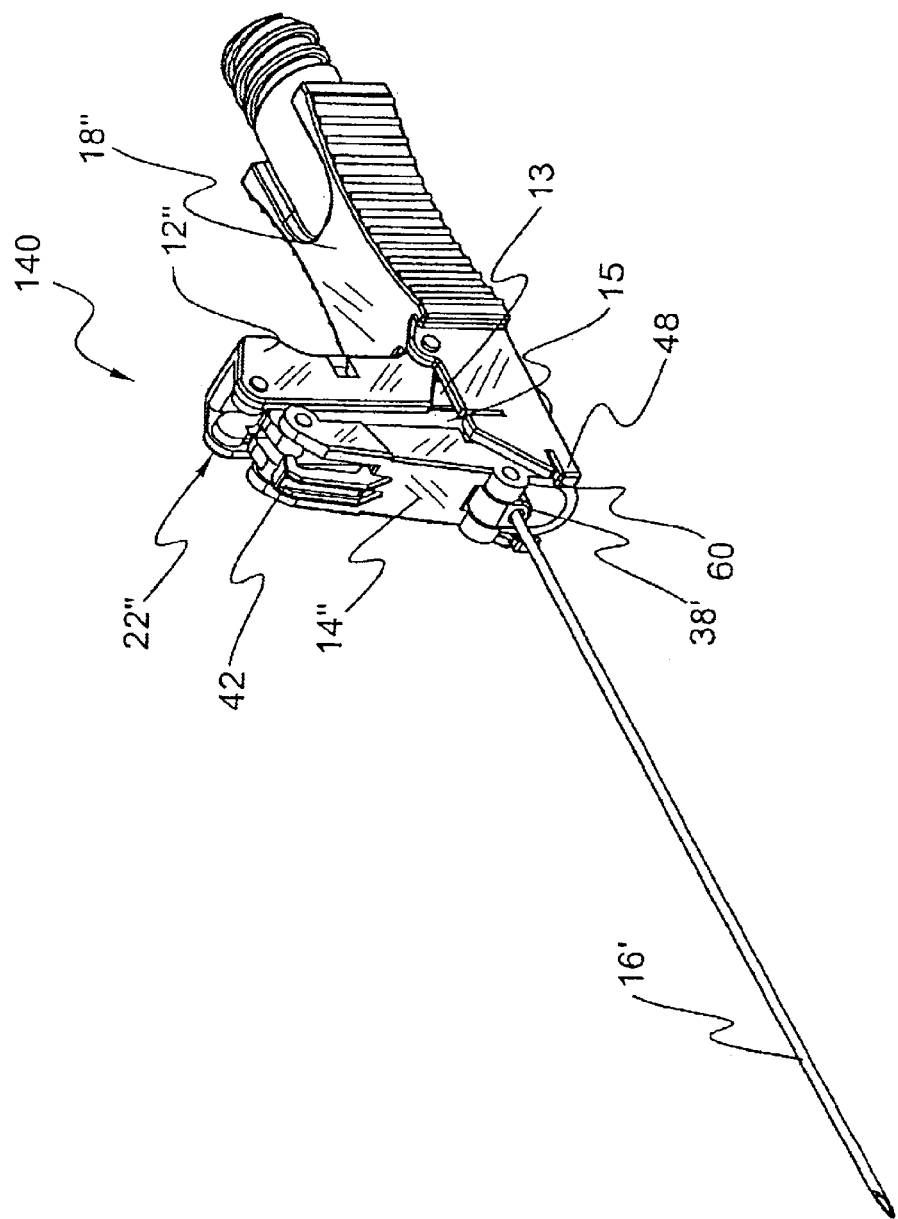
FIG. 37 is a perspective view of an alternate embodiment of the safety shield apparatus.

The present invention also contemplates a retainer for holding the two or more segments in a retracted condition. For example, the retainer for the embodiment shown in FIGS. 22–26A includes one or more retention catches disposed on one or more of the segments. The retention catches include one or more capture holes 44 for engagement with corresponding protrusions 46 when the shield 22' is in the retracted condition. The capture holes 44 may also be substituted for a recess or indentation which engages the contour of the protrusion 46. Alternatively, the retention catch may include one or more flanged surfaces for engagement with corresponding protrusions disposed on the shield 22'. FIGS. 27 and 28 show a retention catch 21 disposed on the hub 18' which latches to the proximal segment 12' when the shield is in the retracted condition. FIG. 36 illustrates another embodiment for a retainer which includes a retention arm 48 which engages a corresponding catch 50 disposed on the shield 22". FIG. 37 illustrates yet another embodiment for a retainer which includes a retention latch 60 which catches on the distal segment 14".

As illustrated in FIGS. 22–23 and 31–34, a needle guide 54 (54') comprises a surface for facilitating extension of the shield 22' along the needle 16 as the shield 22' is moved from the retracted position to the extended position. The shield 22' further comprises a raised surface 56' for aid in urging the shield 22' to the extended position. The embodiment shown in FIGS. 29–37 comprises two alternating needle guides 54' for guiding the one or more segments over the needle when moving the shield to the extended position. The alternating needle guides 54' may also prevent excessive wobbling of shield 22" as it is moved from the retracted position to the extended position. The shield 22" further comprises a raised surface 56" for aid in urging the shield 22" to the extended position.

Figure 33:
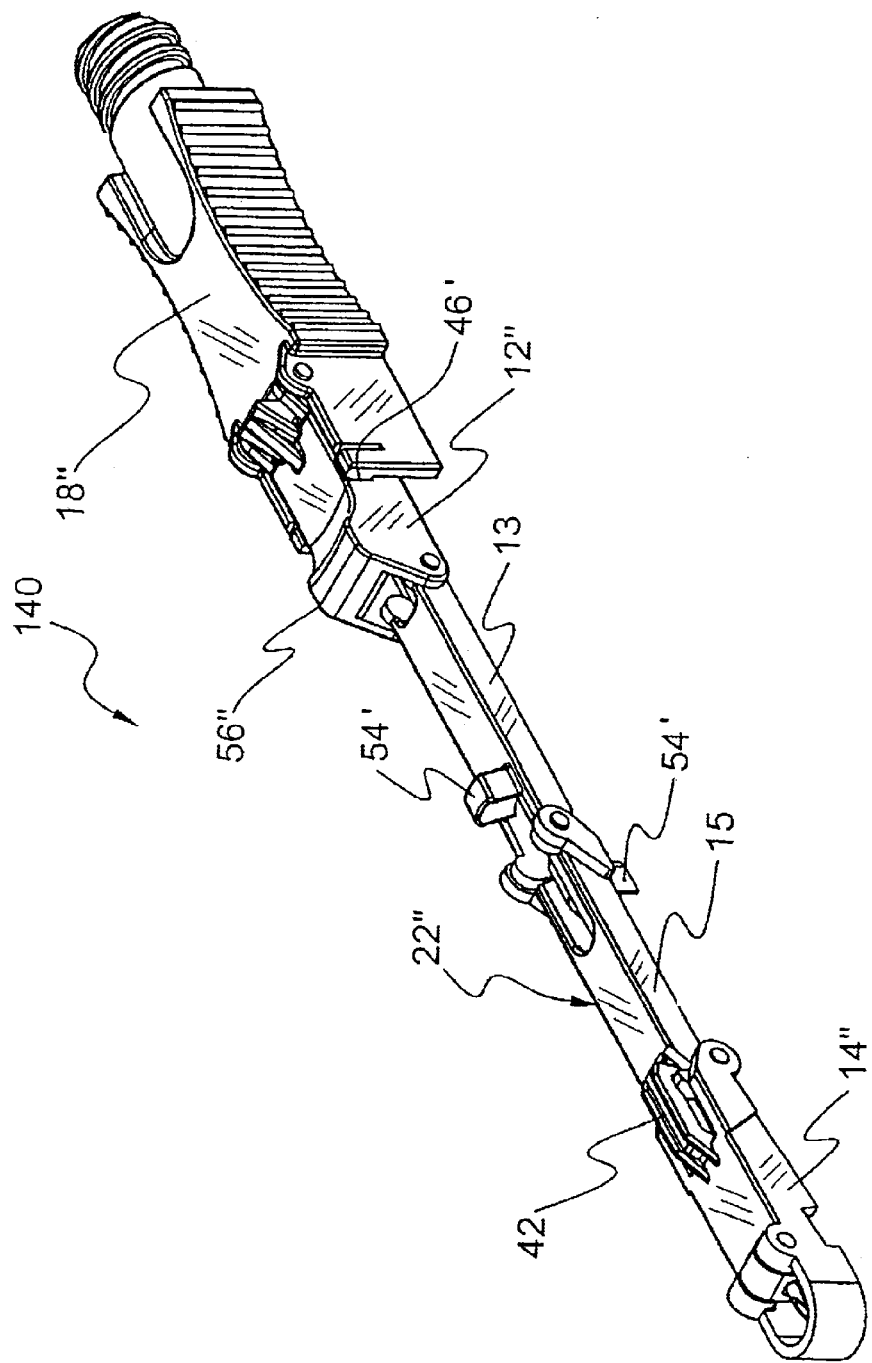
FIG. 33 is a perspective view of the safety shield apparatus illustrated in FIG. 29 with the shield in the extended position.
Figure 34:
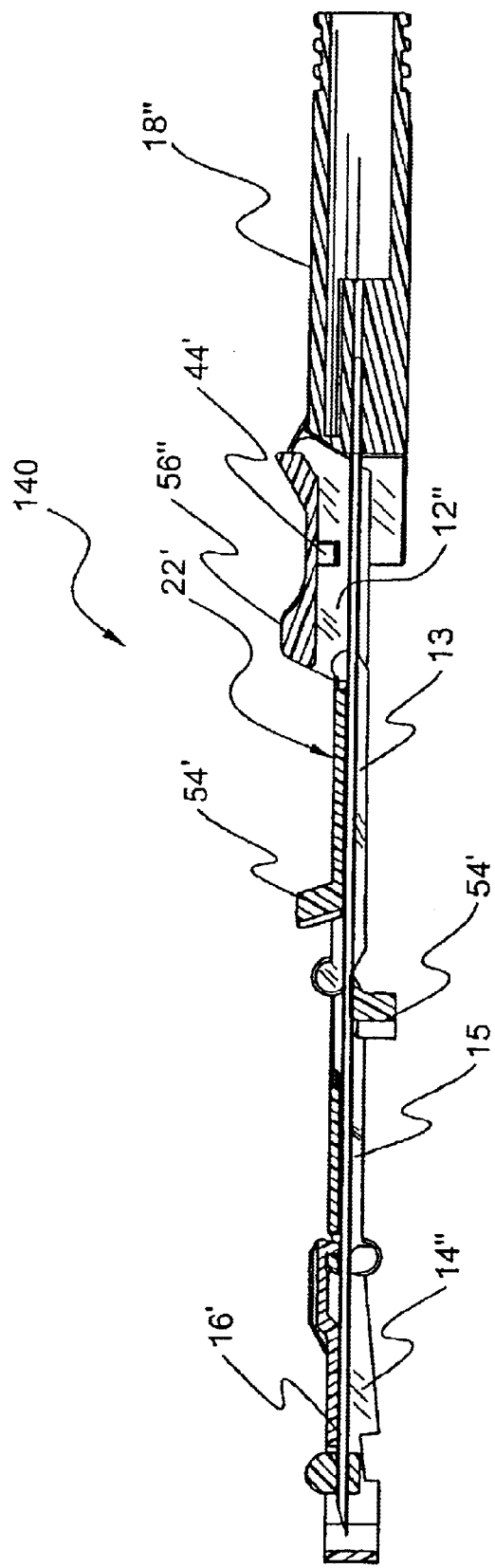
FIG. 34 is a cross-sectional view of the safety shield apparatus illustrated in FIG. 33.

The safety shield apparatus 140 with a four segment embodiment illustrated in FIGS. 29–37 is advantageous for long needle applications, such as for guide wire insertion needles. The shield 22" includes a proximal segment 12", a first intermediate segment 13, a second intermediate segment 15 and a distal segment 14" for enclosing the needle 16' when the shield 22" is in the extended position, as shown in FIGS. 33 and 34. Intermediate segments 13 and 15 include an open orifice through which the needle 16' passes to form an axis of intersection about the needle 16'. Latching arm 42 engages the flanged surface 40, as shown in FIGS. 30–32, for securing the distal segment 14" relative to the shield 22" in the extended position. Needle guides 54' facilitate extension of the shield 22" along the needle 16' as the shield 22" is moved from the retracted position to the extended position. Protrusions 46' of the arm extensions, similar to arm extensions 32 described herein, engage capture holes 44' for securing the distal segment 14" relative to the shield 22" when in the extended position. The arm extensions extend from needle hub 18" and are spaced apart to define a cavity that is configured for disposal of shield 22". Safety shield apparatus 140 includes pinned hinges, although hinges or a combination of living and pinned hinges may be utilized.

The scope of the present invention also contemplates open-ended needles and/or double walled needles for applications such as phlebotomy, transmission of a guidewire and so forth.

Figure 26:
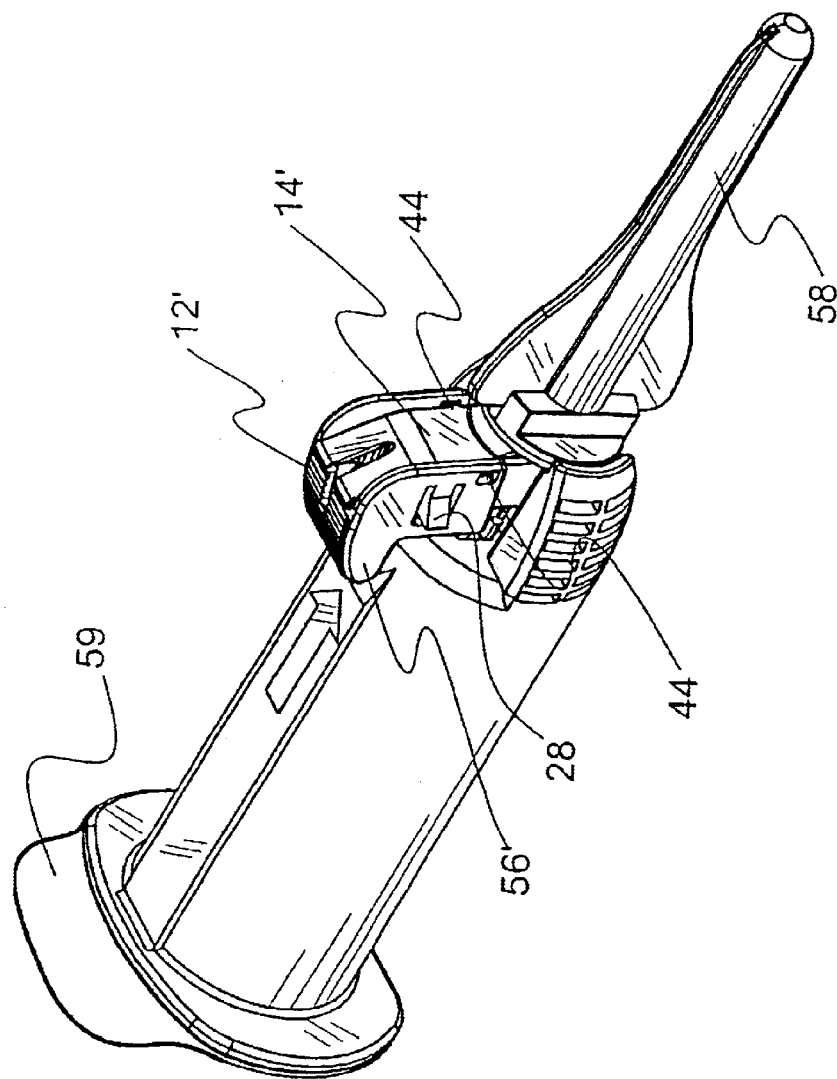
FIG. 26 is a perspective view of the safety shield apparatus illustrated in FIG. 22 with a needle cover.
Figure 26A:
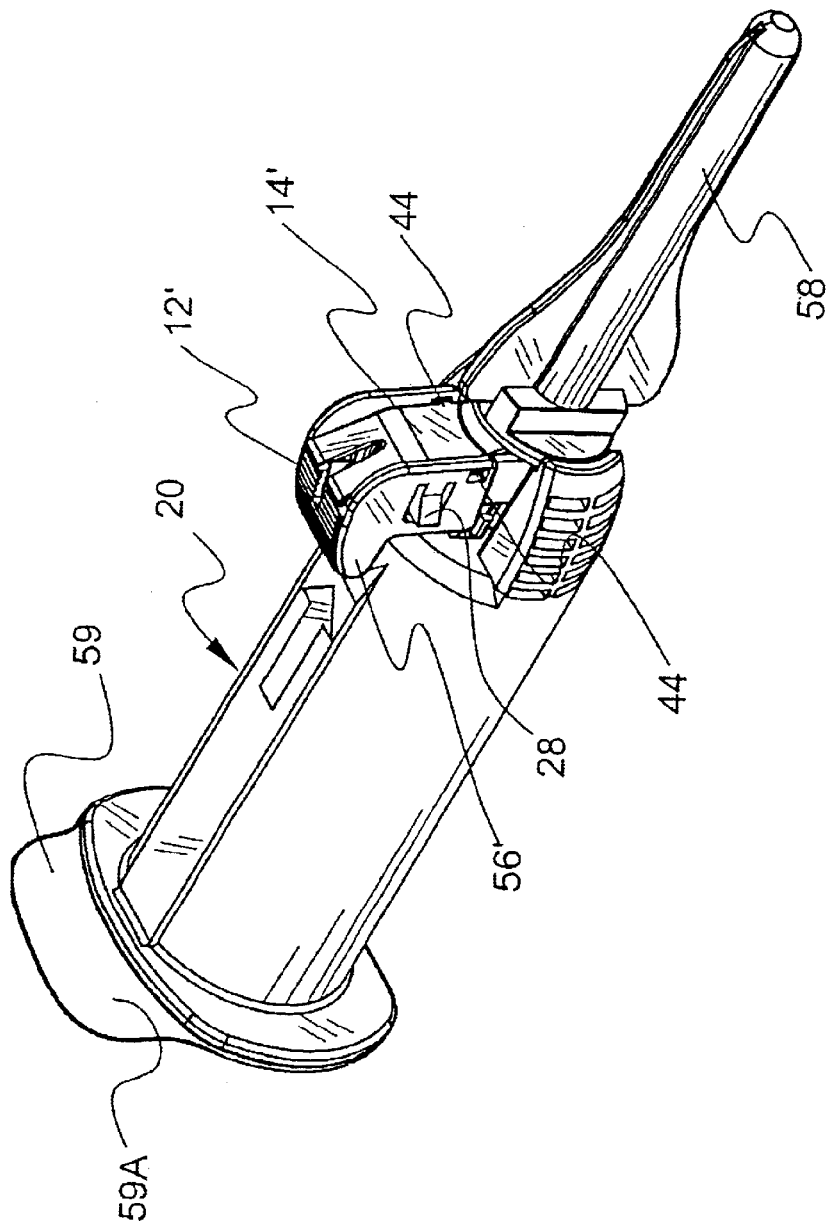
FIG. 26A is a perspective view of the safety shield apparatus illustrated in FIG. 22 with a needle cover.
Figure 26B:
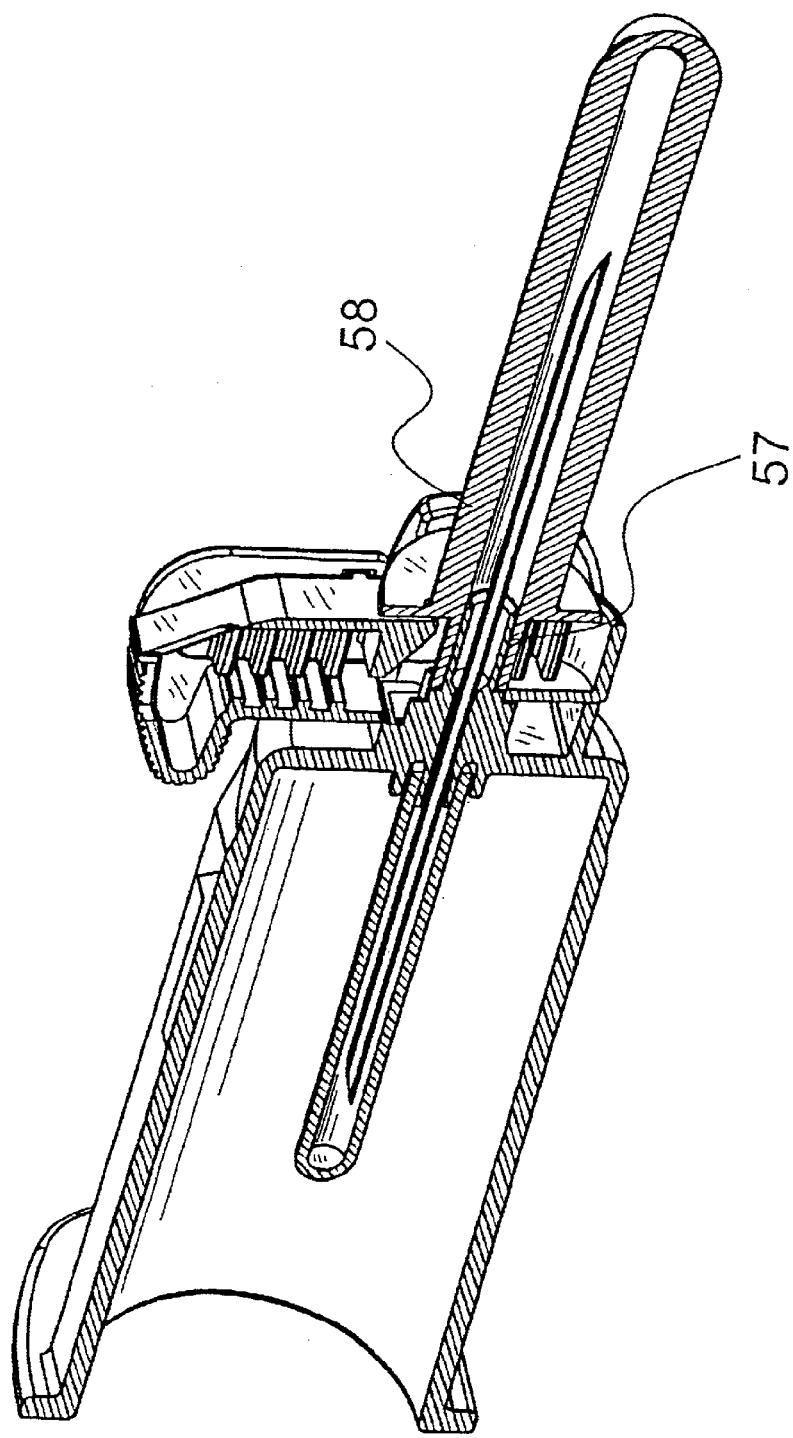
FIG. 26B is a part cross-sectional view of the safety shield apparatus illustrated in FIG. 26A.
Figure 35:
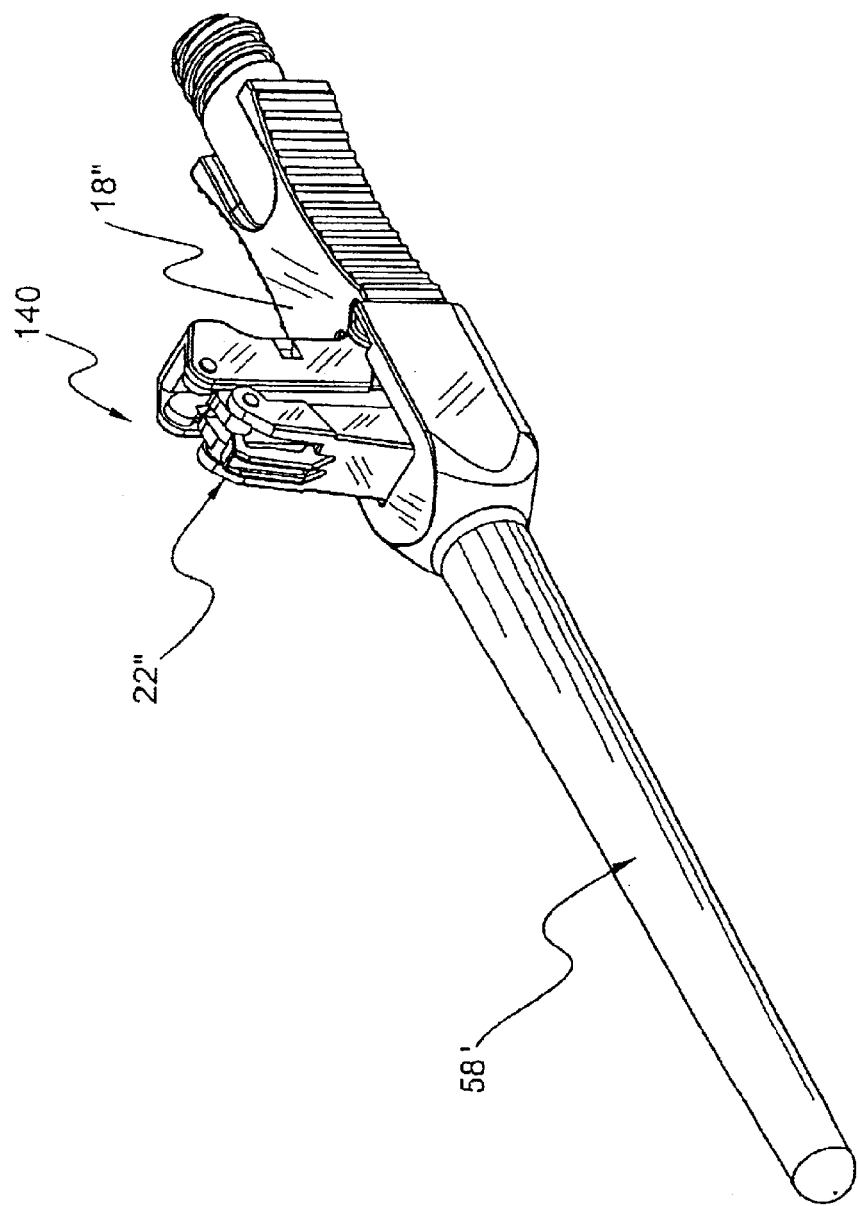
FIG. 35 is a perspective view of the safety shield apparatus illustrated in FIG. 29 with a needle cover.

As shown in FIGS. 26A and 35, a sheath 58 (58' as shown in FIG. 35) is commonly used to protect needles 16 prior to use and to prevent inadvertent unfolding or actuation of the safety shield 10 before removal of sheath 58 for use of needle 16. The safety shield 10 may be constructed in a manner which is self-packaging. For example, a sterility seal may be provided at the sheath/hub interface 57, as shown in FIG. 26B. The sterility seal may take the form of interference fit, tortuous path, adhesive, weld or any other means of providing a seal to contamination.

FIGS. 26A and 26B depict a tortuous path seal at interface 57 and an adhesive membrane seal 59. Adhesive membrane seal 59 maintains sterility of an interior surface of the barrel of holder 20 and the proximal end of needle 16. Adhesive membrane seal 59 may be fabricated from any material suitable for needle applications in accordance with the present disclosure, such as, for example, paper, plastics, etc. A grasping tab 59A of seal 59 facilitates removal of seal 59 from holder 20 in accordance with use. Seal 59 advantageously reduces cost of manufacturing and packaging of the medical needle device.

Figure 38:
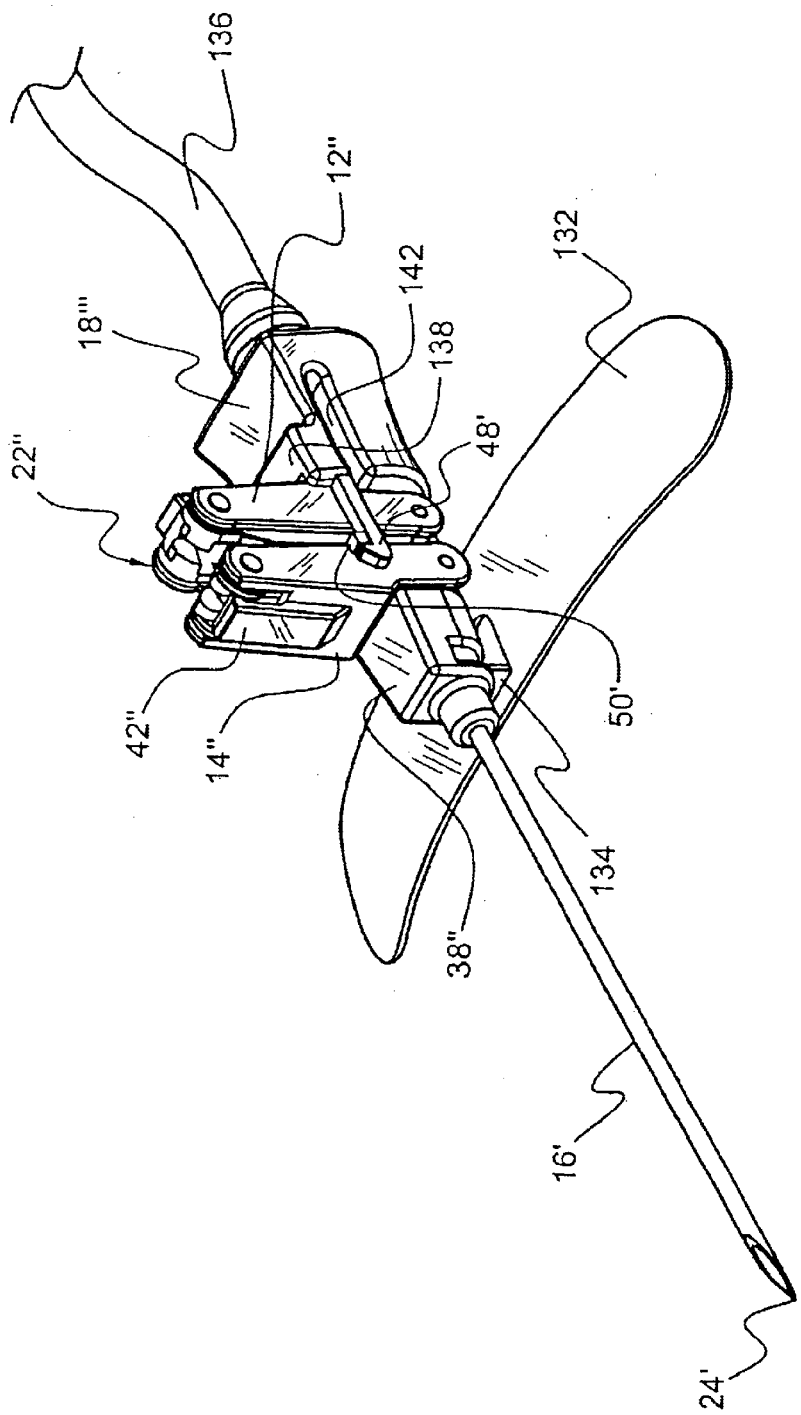
FIG. 38 is a perspective view of an alternate embodiment of the safety shield apparatus.
Figure 39:
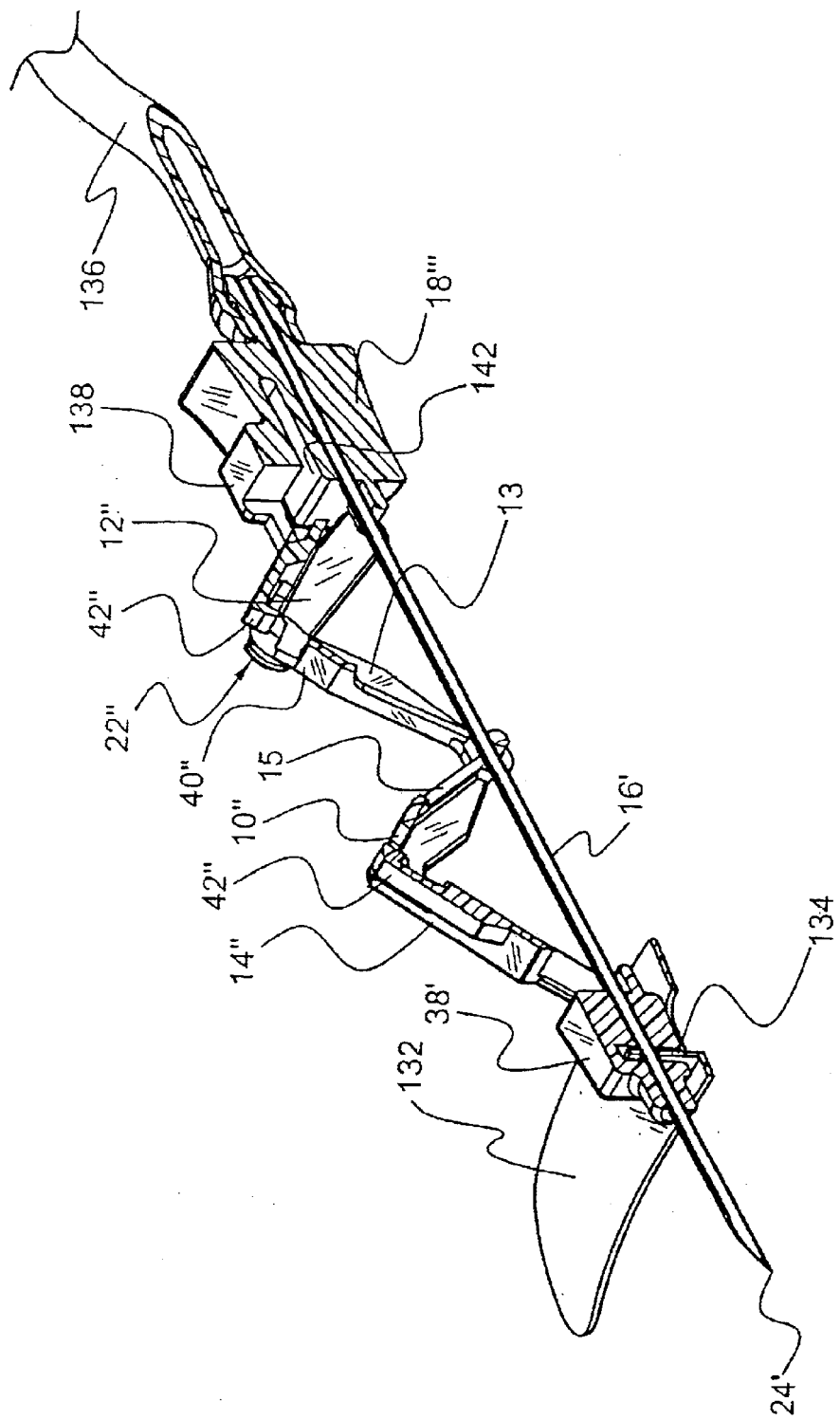
FIG. 39 is a part cross-sectional view of the safety shield apparatus illustrated in FIG. 38 during extension.
Figure 40:
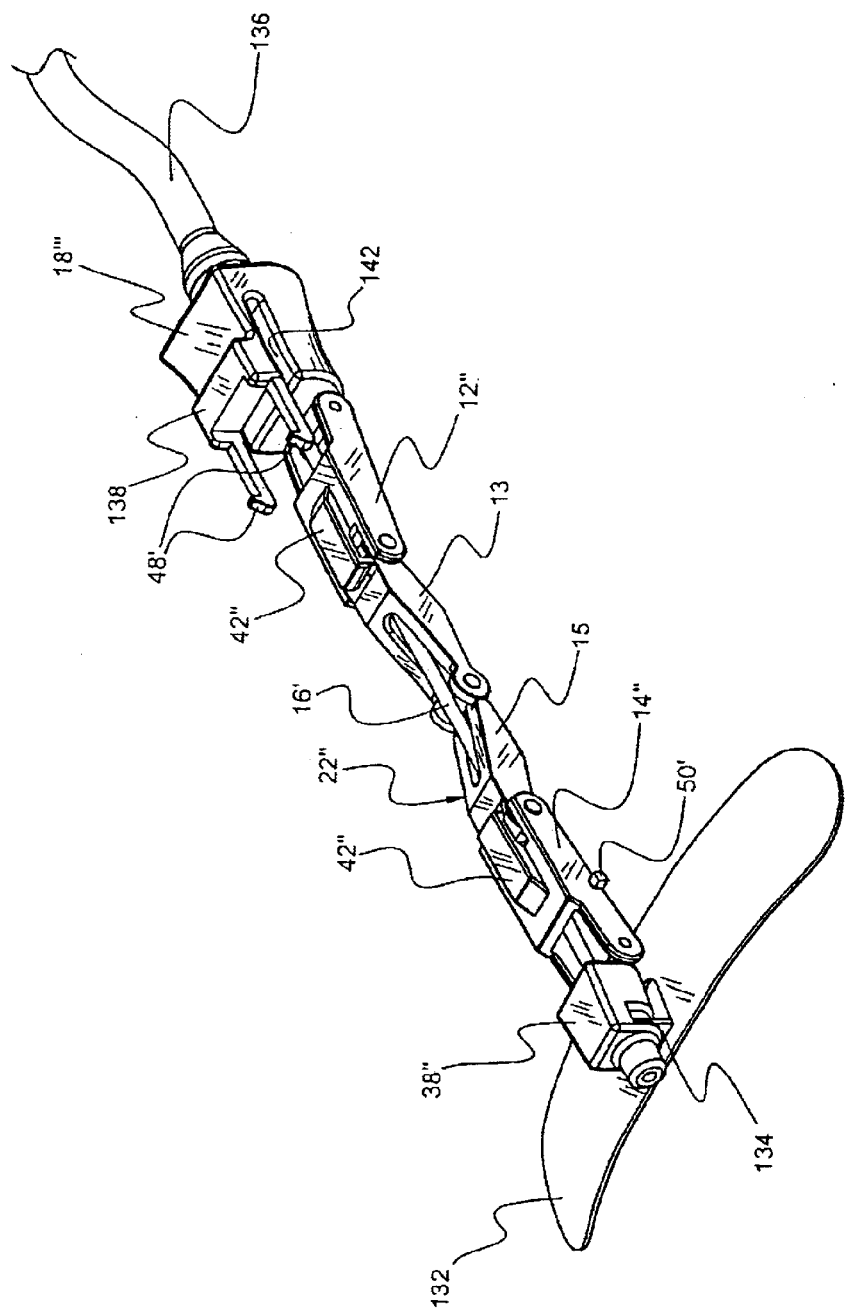
FIG. 40 is a perspective view of the safety shield apparatus illustrated in FIG. 40 having a releasably attached tape down member.
Figure 41:
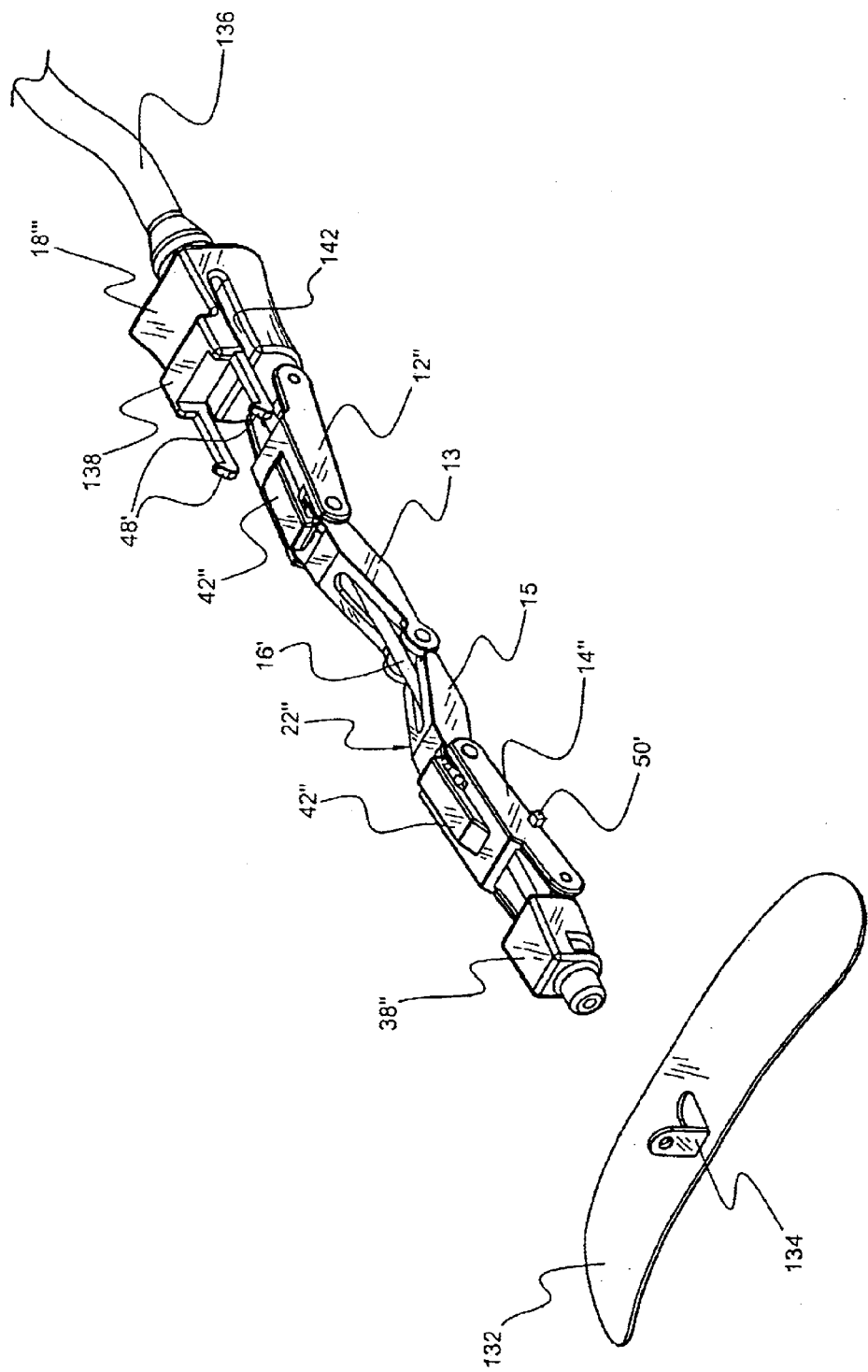
FIG. 41 is a perspective view of the safety shield apparatus illustrated in FIG. 40 having the releasably attached tape down member in a post-use condition immediately after release of the tape down member.

FIGS. 38–41 show an embodiment of the present invention incorporating a tape down member 132 which releases from the shield 22" as a portion 134 of the tape down member 132 in contact with the needle 16' is advanced past the distal end 24' of the needle 16'. Alternatively, a number of methods of releasably attaching the tape down member 132 to the shield 22" are contemplated. FIG. 38 shows the safety shield 22" in a pre-use state, while FIG. 39 shows the safety shield 22" during extension. FIG. 40 shows the tape down member 132 immediately prior to release. FIG. 41 shows the shield 22" in a post-use and protected state with the tape down member 132 separated from the shield 22". The tape down member 132 may be taped to a patient using separate tape or, alternatively, tape down member 132 may have an adhesive disposed on its underside. It is envisioned that tape down member 132 may engage the patient via manual pressure, etc. The tape down member 132 may also be used as a gripping feature that is not necessarily taped to the patient.

The tape down member 132 provides for passive activation of the present invention. The safety shield 22" comprises a proximal segment 12", a first intermediate segment 13, a second intermediate segment 15 and a distal segment 14" for protecting the needle 16' when the shield 22" is in the extended position, as shown in FIG. 41. The safety shield 22" is released for activation by first pressing extension plate 138 towards surface 142 on the hub 18''', which releases retention arm 48' from catch 50'. Intermediate segments 13 and 15 include an open orifice through which the needle 16' passes to form an axis of intersection about the needle 16'. Latching arm 42" engages the flanged surface 40" for securing the distal segment 14" relative to the shield 22" in the extended position. Shield 22" can be connected using pinned hinges, living hinges or a combination of living and pinned hinges. The apparatus may be utilized with a extension set tubing 136 for fluid communication, or alternatively, may include a luer fitting for attachment to a variety of medical needle devices.

Referring to FIGS. 42–53, an embodiment of a safety shield apparatus 144 is shown comprising a port access needle 146 including a shield 150 of hingedly connected segments 12' and 14' for protecting the distal end 147 of needle 146 after use in a medical procedure. Needle 146 is oriented in two axes such that a distal needle portion 146A is oriented at an axis 90 degrees relative to an axis defined by a proximal needle portion 146B. It is contemplated that distal needle portion 146A and proximal needle portion 146B may be oriented at various angular displacements. As shown in FIGS. 42–52, segments 12' and 14' may be configured for a low profile such that the segments may be folded into each other in a pre-use state as a result of either segment having smaller dimensions than the other.

Figure 42:
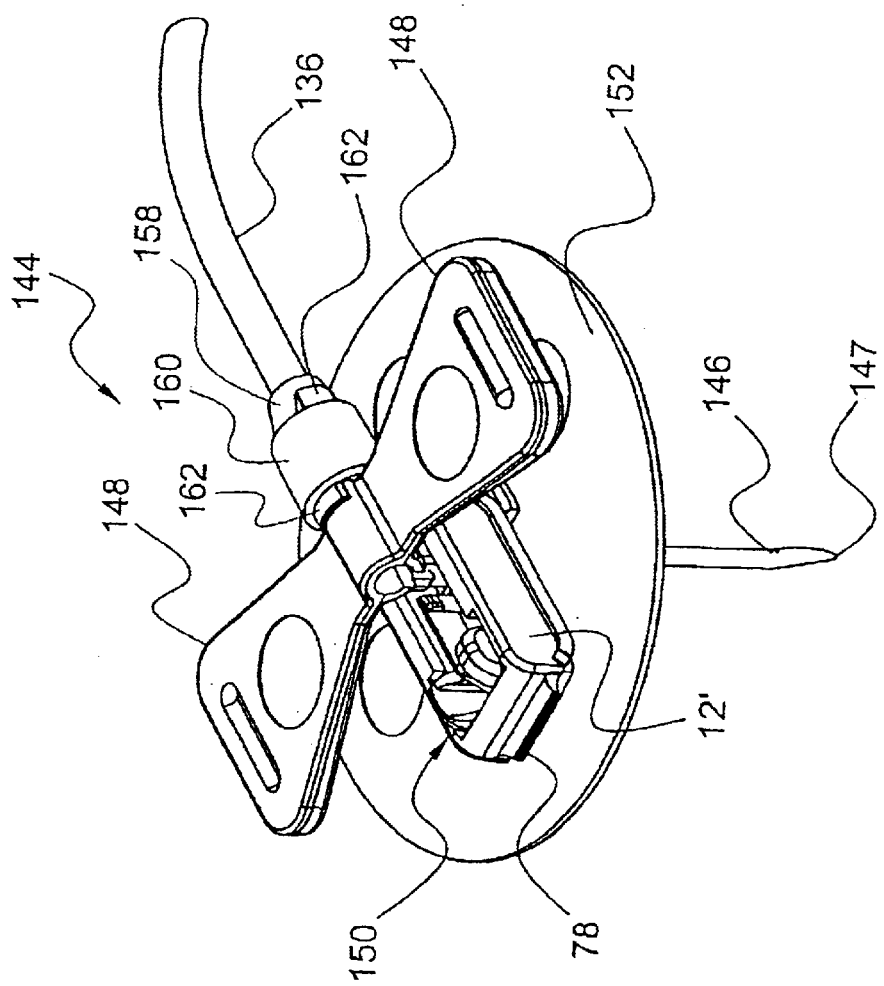
FIG. 42 is a perspective view of a medical needle safety shield apparatus in a retracted position, in accordance with the principles of the present invention.
Figure 43:
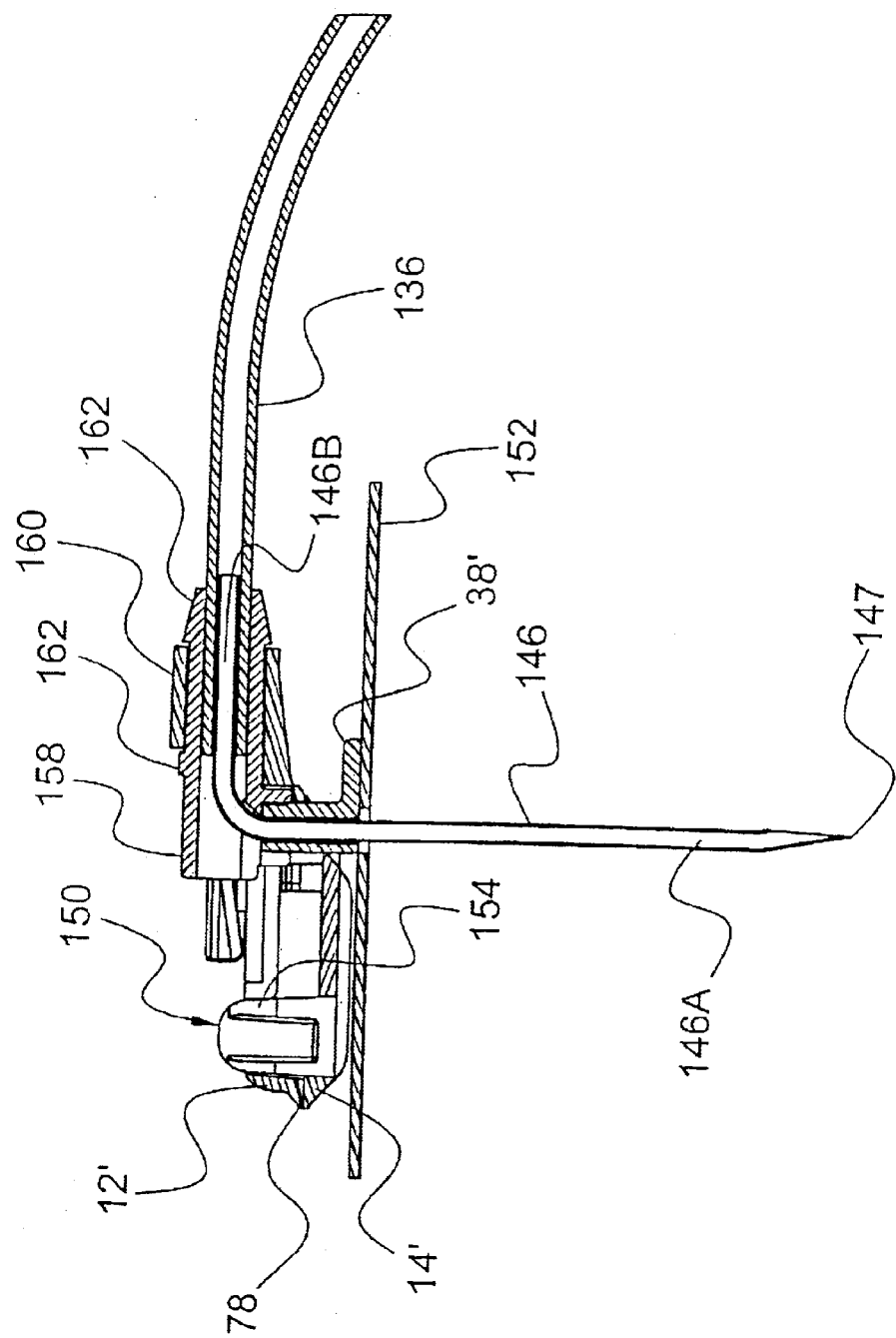
FIG. 43 is a cross-sectional view of the safety shield apparatus shown in FIG. 42.
Figure 44:
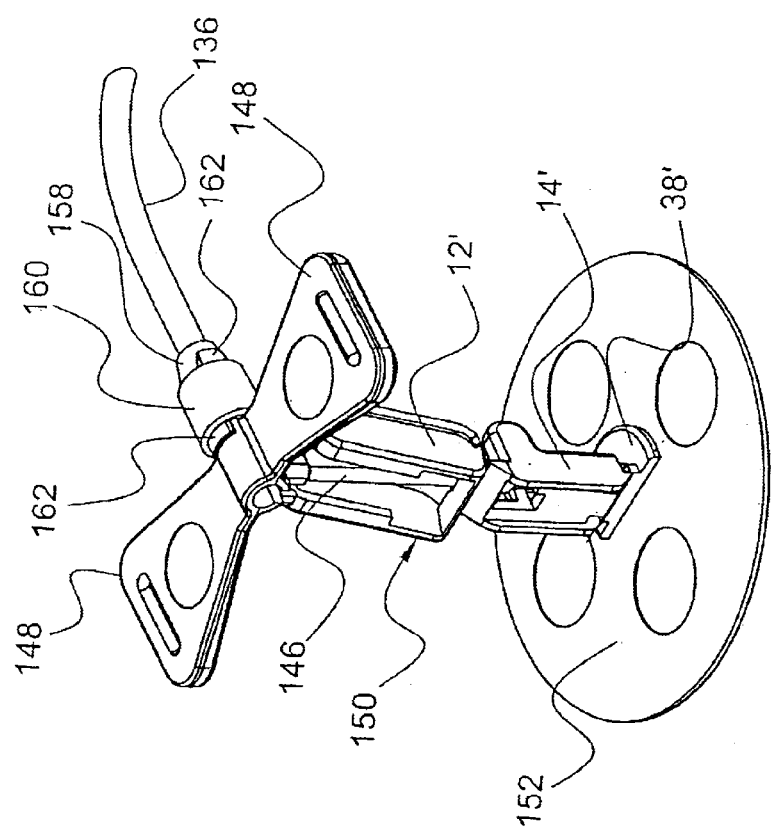
FIG. 44 is a perspective view of the safety shield apparatus shown in FIG. 42 fully extended.
Figure 45:
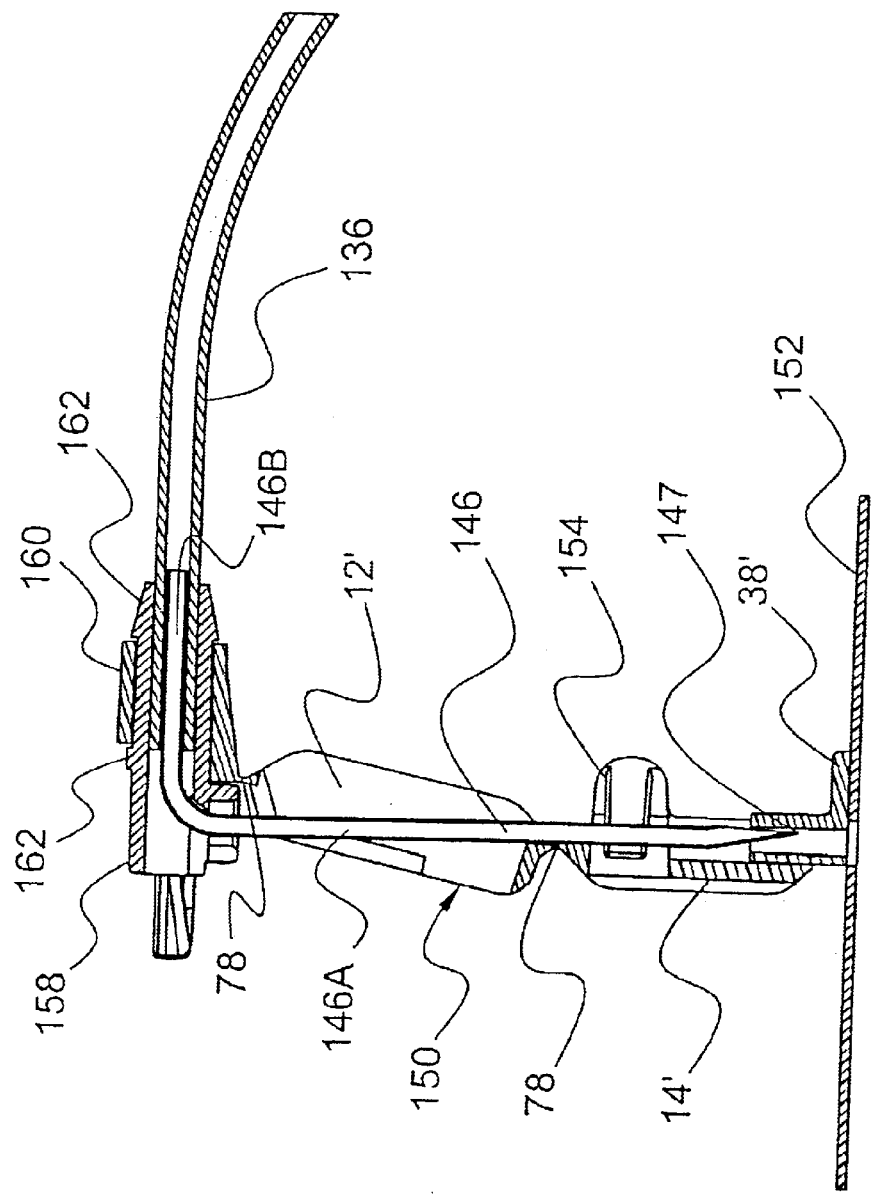
FIG. 45 is a cross-sectional view of the safety shield apparatus shown in FIG. 44.
Figure 49:
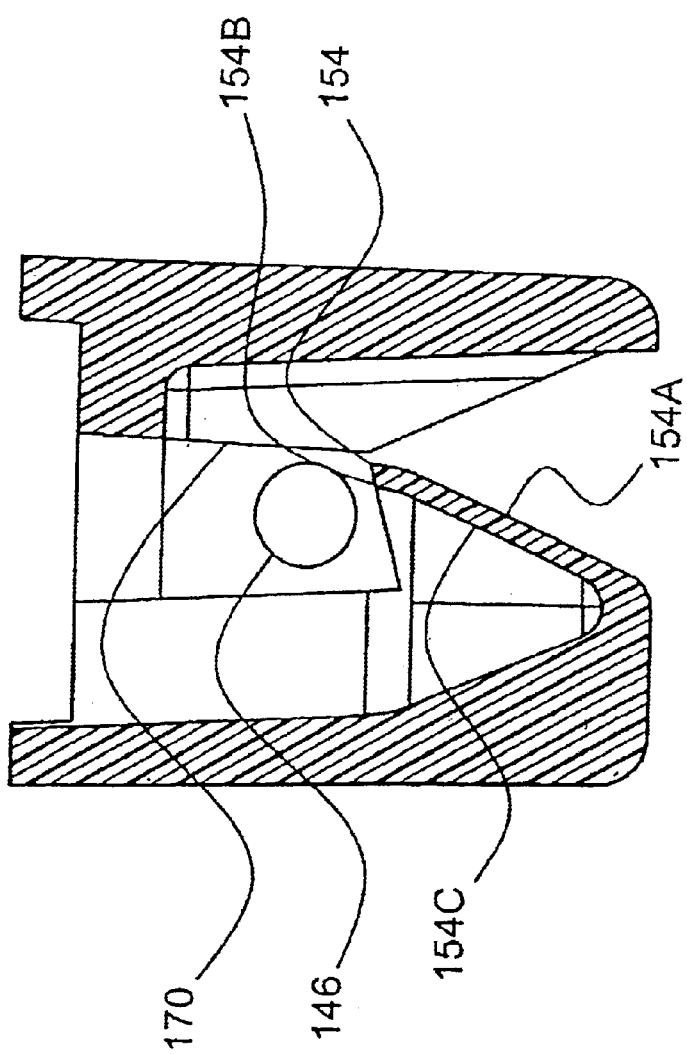
FIG. 49 is a cross-sectional view of the safety shield apparatus shown in FIG. 42 showing an embodiment of a needle latch.
Figure 50:
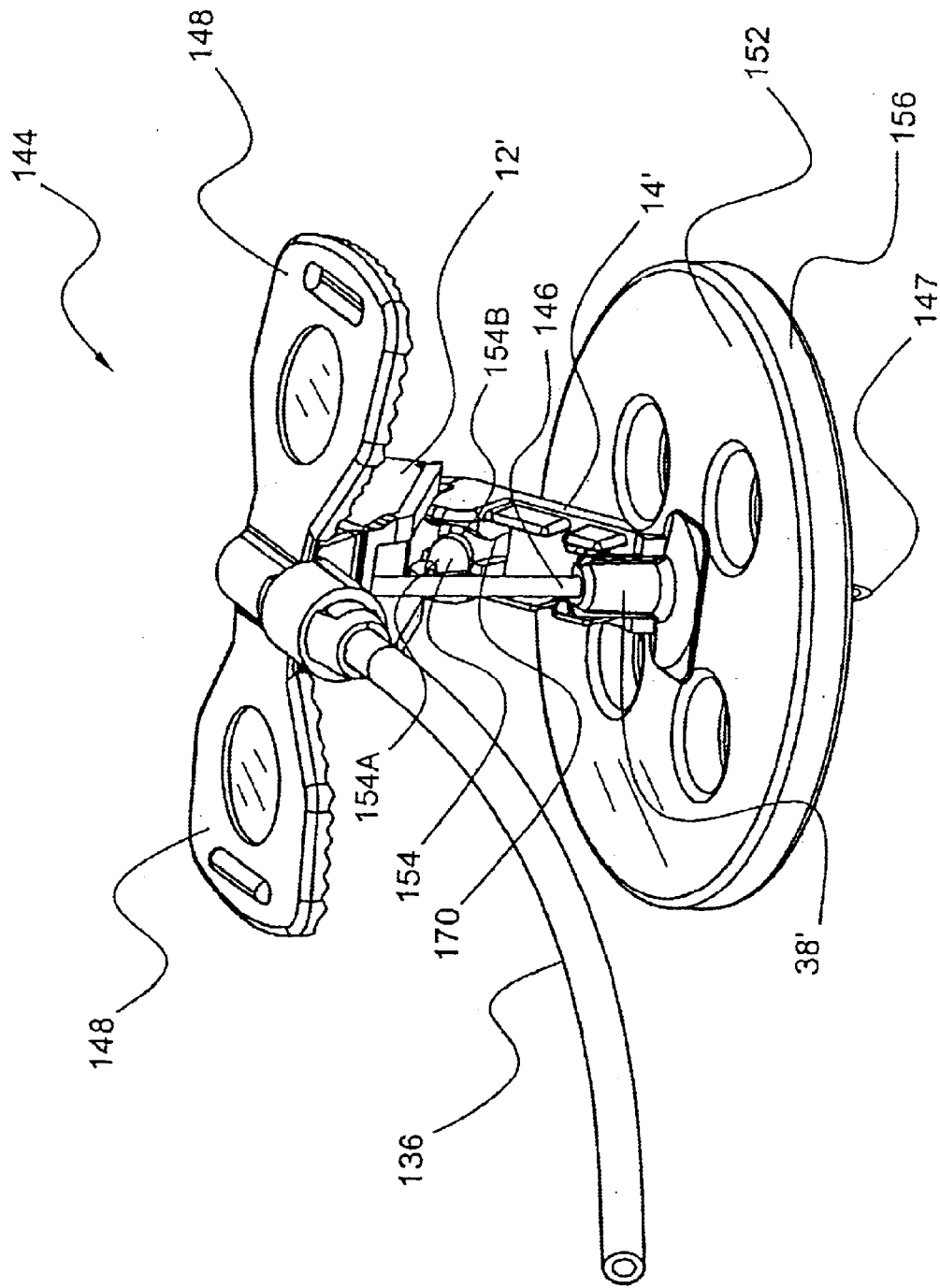
FIG. 50 is a rear view of the safety shield apparatus shown in FIG. 42 showing the embodiment of a needle latch shown in FIG. 49.

FIGS. 42 and 43 show the safety shield apparatus 144 in a pre-use state, while FIGS. 44 and 45 show the post-use and protected state with the shield 150 attached to the needle 146 by means of a needle latch 154 shown in FIGS. 45, 49 and 50. Needle latch 154 has an arcuate outer surface 154A and a radial edge 154B. A deformable interior cavity 154C of latch 154 corresponds to outer surface 154A. Upon actuation of shield 150, needle 146 engages and travels along outer surface 154A until needle 154 becomes disposed over radial edge 154B. Outer surface 154A elastically deforms to facilitate movement of needle 146 thereover and extension of shield 150. Shield 150 is manipulated until the fully extended position is reached. Radial edge 154B prevents movement of needle 146 and consequently shield 150 to the retracted position, thereby locking shield 150 in the fully extended position. Movement of needle 146 is prevented due to the compressive forces created in outer surface 154A and tensile forces in 154B via engagement of needle 146 and radial edge 154B.

As shown in FIGS. 49 and 50, a rib 170 may be utilized for positioning the needle 146 with respect to the needle latch 154. The needle 146 may be latched to the shield 150 by various other means as set forth herein.

The shield 150 may further comprise a disc 152 attached to linear bearing 38', which may be permanently attached or releasably attached. Linear bearing 38' may also be monolithically formed with disc 152. The disc 152 may further include foldable portions (not shown), such as by living hinges, for packaging purposes. Texturing may also be added to the top surface of the disc 152 to enhance gripping of the disc 152. The disc 152 may also be hingedly attached to the distal segment 14' through hinge 182, thereby leaving the linear bearing 38' free from communication with the disc 152. The linear bearing 38' remains connected to the distal segment 14' through living hinge 78.

Figure 51:
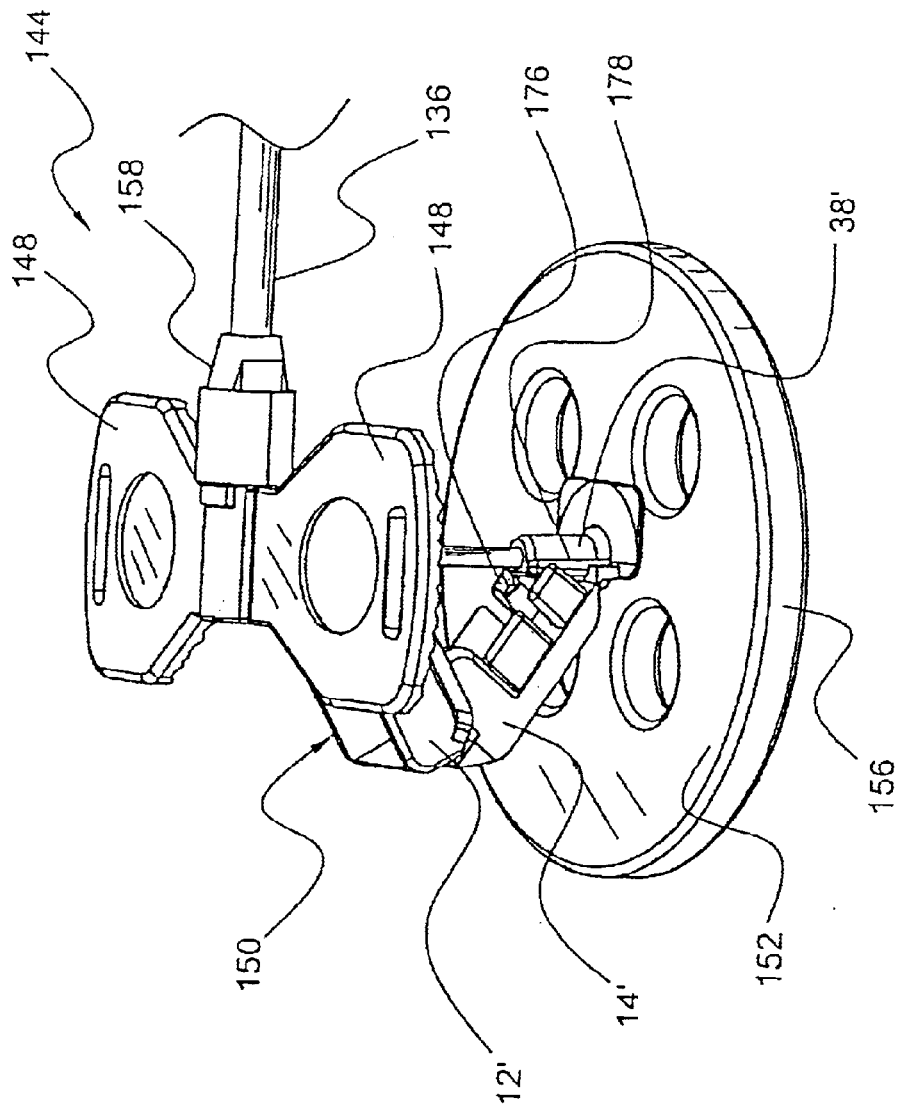
FIG. 51 is a perspective view of the safety shield apparatus illustrated in FIG. 42 showing an additional lockout feature.

Referring to the embodiment shown in FIG. 51, an additional lockout feature may be added for securing the safety shield apparatus 144 in the lockout mode. For the embodiment shown in FIG. 51, the lockout is accomplished by engagement of latches 176 disposed on the distal segment 14' to flanges 178 disposed on the linear bearing 38'.

The shield 150 is passively activated upon withdrawal of the needle 146 from a patient, wherein wings 148 may be used to facilitate insertion and withdrawal of the safety shield apparatus 144. One method of withdrawing the needle 146 from a patient includes the steps of holding the disc 152 against a patient while pulling the wings 148 away from the patient. Once the needle latch 154 engages the needle 146, the safety shield apparatus 144 may be removed. It is contemplated that disc 152 is adherently attached to the patient. Disc 152 may also be releasable from linear bearing 38', similar to that described with regard to tape down member 132.

Figure 48:
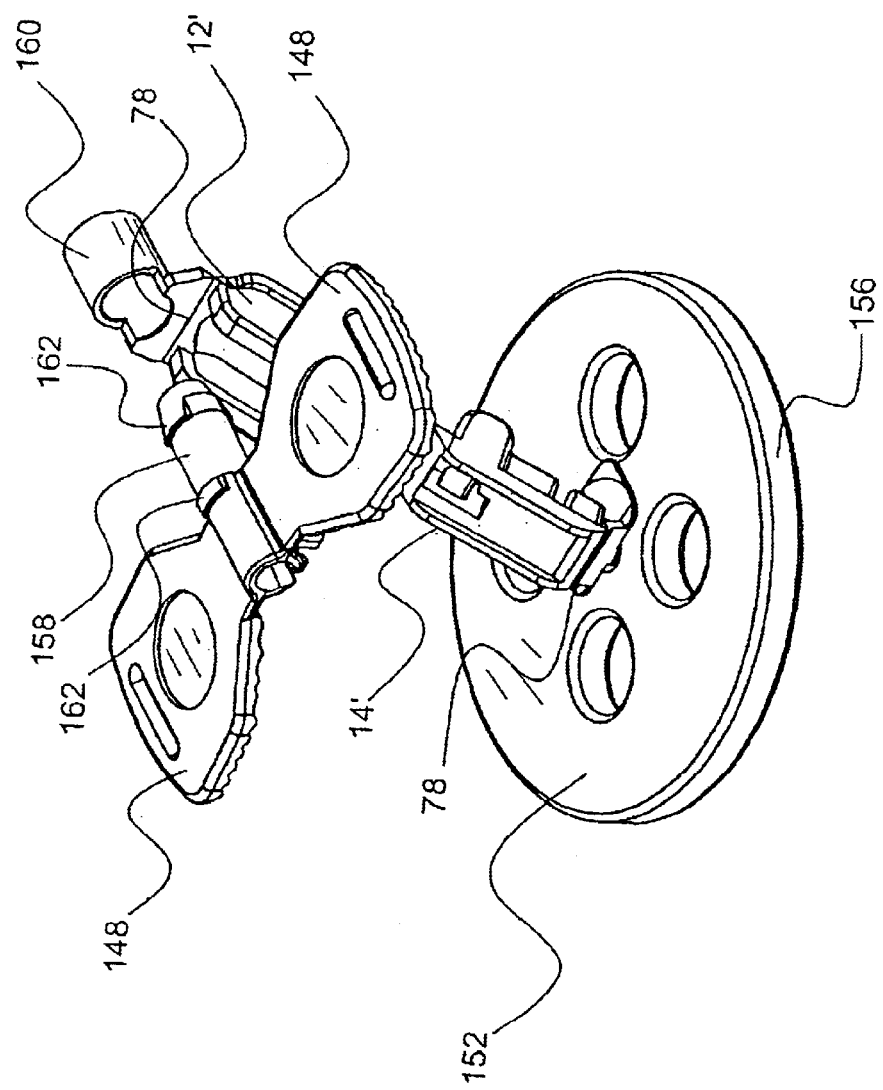
FIG. 48 is a perspective view of the safety shield apparatus illustrated in FIG. 42 showing an alternate embodiment of a linear bearing and the shield separated from the hub and wing assembly.

The hinges connecting segments 12' and 14' and the linear bearing 38' may be flexible living hinges 78, pinned hinges, or equivalents thereof that provide for hinged connections of the segments 12' and 14' and the linear bearing 38' (see, e.g., FIG. 48). Moreover, the number of hingedly connected segments depends upon the needle 146 length and device length required to extend the shield 144 beyond the distal end 147 of the needle 146. Embodiments of the safety shield apparatus 144 may, therefore, include two or more segments.

As shown in the embodiment illustrated in FIG. 42, the needle 146 has a proximal end and a distal end 147 with the proximal end of the needle 146 affixed in a hub 158. The wings 148 may be affixed to the needle hub. In the embodiment shown in FIG. 48, the safety shield apparatus 144 is assembled by inserting hub 158 into the collar 160. Flared surfaces 162 may be included on the hub 158 to engage the collar 160. The needle hub may also be configured to attach an extension set tubing 136.

Figure 46:
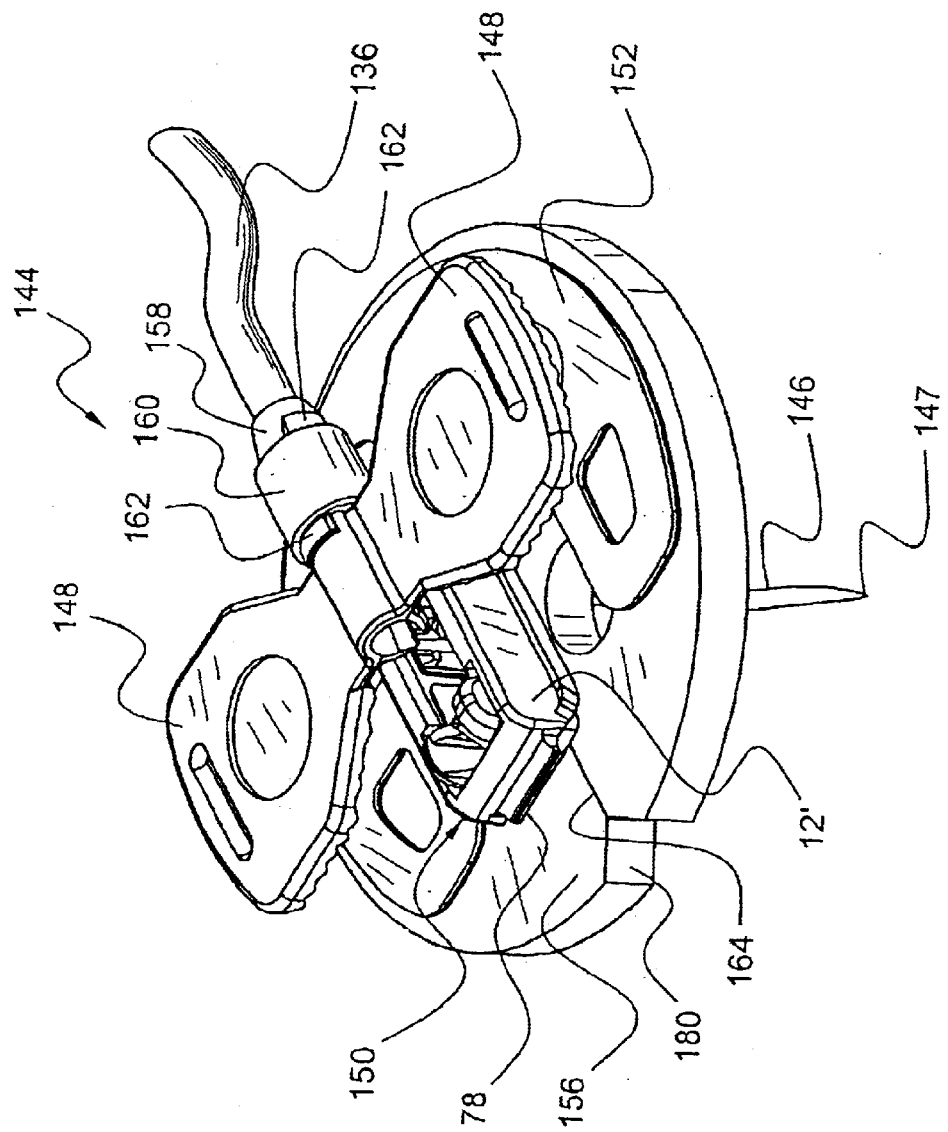
FIG. 46 is a perspective view of the safety shield apparatus illustrated in FIG. 42 in a retracted position showing an alternate embodiment of a linear bearing with a foam disc.
Figure 47:
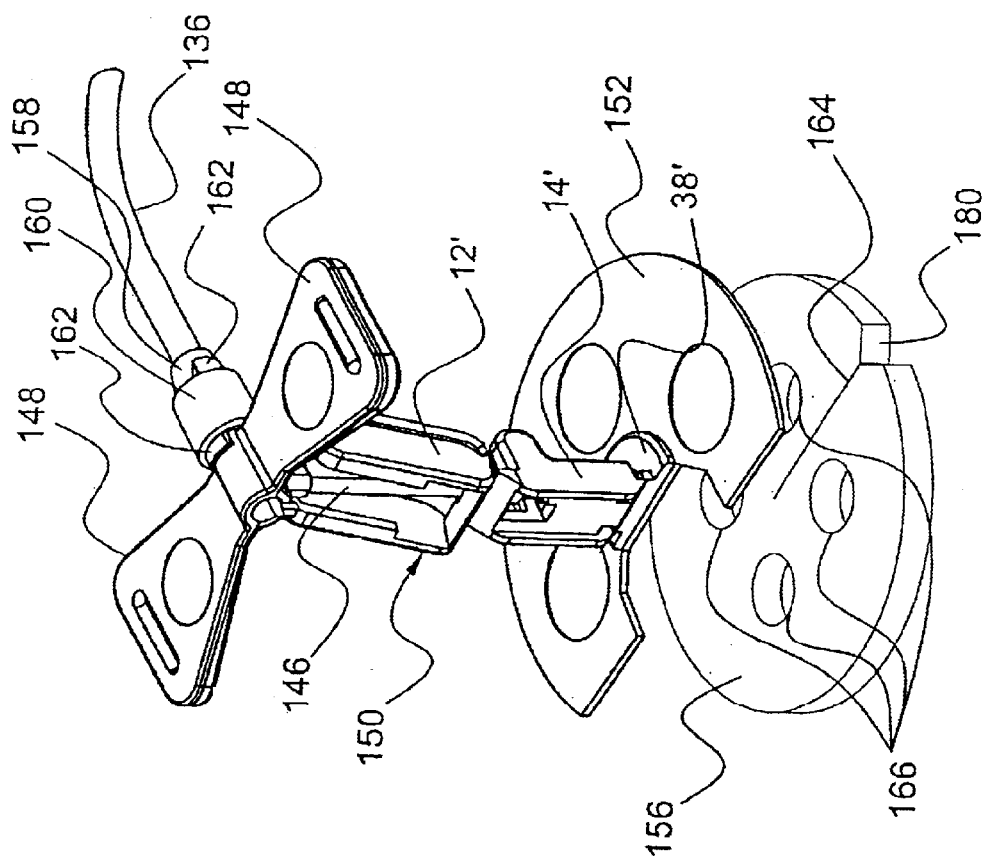
FIG. 47 is a perspective view of the safety shield apparatus shown in FIG. 46 fully extended.

Referring to FIGS. 46 and 47, an embodiment of the safety shield apparatus 144 is shown further comprising a pad 156, which may be added underneath the disc 152 for patient comfort and as a spacer between a patient's skin and the disc 152. The pad 156 may be comprised of a foam material such as a closed-cell foam, polyurethane open-cell foam, or an equivalent crushed or densified, felted material. The pad 156 may be an absorbent, breathable material that may also be capable of wicking moisture. The pad 156 may also be impregnated with an antimicrobial agent, such as chlorhexidine or equivalent material. The pad 156 may also be comprised of a foam material with a thin film coating on either side including, but not limited to, polyolefin, breathable polyurethane, or other equivalent materials. The thin film coating may also be perforated.

The pad 156 may be separately packaged in a sterile container for use as a replacement pad for an existing dressing. The pad 156 may also be used as a dressing, which may replace or supplement a gauze dressing.

The pad 156 may have a friction fit capability for attachment to the needle 146, with a possible slit 164 included for ease of attachment to the safety shield apparatus 144. A notch 180 may be added to slit 164 to assist in guiding the pad 156 into the proper position on the needle 146. Holes 166 may be added to the pad 156 for purposes such as aiding in visibility and increasing air flow to the pad 156. Similar holes may be added to the disc 152 for the same purposes.

Figure 52:
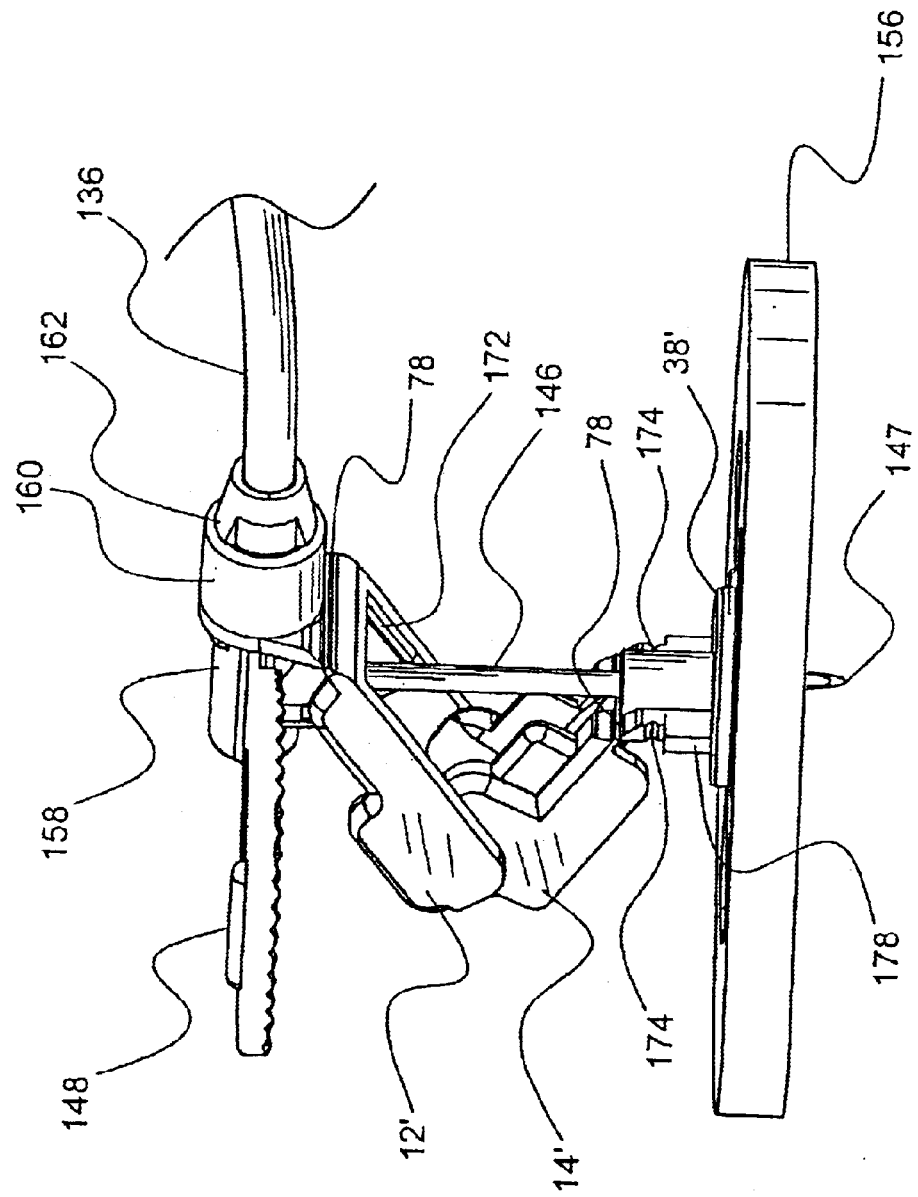
FIG. 52 is a perspective view of the safety shield apparatus illustrated in FIG. 42 showing an embodiment of a latch for retaining the safety shield apparatus in a retracted position.

Referring to the embodiment shown in FIG. 52, the safety shield apparatus 144 may be retained in the retracted position by a flange 172 disposed on the proximal segment 12' engaging notches 174 in a flange 178 disposed on the linear bearing 38'. Alternative embodiments may include a flange disposed on the hub 158 or distal segment 14' with corresponding notches located on an alternate segment or hub 158.

In another embodiment the hub may be configured to include a luer fitting for attachment to various needle devices such as a syringe or IV set.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a needle hub supporting a needle having a distal end;
   at least two arms extending from the needle hub, the arms being spaced apart to define a cavity that is configured for disposal of a shield; and
   the shield having a proximal end and a distal end, the proximal end being connected to the needle hub and separately fixed with at least one of the arms, the proximal end being movable relative to the needle hub and the arms,
   the shield including at least one guide disposed between the proximal end and the distal end, the guide being configured to engage the needle to facilitate extension of the shield from a retracted position to an extended position.

2. A medical needle shield apparatus as recited in claim 1, wherein the arms are diametrically disposed about the needle hub.

3. A medical needle shield apparatus as recited in claim 1, wherein the shield includes a plurality of hingedly connected segments including a proximal segment that is connected to the needle hub and separately connected to the at least one of the arms, the proximal segment being movable relative to the needle hub and the arms.

4. A medical needle shield apparatus as recited in claim 1, wherein the shield includes a plurality of hingedly connected segments including a distal segment that has a bearing configured to engage the needle and facilitate extension of the shield along the needle.

5. A medical needle shield apparatus as recited in claim 4, wherein the distal segment includes a distal end surface configured to engage the distal end of the needle when the shield is in the extended position to prevent displacement of the shield from the extended position.

6. A medical needle shield apparatus as recited in claim 3, wherein the plurality of hingedly connected segments includes at least one intermediate segment being disposed between the proximal segment and a distal segment.

7. A medical needle shield apparatus as recited in claim 6, wherein a first intermediate segment is connected to the proximal segment and a second intermediate segment is connected to the first intermediate segment and the distal segment.

8. A medical needle shield apparatus as recited in claim 6, wherein the distal segment includes a latch that engages a catch of the at least one intermediate segment in a configuration that locks the shield in the extended position.

9. A medical needle shield apparatus as recited in claim 7, further comprising a plurality of guides wherein the first intermediate segment includes a first guide and the second intermediate segment includes a second guide.

10. A medical needle shield apparatus as recited in claim 3, wherein at least one of the arms includes a protrusion that engages a capture aperture of the proximal segment in a configuration that locks the shield in the extended position.

11. A medical needle shield apparatus as recited in claim 1, wherein at least one of the arms includes a latch that engages the shield in a configuration to retain the shield in the retracted position.

12. A medical needle shield apparatus as recited in claim 4, wherein at least one of the arms includes a latch that engages the distal segment in a configuration to retain the shield in the retracted position.

13. A medical needle shield apparatus comprising:
 a needle hub supporting a needle having a distal end;
 a pair of arms extending from the needle hub and being spaced apart to define a cavity; and
 a shield having a plurality of hingedly connected segments being movable between a retracted position and an extended position, the shield including a proximal segment connected to the needle hub and separately connected with the arms, the proximal segment being disposable in the cavity and movable relative to the needle hub and the arms,
 the shield further including at least one intermediate segment being disposed between the proximal segment and a distal segment,
 wherein the distal segment includes a latch that engages a catch of the at least one intermediate segment in a configuration that locks the shield in the extended position.

14. A medical needle shield apparatus as recited in claim 13, wherein the distal segment includes a bearing configured to support the needle and facilitate extension of the shield along the needle.

15. A medical needle shield apparatus as recited in claim 14, wherein the bearing is hingedly connected to the distal segment.

16. A medical needle shield apparatus as recited in claim 13, wherein a first intermediate segment is connected to the proximal segment and a second intermediate segment is connected to the first intermediate segment and the distal segment.

17. A medical needle shield apparatus as recited in claim 13, wherein the at least one intermediate segment includes at least one guide being configured to engage the needle to facilitate extension of the shield between the retracted position and the extended position.

18. A medical needle shield apparatus as recited in claim 13, wherein the arms include protrusions that engage capture apertures of the proximal segment in a configuration that locks the shield in the extended position.

19. A medical needle shield apparatus as recited in claim 13, wherein the arms include latches that engage the shield in a configuration to retain the shield in the refracted position.

20. A medical needle shield apparatus comprising:
 a needle hub supporting a needle having a distal end; and
 a shield being extensible between a refracted position and an extended position, the shield including a proximal portion, an intermediate portion and a distal portion,
 the proximal portion including a pair of spaced apart arms extending from the needle hub and a proximal segment extending from the needle hub and separately fixed with the arms,
 the intermediate portion including a first intermediate segment hingedly connected to the proximal segment and a second intermediate segment hingedly connected to the first intermediate segment, the first intermediate segment including a guide that is configured to engage the needle to facilitate extension of the shield between the refracted position and the extended position, and
 the distal portion including a distal segment having a bearing configured to engage the needle and facilitate extension of the shield along the needle,
 wherein the distal segment engages the proximal portion in a configuration that retains the shield in the retracted position and the distal segment includes a distal end surface configured to engage the distal end of the needle when the shield is in the extended position to prevent displacement of the shield from the extended position.

* * * * *